US011213361B2

(12) United States Patent
Denlinger et al.

(10) Patent No.: US 11,213,361 B2
(45) Date of Patent: Jan. 4, 2022

(54) ROBOTIC SURGICAL SYSTEMS WITH MECHANISMS FOR SCALING SURGICAL TOOL MOTION ACCORDING TO TISSUE PROXIMITY

(71) Applicant: Cilag GmbH International, Zug (CH)

(72) Inventors: Clinton W. Denlinger, Cincinnati, OH (US); Gregory W. Johnson, Minneapolis, MN (US); Charles J. Scheib, Loveland, OH (US); Jeffrey S. Swayze, West Chester, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/354,440

(22) Filed: Mar. 15, 2019

(65) Prior Publication Data

US 2020/0289220 A1    Sep. 17, 2020

(51) Int. Cl.
| | |
|---|---|
| *A61B 34/35* | (2016.01) |
| *A61B 5/055* | (2006.01) |
| *A61B 34/37* | (2016.01) |
| *A61B 34/00* | (2016.01) |
| *B25J 9/16* | (2006.01) |
| *B25J 13/08* | (2006.01) |
| *A61B 34/30* | (2016.01) |

(52) U.S. Cl.
CPC ............. *A61B 34/37* (2016.02); *A61B 34/74* (2016.02); *A61B 34/77* (2016.02); *B25J 9/1664* (2013.01); *B25J 9/1694* (2013.01); *B25J 13/085* (2013.01); *A61B 2034/302* (2016.02); *A61B 2034/742* (2016.02)

(58) Field of Classification Search
CPC .......... A61B 34/37; A61B 34/20; A61B 34/72
See application file for complete search history.

(56) References Cited

U.S. PATENT DOCUMENTS

| | | |
|---|---|---|
| 4,785,180 A | 11/1988 | Dietrich et al. |
| 5,855,583 A | 1/1999 | Wang et al. |
| 6,804,012 B2 | 10/2004 | Gombert |
| 6,951,535 B2 | 10/2005 | Ghodoussi et al. |
| 7,516,675 B2 | 4/2009 | Kurtz et al. |
| 7,747,311 B2 | 6/2010 | Quaid, III |
| 8,063,883 B2 | 11/2011 | Senft et al. |
| 8,079,950 B2 | 12/2011 | Stern et al. |
| 8,224,484 B2 | 7/2012 | Swarup et al. |

(Continued)

FOREIGN PATENT DOCUMENTS

KR    20120068597 A    6/2012

OTHER PUBLICATIONS

Kurata, et al., "Time-of-flight Near-infrared Spectroscopy for Nondestructive Measurement of Internal Quality in Grapefruit," Journal, May 2013, pp. 225-228, vol. 138, Issue 3, Journal of the American Society for Horticultural Science, Japan.

*Primary Examiner* — Muhammad S Islam
*Assistant Examiner* — Charles S Laughlin

(57) ABSTRACT

A surgical system is disclosed including a surgical tool, a motor operably coupled to the surgical tool, and a control circuit coupled to the motor. The control circuit is configured to receive an instrument motion control signal indicative of a user input, cause the motor to move the surgical tool in response to the instrument motion control signal, receive an input signal indicative of a distance between the surgical tool and tissue, and scale the movement of the surgical tool to the user input in accordance with the input signal.

19 Claims, 39 Drawing Sheets

(56) References Cited

U.S. PATENT DOCUMENTS

| | | |
|---|---|---|
| 8,888,789 B2 | 11/2014 | Prisco et al. |
| 8,996,173 B2 | 3/2015 | Itkowitz et al. |
| 9,055,961 B2 | 6/2015 | Manzo et al. |
| 9,161,817 B2 | 10/2015 | Olson et al. |
| 9,186,046 B2 | 11/2015 | Ramamurthy et al. |
| 9,274,047 B2 | 3/2016 | Velten et al. |
| 9,500,473 B2 | 11/2016 | Ramamurthy et al. |
| 10,052,766 B2 | 8/2018 | Shirakyan et al. |
| 10,485,617 B2 | 11/2019 | Crawford et al. |
| 10,499,996 B2 | 12/2019 | de Almeida Barreto |
| 10,548,679 B2 | 2/2020 | Carlson et al. |
| 10,792,034 B2 | 10/2020 | Scheib et al. |
| 10,835,332 B2 | 11/2020 | Manzo et al. |
| 10,925,598 B2 | 2/2021 | Scheib et al. |
| 2008/0001919 A1 | 1/2008 | Pascucci |
| 2016/0256184 A1* | 9/2016 | Shelton, IV ......... A61B 17/072 |
| 2017/0055819 A1 | 3/2017 | Hansen et al. |
| 2017/0224428 A1* | 8/2017 | Kopp .................... A61B 34/30 |
| 2017/0251900 A1 | 9/2017 | Hansen et al. |
| 2019/0200905 A1 | 7/2019 | Shelton, IV et al. |
| 2019/0201111 A1 | 7/2019 | Shelton, IV et al. |
| 2019/0201120 A1 | 7/2019 | Shelton, IV et al. |
| 2019/0201142 A1 | 7/2019 | Shelton, IV et al. |
| 2019/0307524 A1 | 10/2019 | Popovic |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0289205 A1 | 9/2020 | Scheib et al. |
| 2020/0289216 A1 | 9/2020 | Denlinger et al. |
| 2020/0289217 A1 | 9/2020 | Denlinger et al. |
| 2020/0289219 A1 | 9/2020 | Denlinger et al. |
| 2020/0289221 A1 | 9/2020 | Denlinger et al. |
| 2020/0289222 A1 | 9/2020 | Denlinger et al. |
| 2020/0289223 A1 | 9/2020 | Denlinger et al. |
| 2020/0289228 A1 | 9/2020 | Denlinger et al. |
| 2020/0289229 A1 | 9/2020 | Denlinger et al. |
| 2020/0289230 A1 | 9/2020 | Denlinger et al. |

* cited by examiner

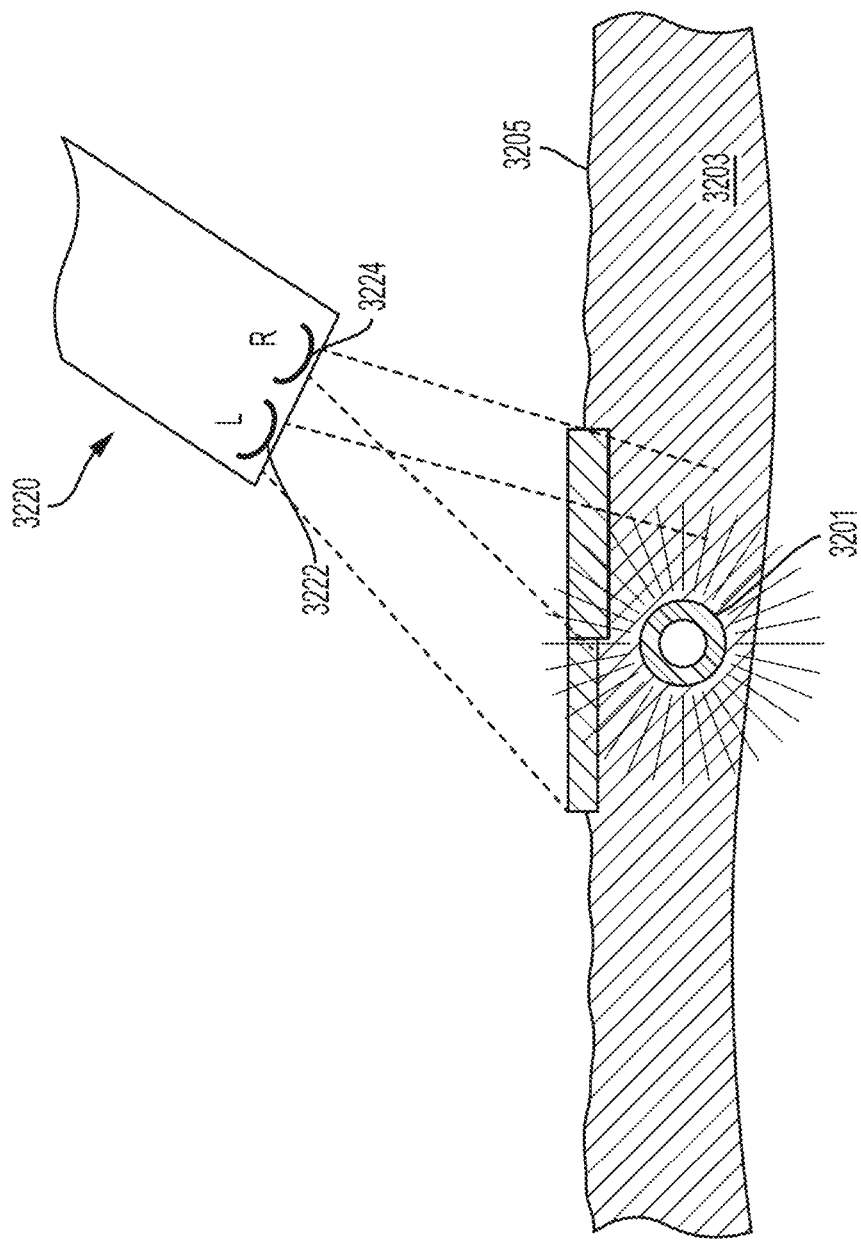

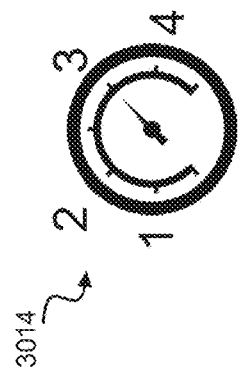
FIG. 29
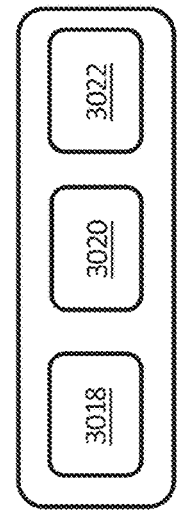
FIG. 30
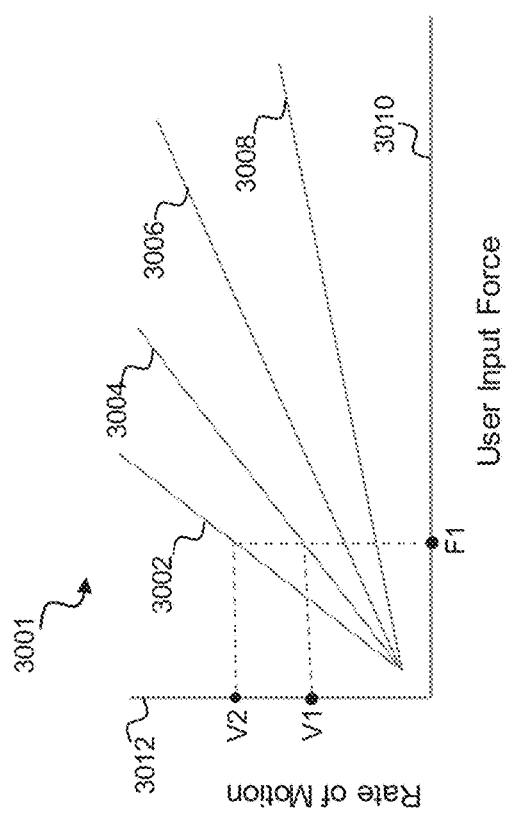
FIG. 28
| F1 | P1 | P2 | ... | Pn |
|----|----|----|-----|----|
| F1 | $V_{a1}$ | $V_{b1}$ | ... | $V_{z1}$ |
| F2 | $V_{a2}$ | $V_{b2}$ | ... | $V_{z2}$ |
| ... | ... | ... | ... | ... |
| Fn | $V_{an}$ | $V_{bn}$ | ... | $V_{zn}$ |
FIG. 31

ROBOTIC SURGICAL SYSTEMS WITH MECHANISMS FOR SCALING SURGICAL TOOL MOTION ACCORDING TO TISSUE PROXIMITY

BACKGROUND

Surgical systems often incorporate an imaging system, which can allow the clinician(s) to view the surgical site and/or one or more portions thereof on one or more displays such as a monitor. The display(s) can be local and/or remote to a surgical theater. An imaging system can include a scope with a camera that views the surgical site and transmits the view to a display that is viewable by a clinician. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

Robotic systems can be actuated or remotely-controlled by one or more clinicians positioned at control consoles. Input motions at the control console(s) can correspond to actuations of a robotic arm and/or a robotic tool coupled thereto. In various instances, the robotic system and/or the clinician(s) can rely on views and/or information provided by an imaging system to determine the desired robotic actuations and/or the corresponding suitable input motions. The inability of certain imaging systems to provide certain visualization data and/or information may present challenges and/or limits to the decision-making process of the clinician and/or the controls for the robotic system.

SUMMARY

In various embodiments, a surgical system is disclosed including a surgical tool, a motor operably coupled to the surgical tool, and a control circuit coupled to the motor. The control circuit is configured to receive an instrument motion control signal indicative of a user input, cause the motor to move the surgical tool in response to the instrument motion control signal, receive an input signal indicative of a distance between the surgical tool and tissue, and scale the movement of the surgical tool to the user input in accordance with the input signal.

In various embodiments, a surgical system is disclosed including a surgical tool, a motor operably coupled to the surgical tool, and a control circuit coupled to the motor. The control circuit is configured to receive an instrument motion control signal indicative of a user input, cause the motor to move the surgical tool in response to the instrument motion control signal, determine a distance between the surgical tool and tissue, and scale the movement of the surgical tool to the user input in accordance with the distance.

In various embodiments, a surgical system is disclosed including a surgical tool, a motor operably coupled to the surgical tool, and a control circuit coupled to the motor. The control circuit is configured to receive an instrument motion control signal indicative of a user input, cause the motor to move the surgical tool in response to the instrument motion control signal, receive an input signal indicative of a distance between the surgical tool and tissue, and select between a gross motion mode and a fine motion mode of the surgical tool based on distance between the surgical tool and the tissue.

FIGURES

The novel features of the various aspects are set forth with particularity in the appended claims. The described aspects, however, both as to organization and methods of operation, may be best understood by reference to the following description, taken in conjunction with the accompanying drawings in which:

FIG. 13F is a schematic of a surgical visualization system including a three-dimensional camera, wherein the surgical visualization system is configured to identify a critical structure that is embedded within tissue, according to at least one aspect of the present disclosure.

FIGS. 13G and 13H are views of the critical structure taken by the three-dimensional camera of FIG. 13F, in which FIG. 13G is a view from a left-side lens of the three-dimensional camera and FIG. 13H is a view from a right-side lens of the three-dimensional camera, according to at least one aspect of the present disclosure.

Figure 13:
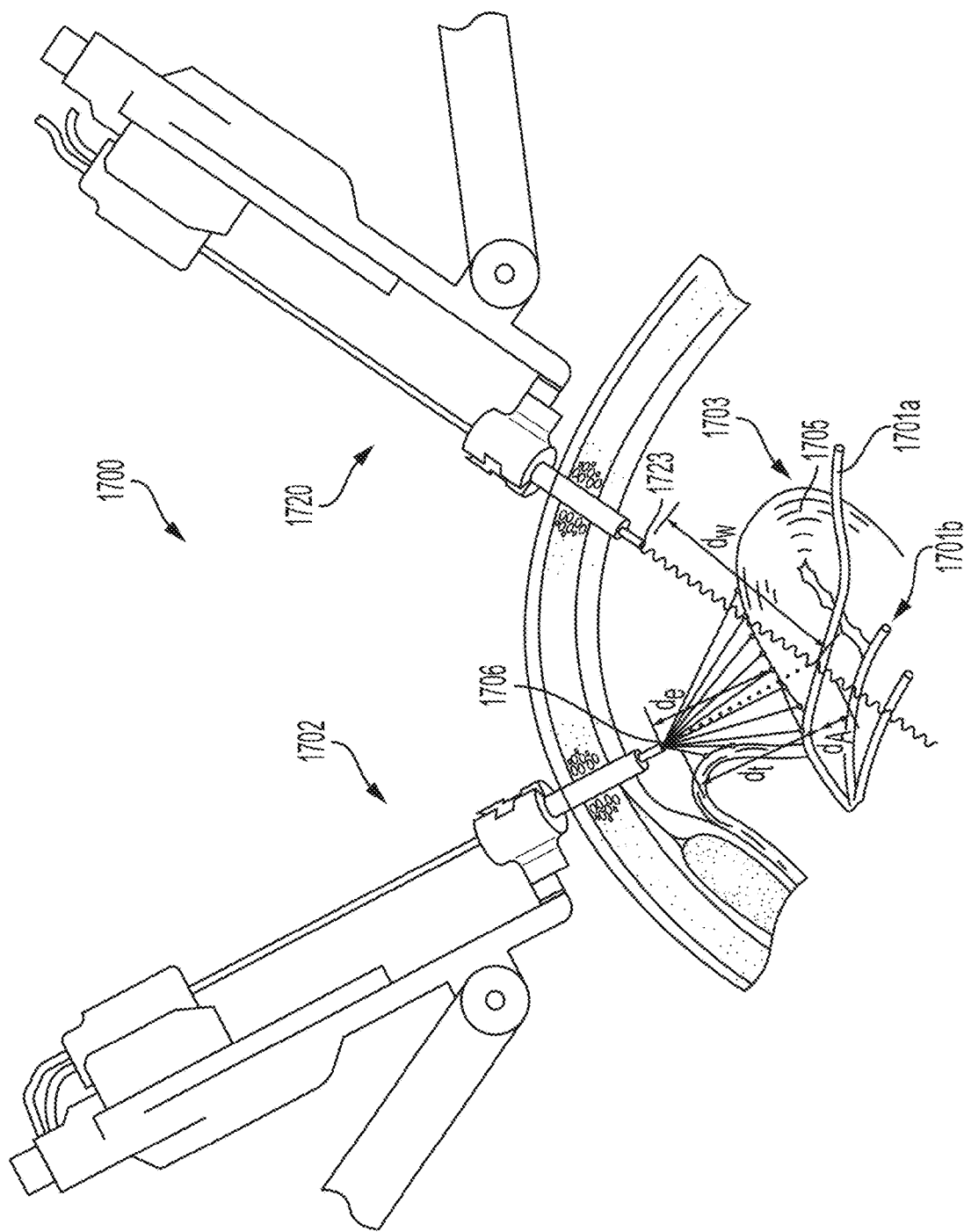
FIG. 13 is a schematic of a surgical visualization system including an imaging device and a surgical device, the surgical visualization system configured to identify a critical structure below a tissue surface, according to at least one aspect of the present disclosure.
Figure 13B:
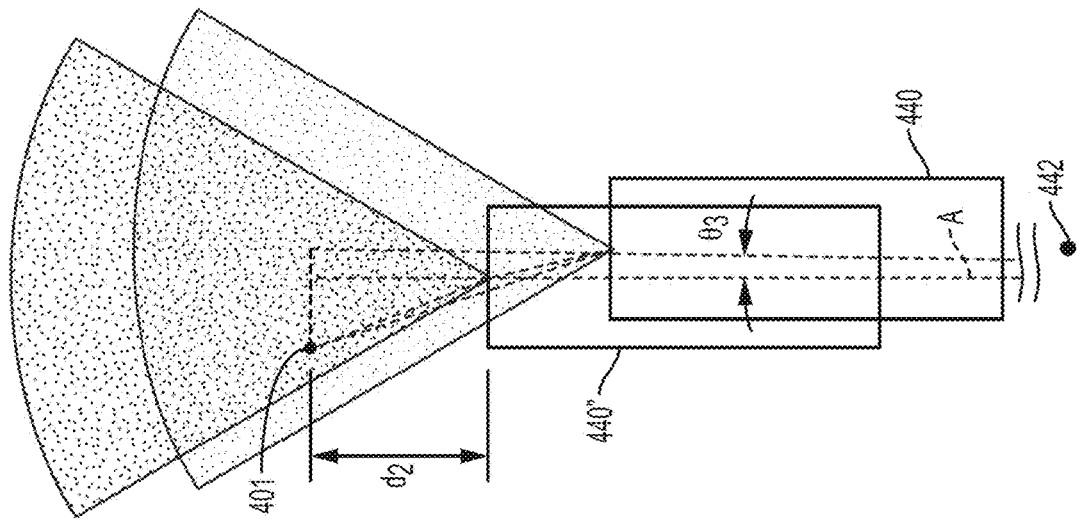
FIG. 13B is a schematic of the surgical visualization system of FIG. 13A, in which the camera is moved axially and rotationally between a plurality of known positions to determine a position of the embedded critical structure, according to at least one aspect of the present disclosure.
Figure 13A:
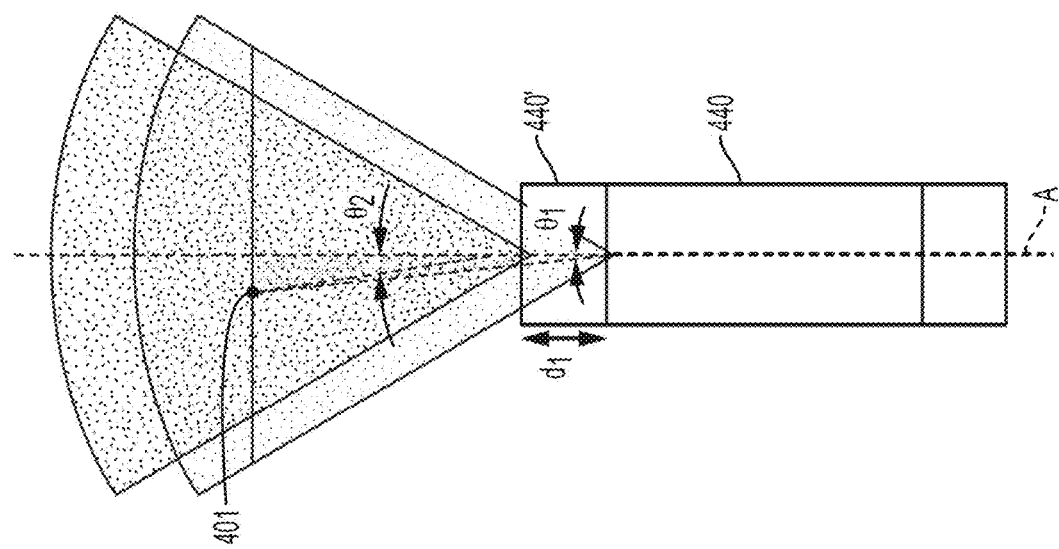
FIG. 13A is a schematic of a surgical visualization system utilizing a camera that is moved axially between a plurality of known positions to determine a position of an embedded critical structure, according to at least one aspect of the present disclosure.
Figure 13D:
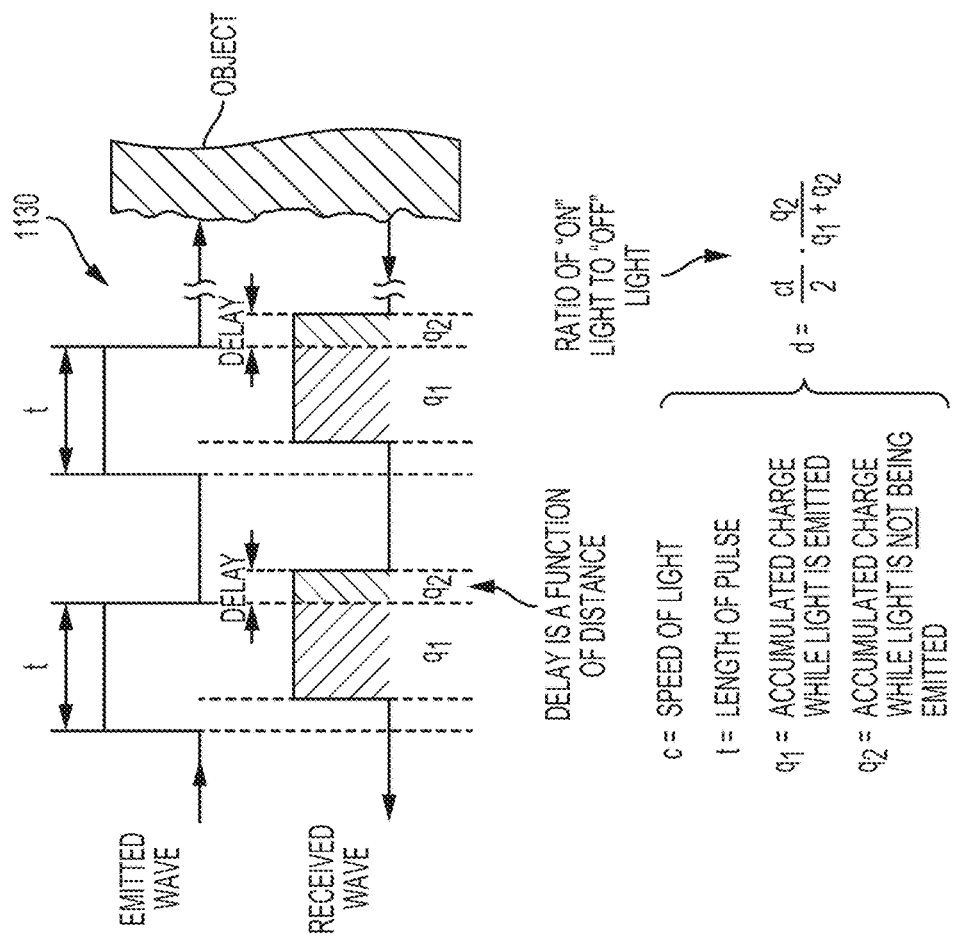
FIG. 13D is a schematic of an emitted wave, a received wave, and a delay between the emitted wave and the received wave of the NIR time-of-flight measurement system of FIG. 13C, according to at least one aspect of the present disclosure.
Figure 13C:
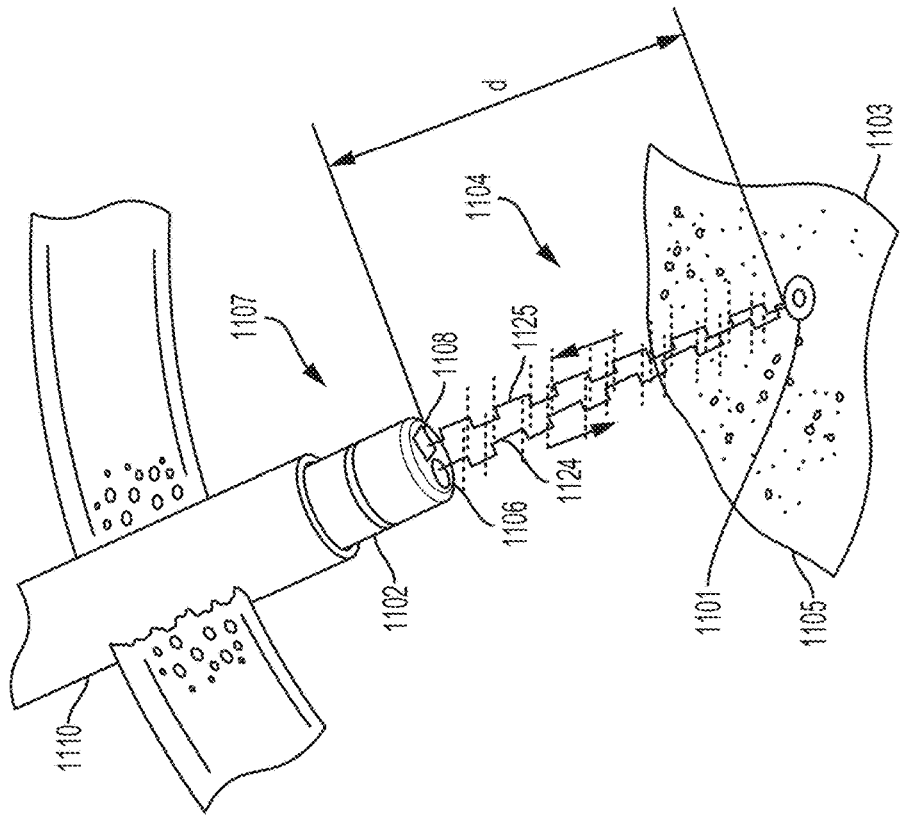
FIG. 13C is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.
Figure 13E:
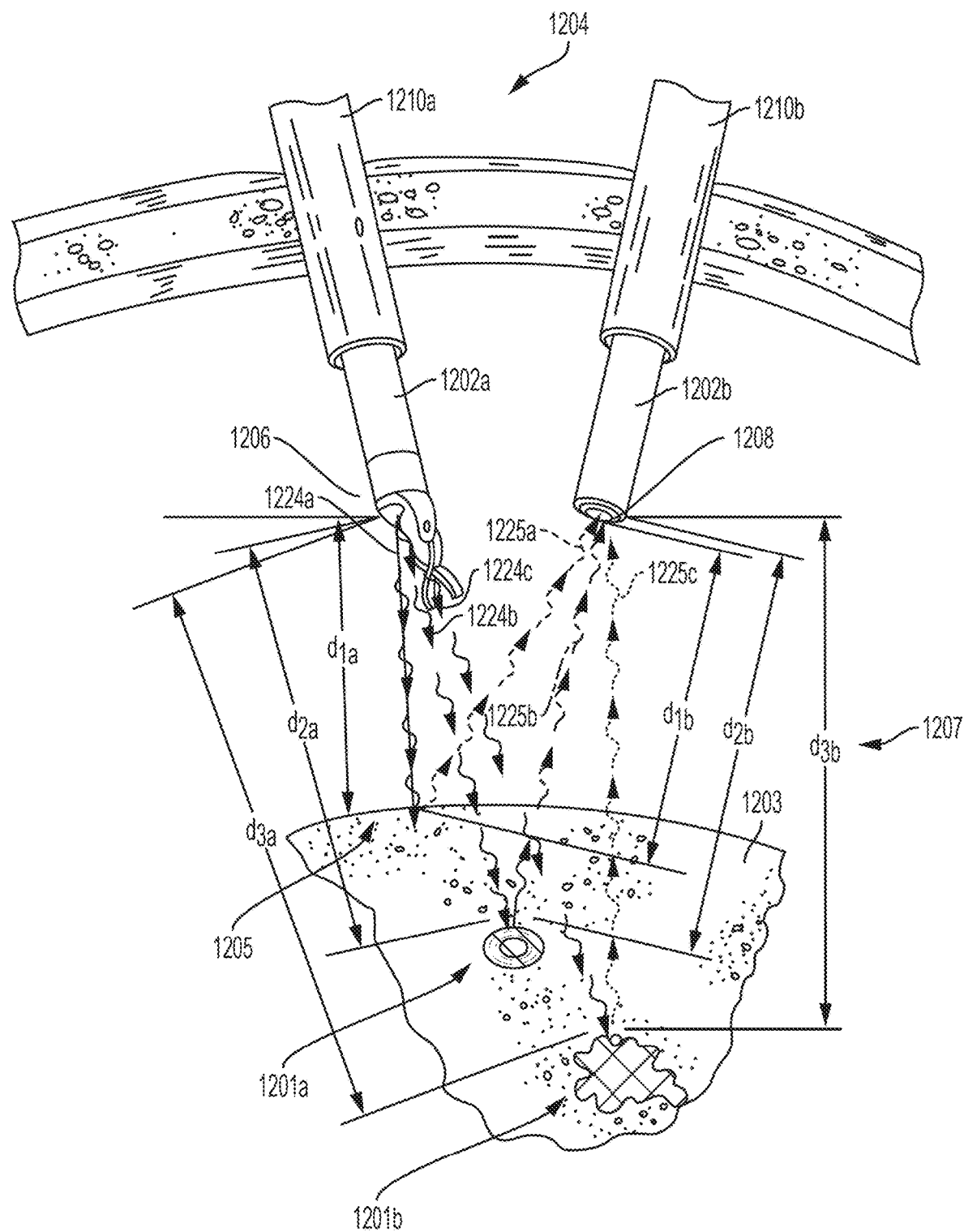
FIG. 13E illustrates a NIR time-of-flight measurement system configured to sense a distance to different structures, the time-of-flight measurement system including a transmitter (emitter) and a receiver (sensor) on separate devices, according to one aspect of the present disclosure.
Figures 13G, 13H:
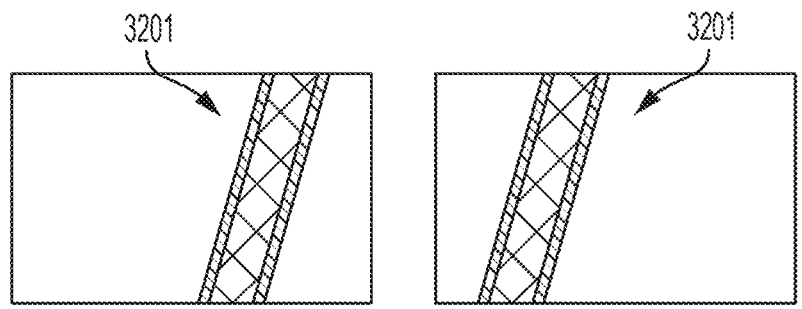
Figure 13I:
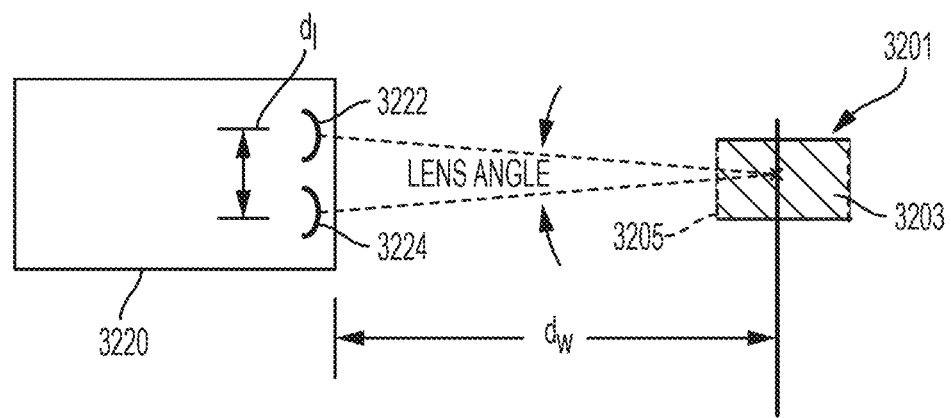
FIG. 13I is a schematic of the surgical visualization system of FIG. 13F, in which a camera-to-critical structure distance $d_w$ from the three-dimensional camera to the critical structure can be determined, according to at least one aspect of the present disclosure.
Figure 13J:
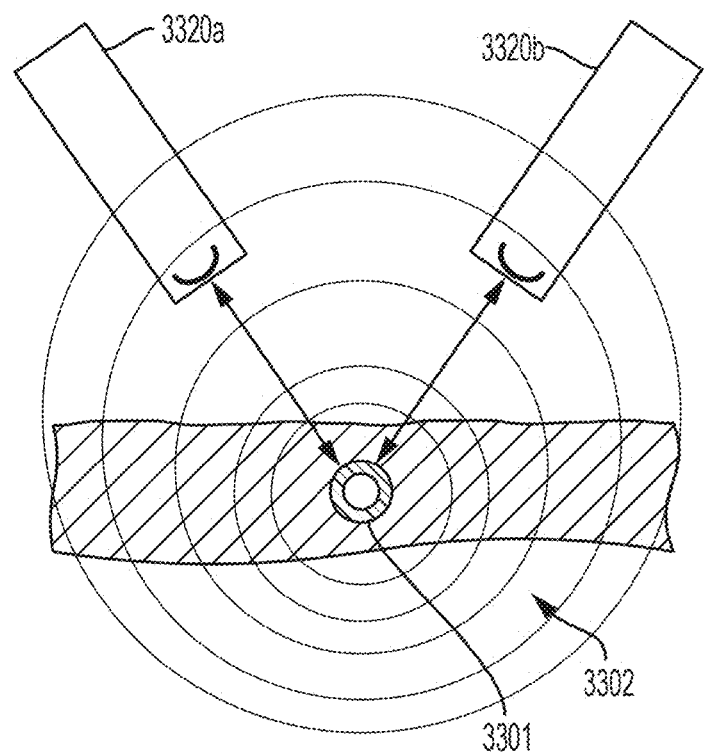
FIG. 13J is a schematic of a surgical visualization system utilizing two cameras to determine the position of an embedded critical structure, according to at least one aspect of the present disclosure.
Figure 13K:
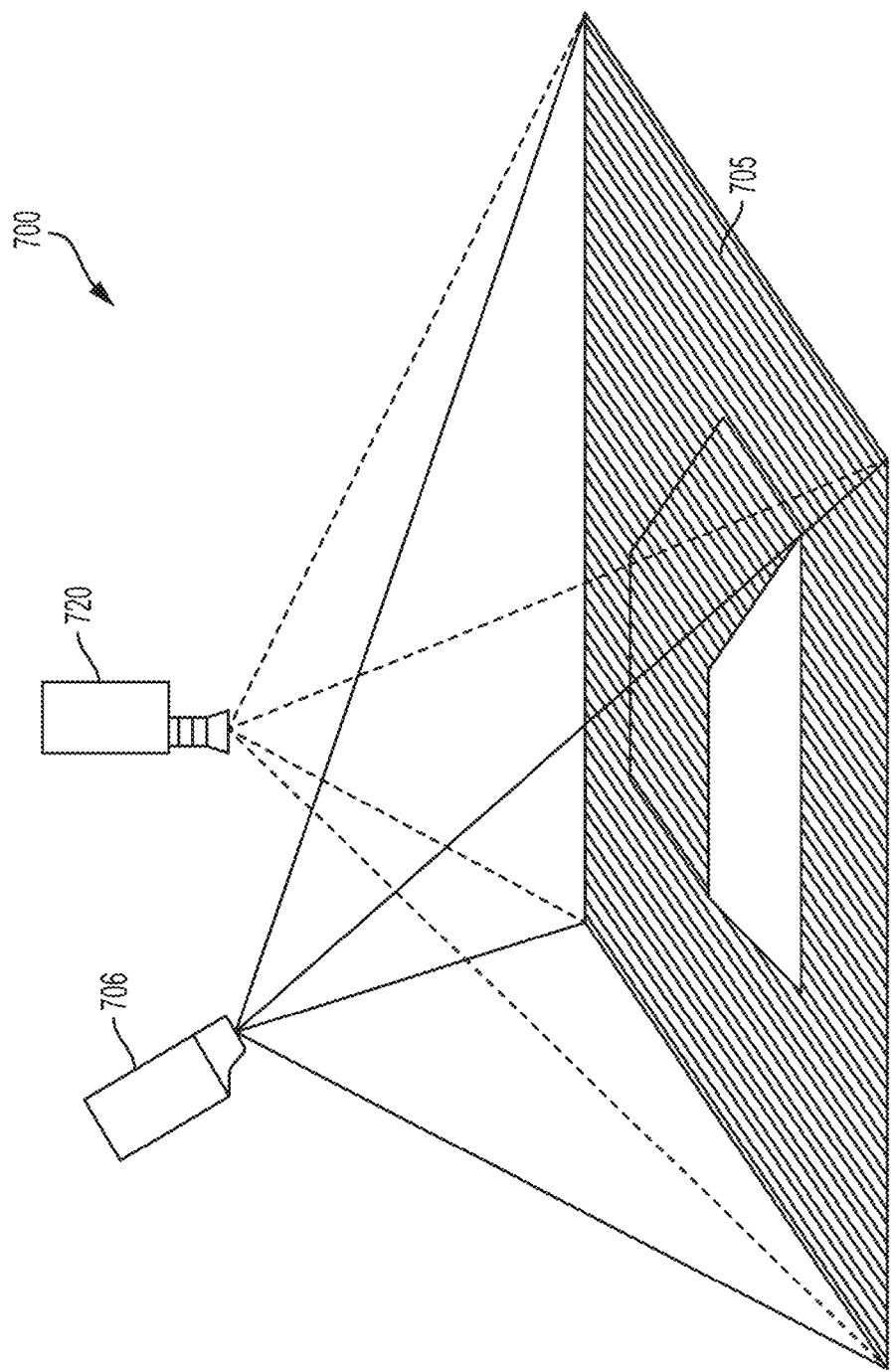
FIG. 13K is a schematic of a structured light source for a surgical visualization system, according to at least one aspect of the present disclosure.
Figure 13L:
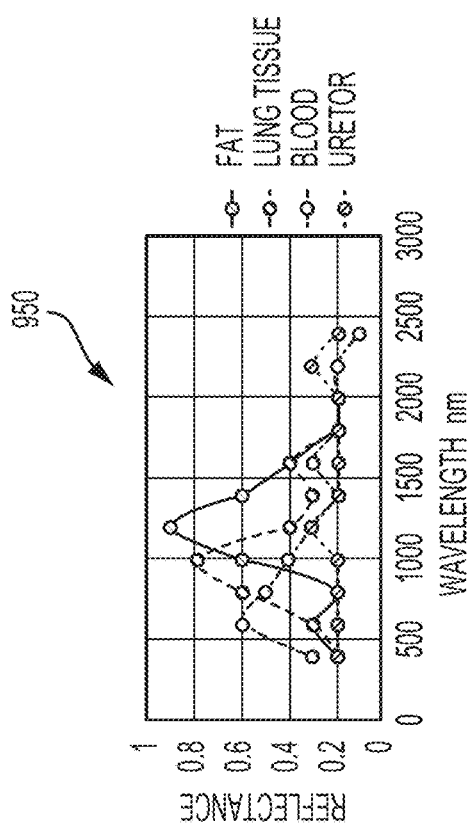
Figure 13N:
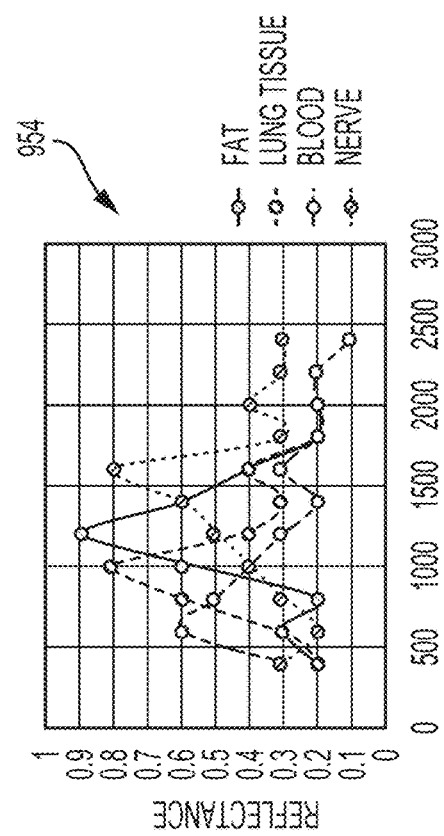
Figure 13M:
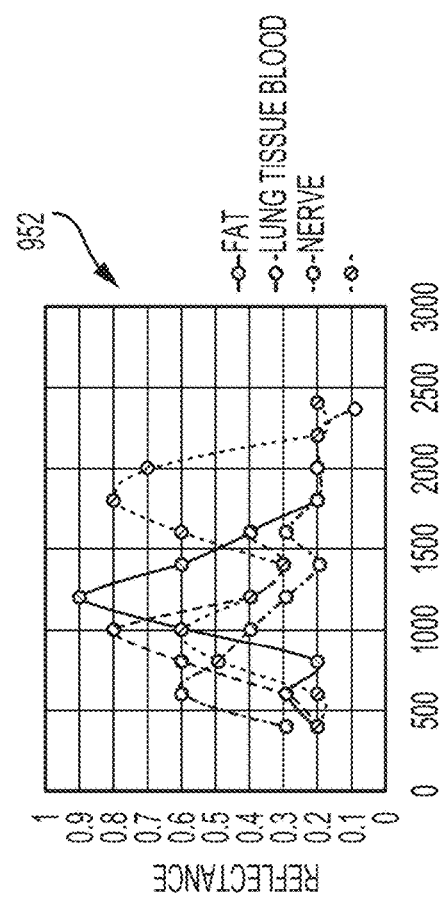

FIGS. 13L-13N depict illustrative hyperspectral identifying signatures to differentiate anatomy from obscurants, wherein FIG. 13L is a graphical representation of a ureter signature versus obscurants, FIG. 13M is a graphical representation of an artery signature versus obscurants, and FIG. 13N is a graphical representation of a nerve signature versus obscurants, according to at least one aspect of the present disclosure.

Figure 14:
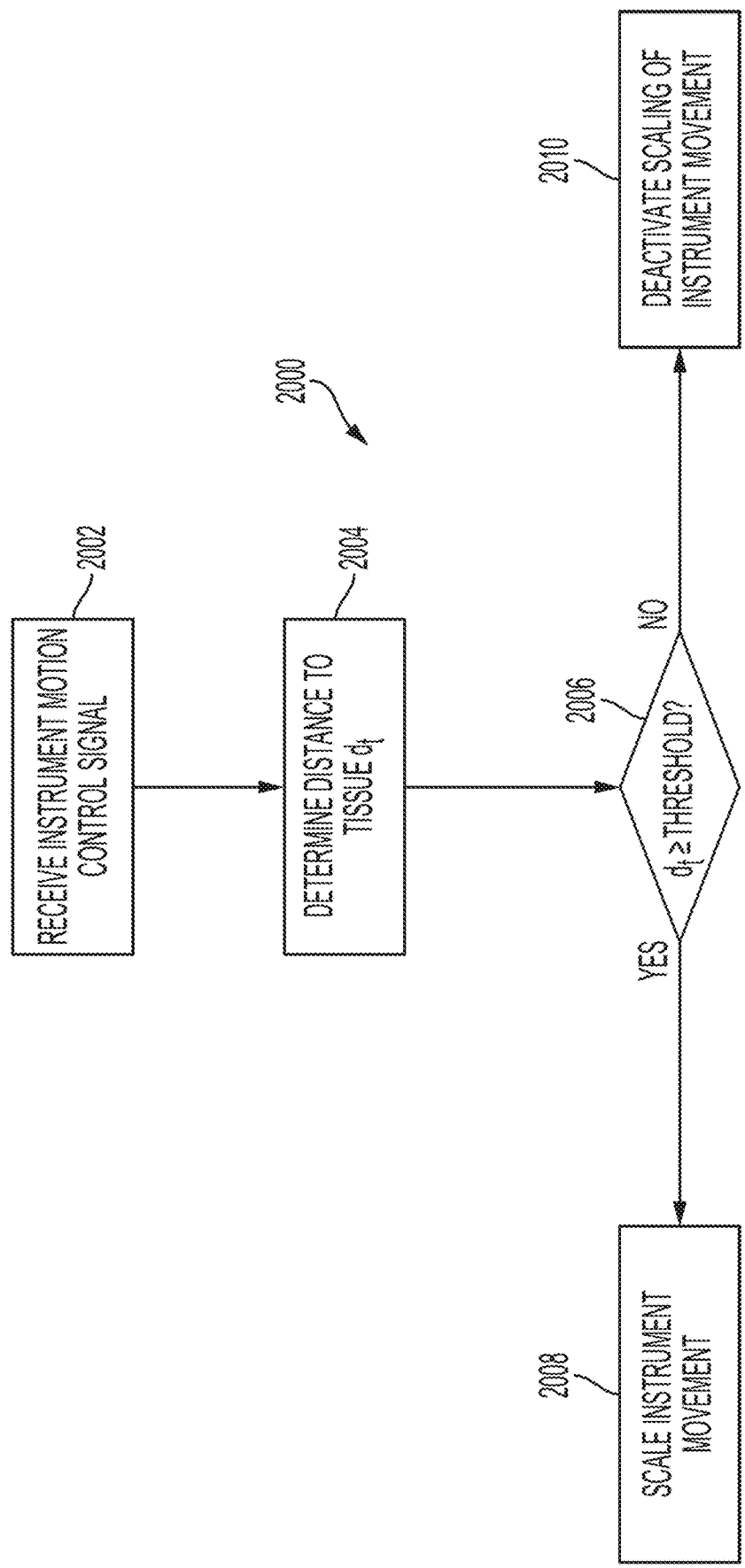

FIG. 14 is a logic flow diagram of a process for controlling the movement of a robotic surgical system, in accordance with at least one aspect of the present disclosure.

Figure 15:
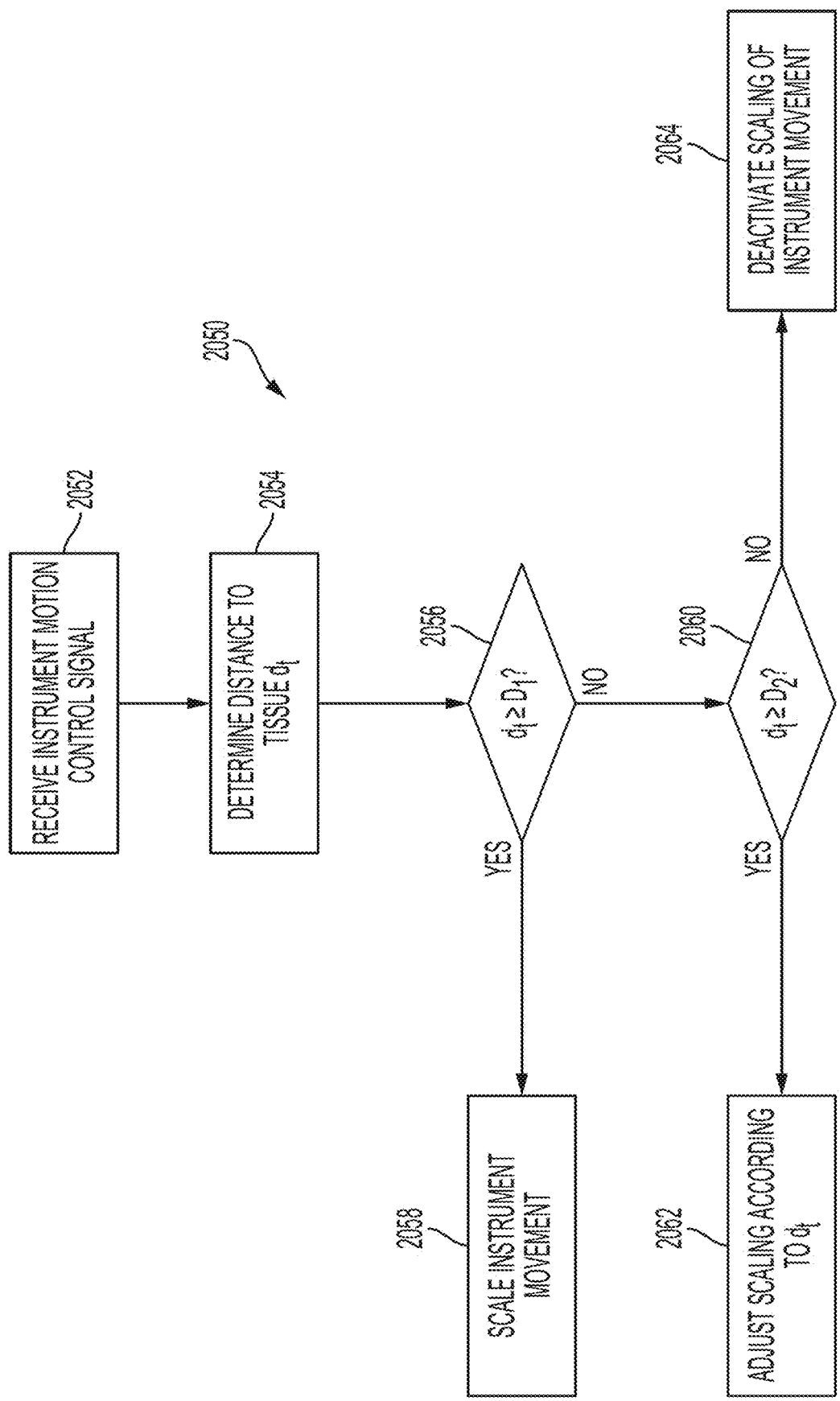

FIG. 15 is a logic flow diagram of a process for controlling the movement of a robotic surgical system, in accordance with at least one aspect of the present disclosure.

Figure 16:
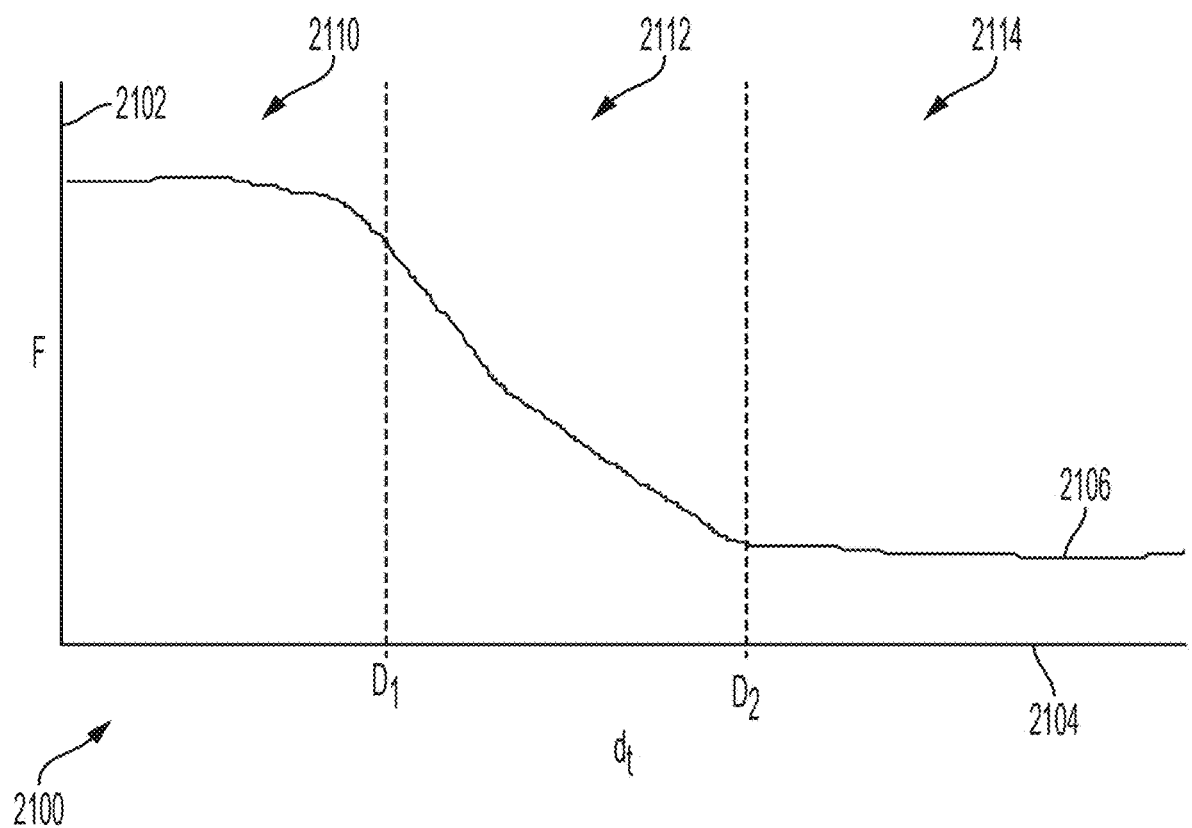

FIG. 16 is graph of the required force to be exerted on an input control device to move the robotic surgical system versus the proximity of a surgical tool end effector to a patient, in accordance with at least one aspect of the present disclosure.

Figure 17:
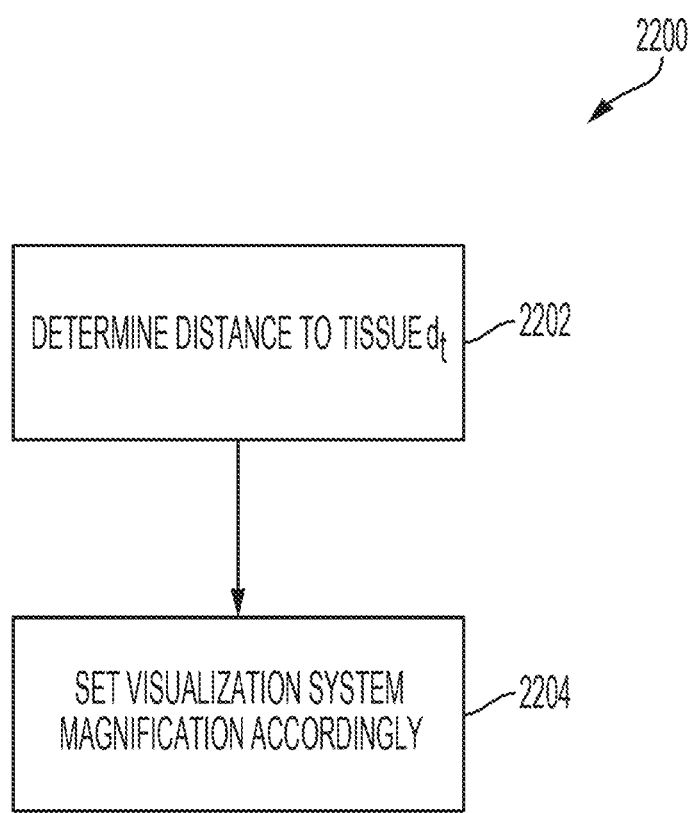

FIG. 17 is a logic flow diagram of a process for controlling a visualization system of a robotic surgical system, in accordance with at least one aspect of the present disclosure.

Figure 18:
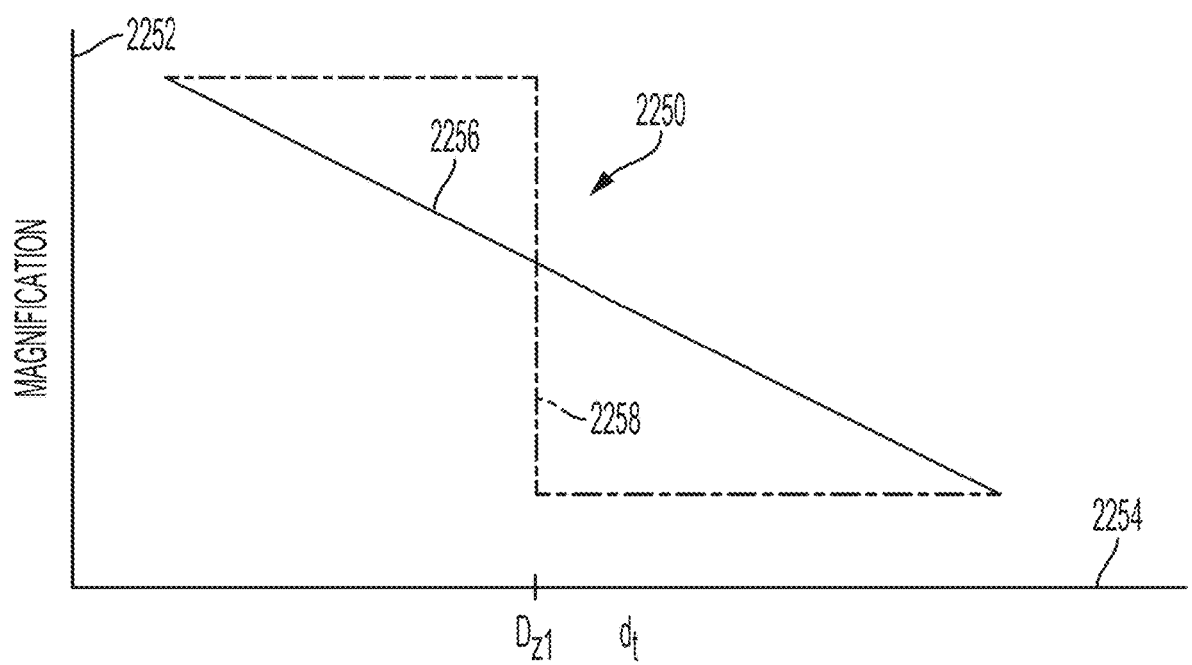

FIG. 18 is a graph of the magnification of the visualization system versus the distance between the robotic surgical system component and the patient, in accordance with at least one aspect of the present disclosure.

Figure 19:
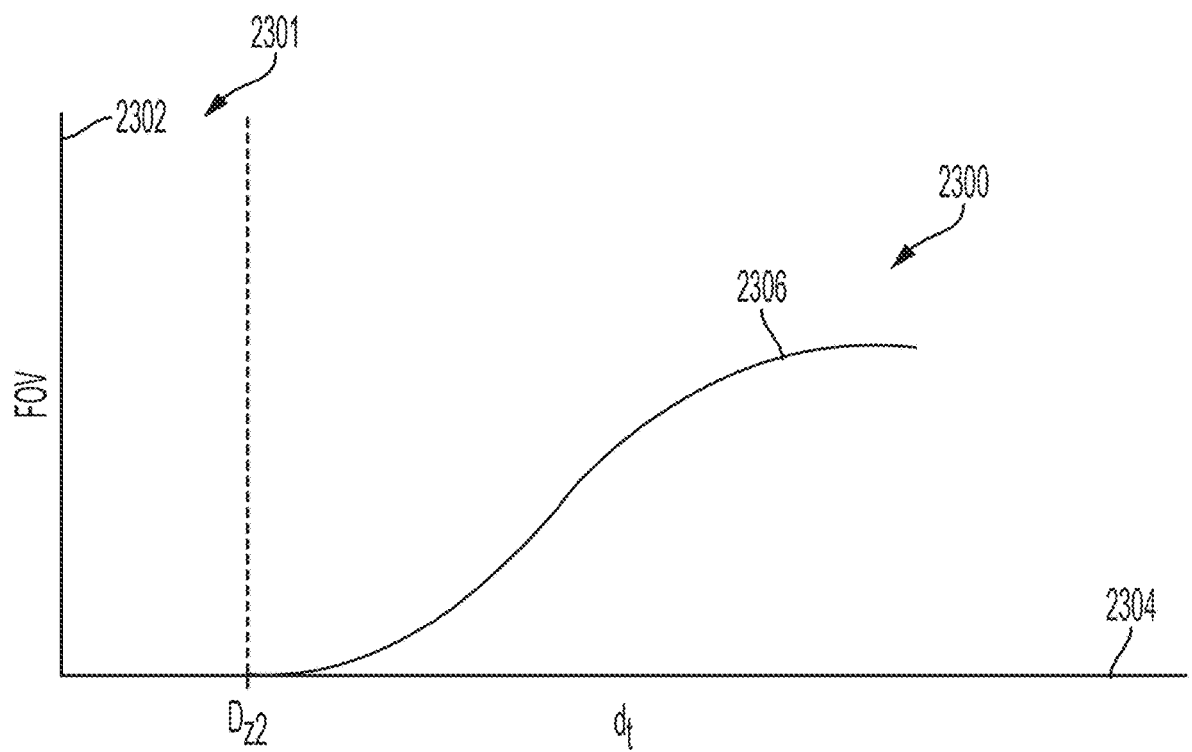

FIG. 19 is a graph of the field of view (FOV) of the visualization system versus the distance between the robotic surgical system component and the patient, in accordance with at least one aspect of the present disclosure.

Figure 20:
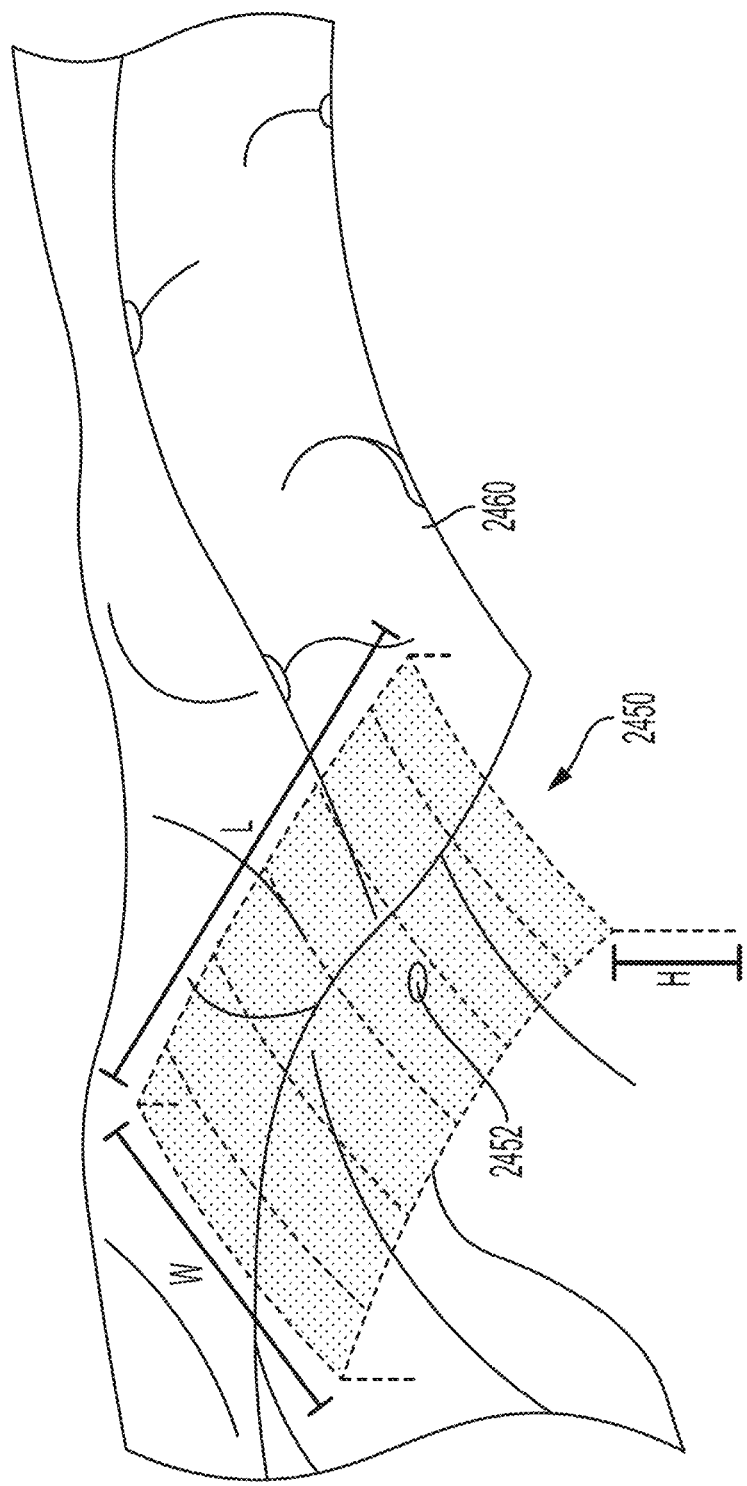

FIG. 20 is a perspective view of a robotic surgical system user interface for tagging locations, in accordance with at least one aspect of the present disclosure.

Figure 21:
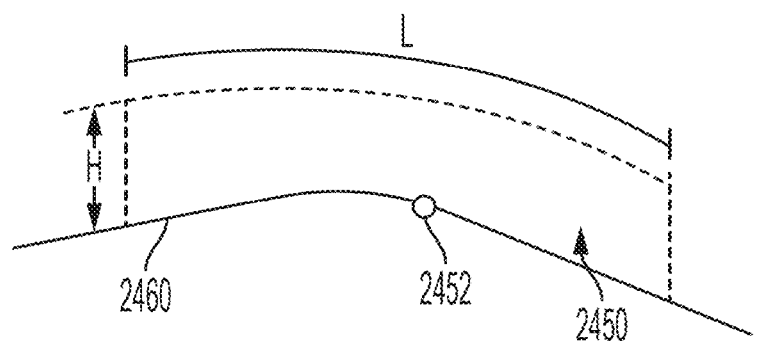

FIG. 21 is an elevational view of a tagged zone defined via the user interface, in accordance with at least one aspect of the present disclosure.

Figure 22:
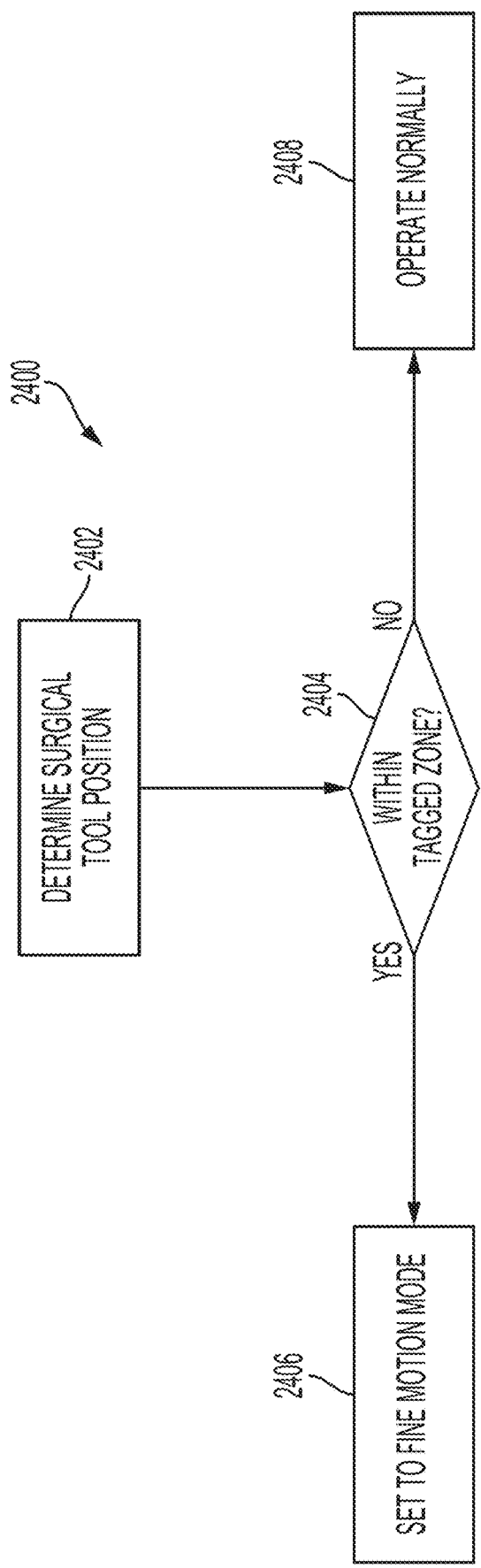

FIG. 22 is a logic flow diagram of a process for controlling a robotic surgical system according to whether a component thereof is positioned within a tagged zone, in accordance with at least one aspect of the present disclosure.

Figure 23:
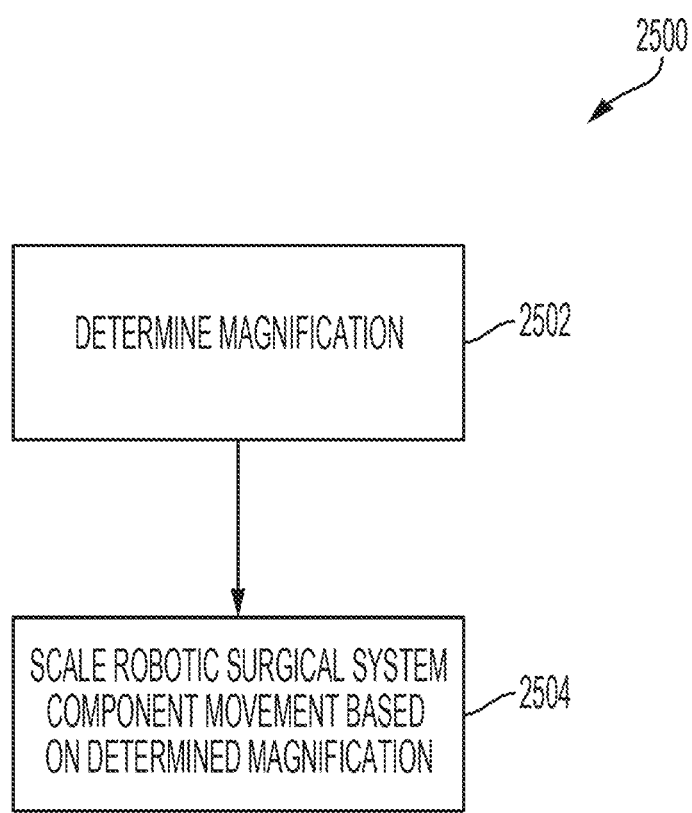

FIG. 23 is a logic flow diagram of a process for controlling the movement of a robotic surgical system according to camera magnification, in accordance with at least one aspect of the present disclosure.

Figure 24:
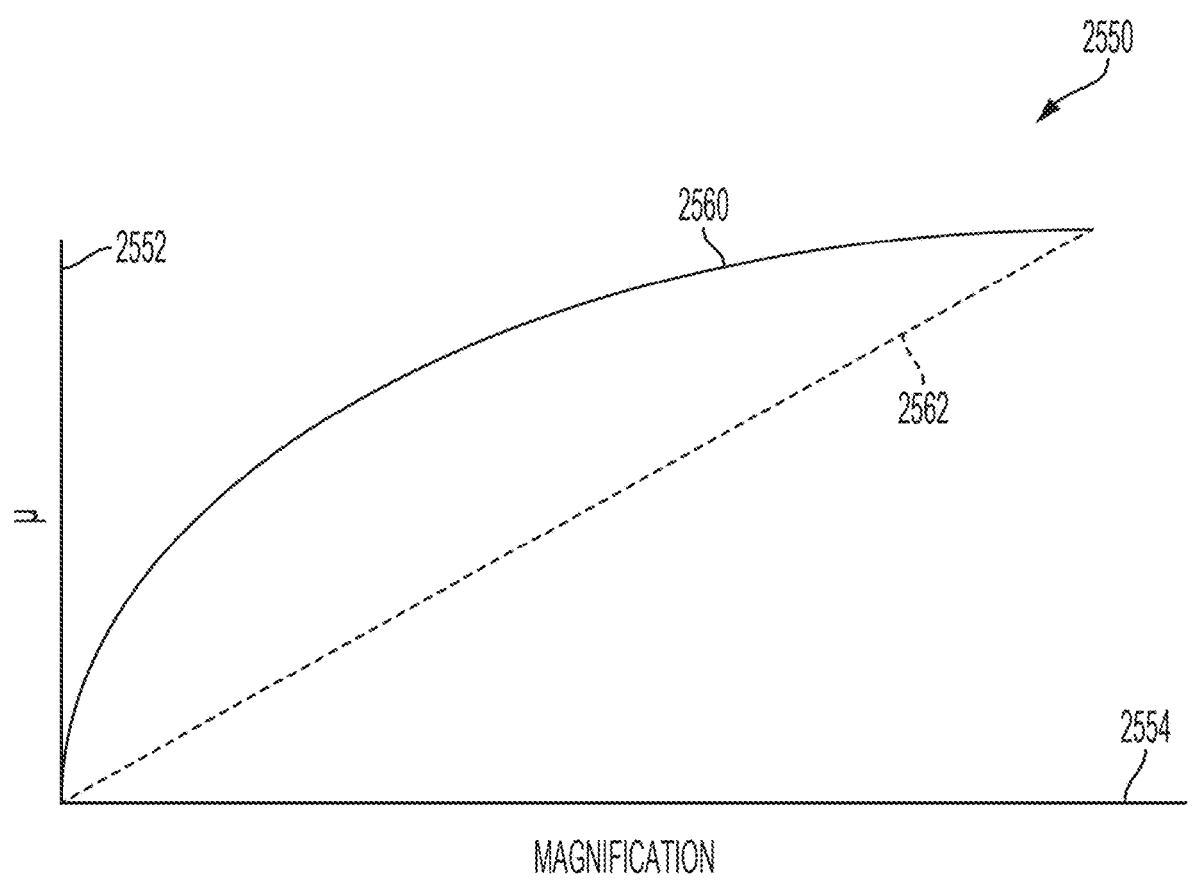

FIG. 24 is a graph of a robotic surgical system movement scale factor versus camera magnification, in accordance with at least one aspect of the present disclosure.

Figure 25:
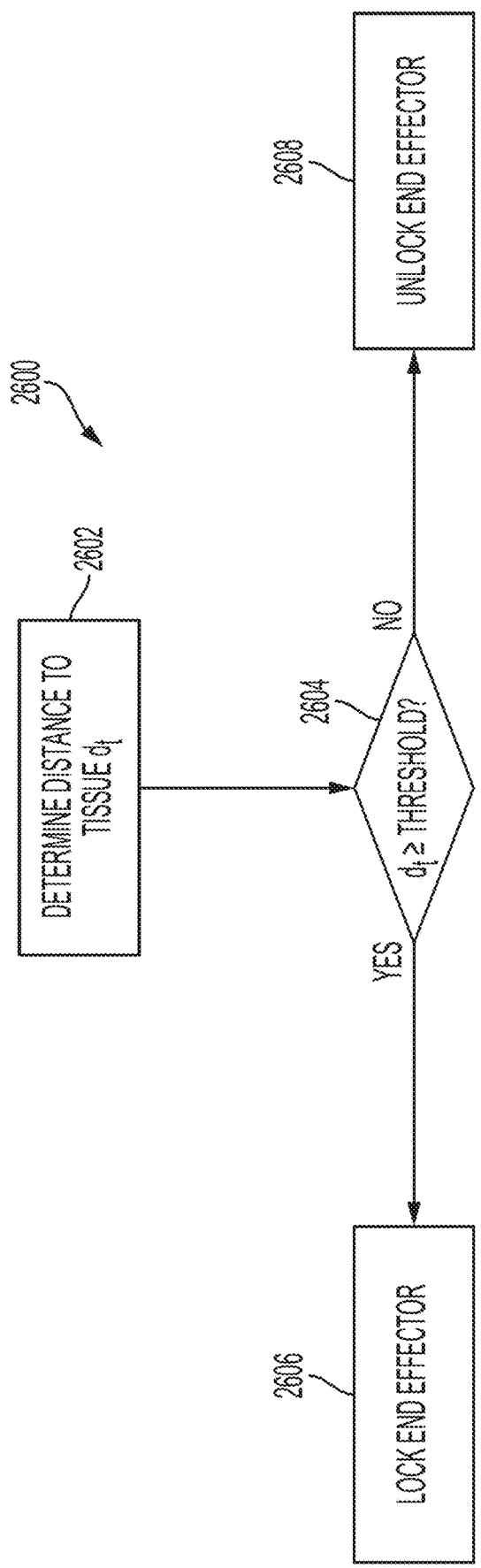

FIG. 25 is a logic flow diagram of a process for controlling an end effector, in accordance with at least one aspect of the present disclosure.

Figure 25A:
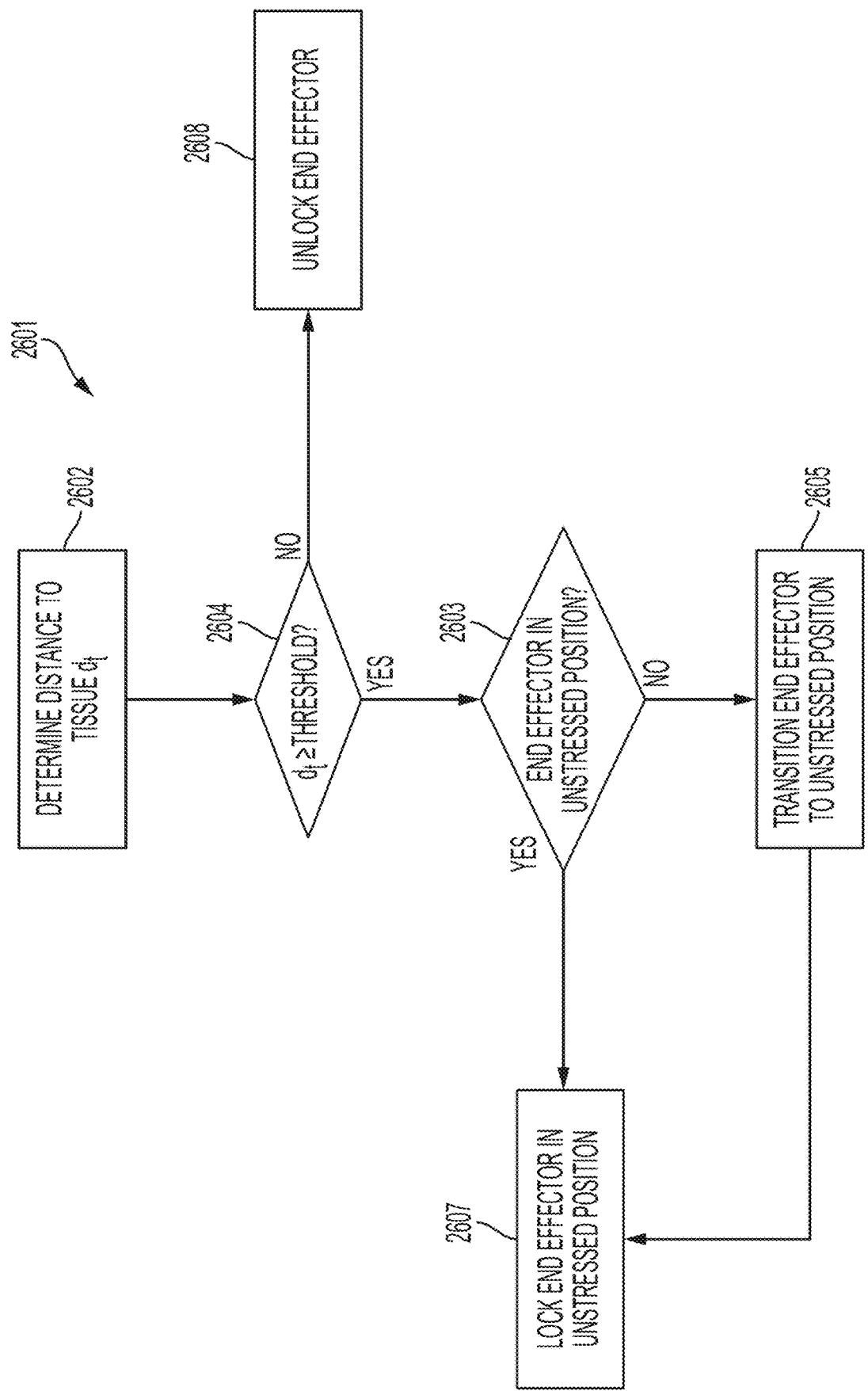

FIG. 25A is a logic flow diagram of a process for controlling an end effector, in accordance with at least one aspect of the present disclosure.

Figure 26:
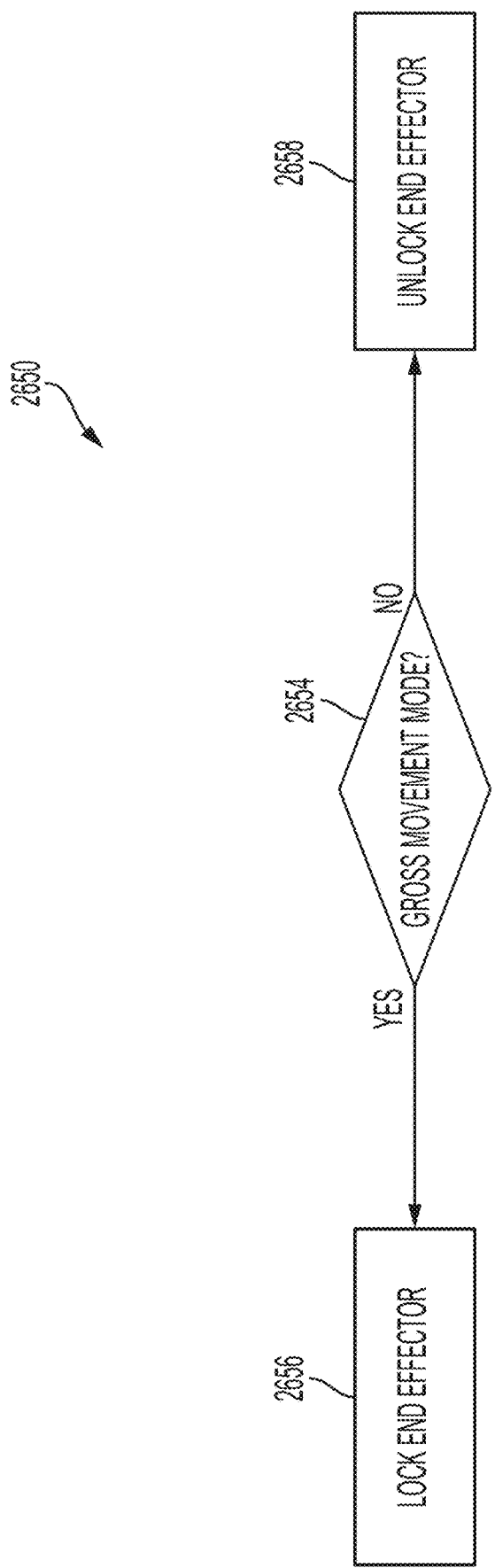

FIG. 26 is a logic flow diagram of a process for controlling an end effector, in accordance with at least one aspect of the present disclosure.

Figure 26A:
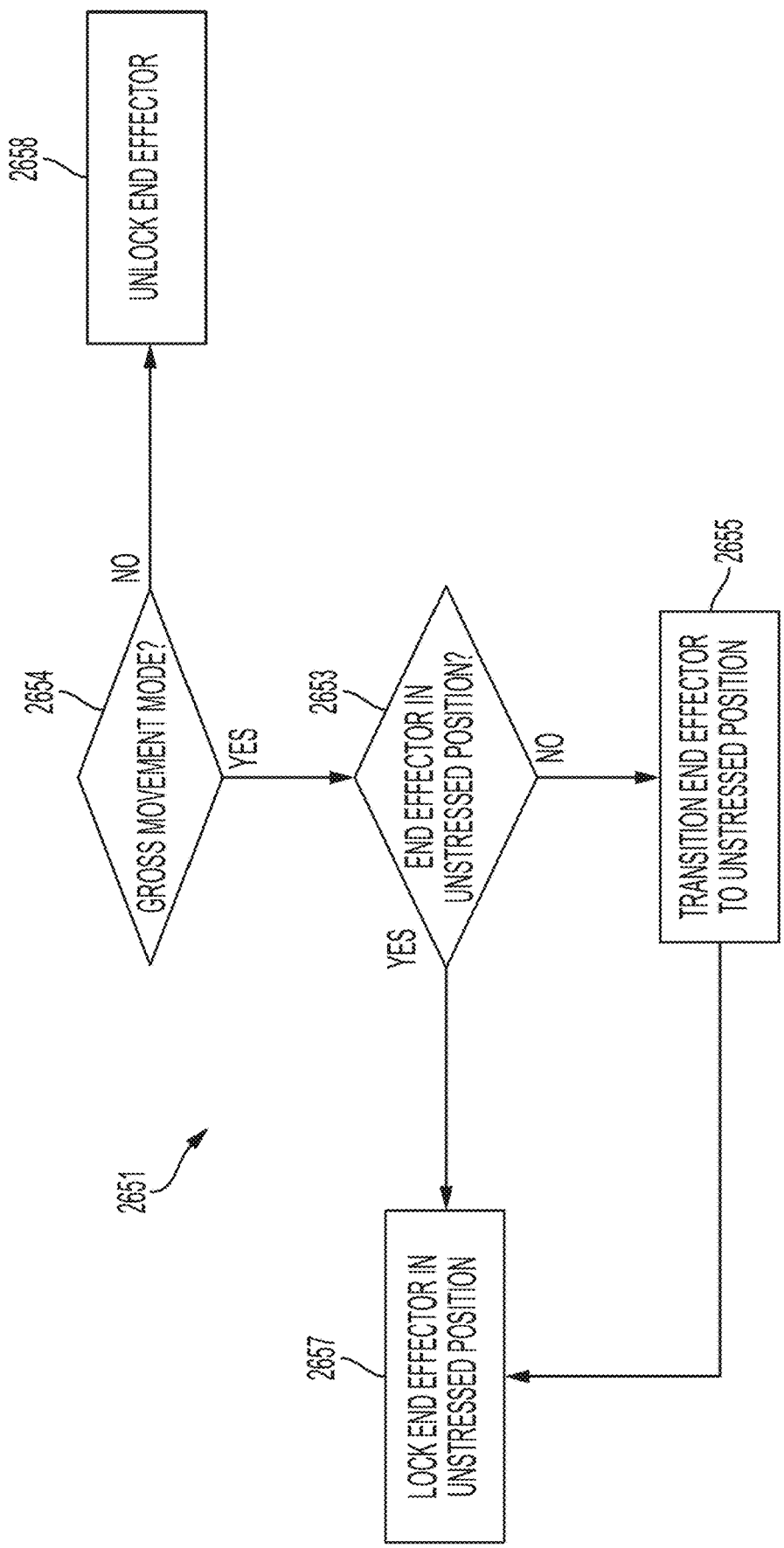

FIG. 26A is a logic flow diagram of a process for controlling an end effector, in accordance with at least one aspect of the present disclosure.

Figure 27:
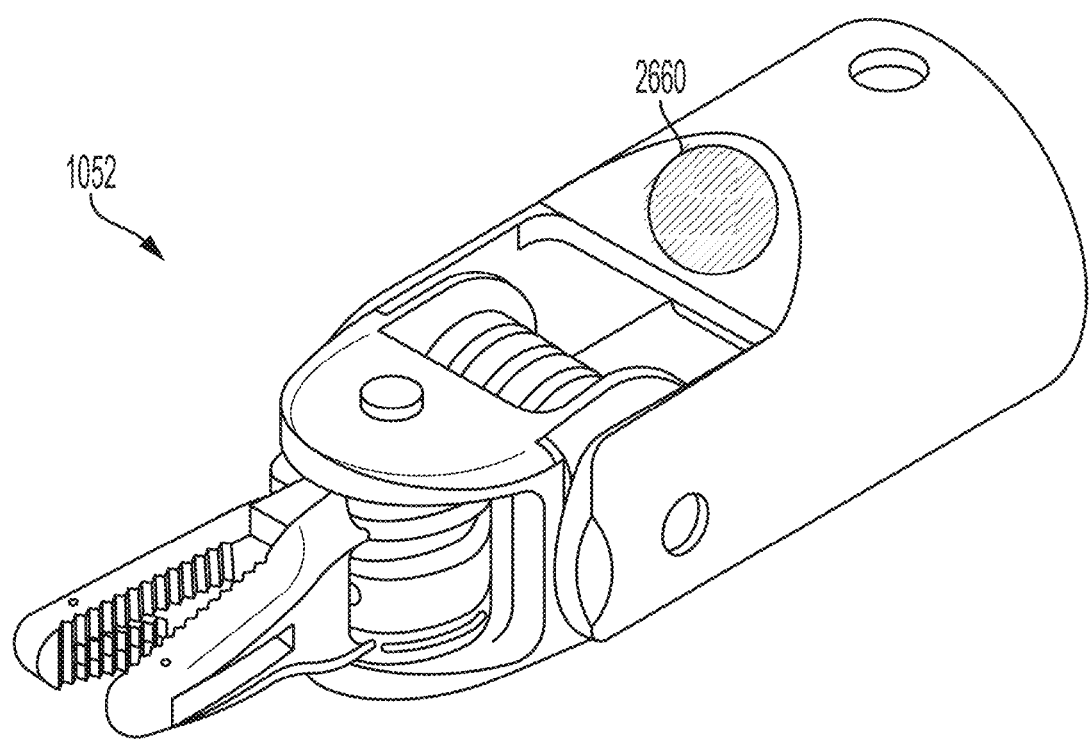

FIG. 27 is a perspective view of an end effector comprising an indicator configured to signal the lock state of the surgical tool, in accordance with at least one aspect of the present disclosure.

FIG. 28 is a graph illustrating four motion scaling profiles, in accordance with at least one aspect of the present disclosure.

FIG. 29 is a motion scaling profile selector, in accordance with at least one aspect of the present disclosure.

FIG. 30 is a lookup table stored in a memory, in accordance with at least one aspect of the present disclosure.

FIG. 31 is pedal assembly, in accordance with at least one aspect of the present disclosure.

Figure 32:
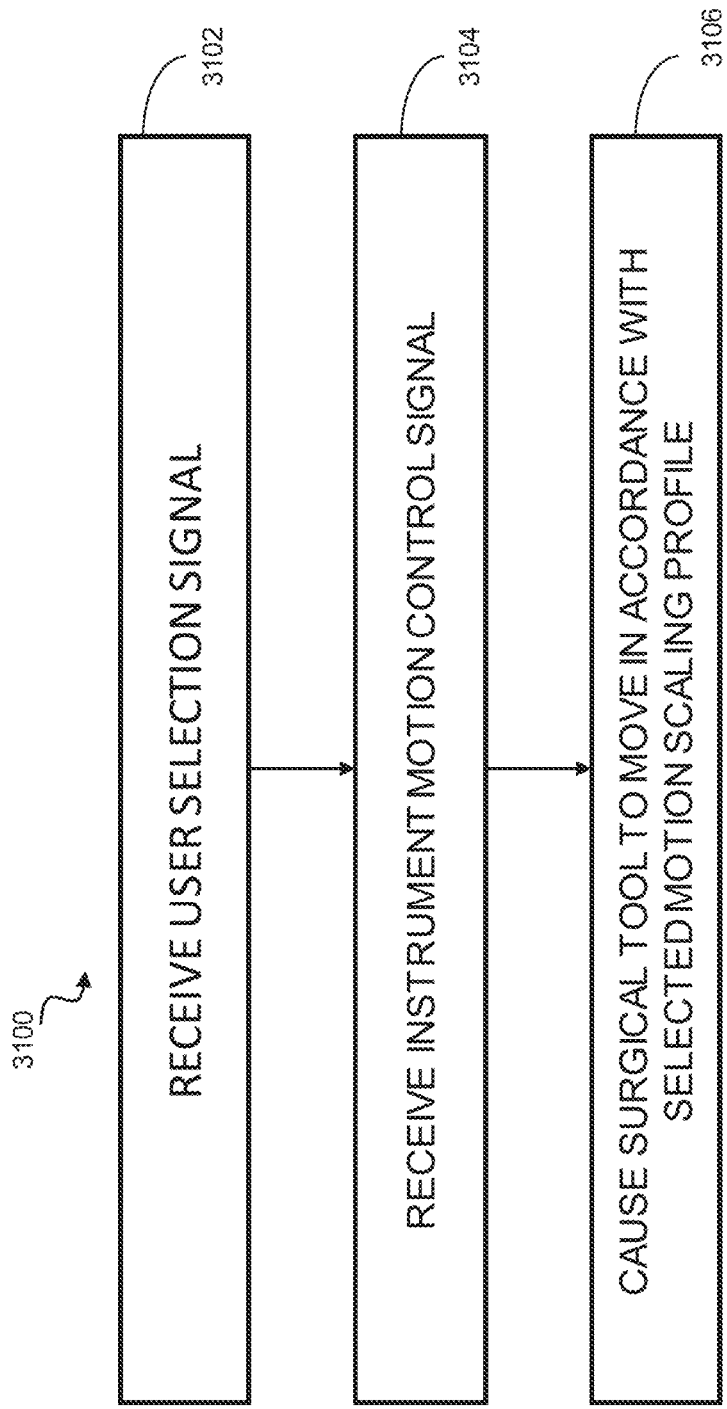

FIG. 32 is a logic flow diagram of a process for selecting between motion scaling profiles for a surgical tool, in accordance with at least one aspect of the present disclosure.

Figure 33:
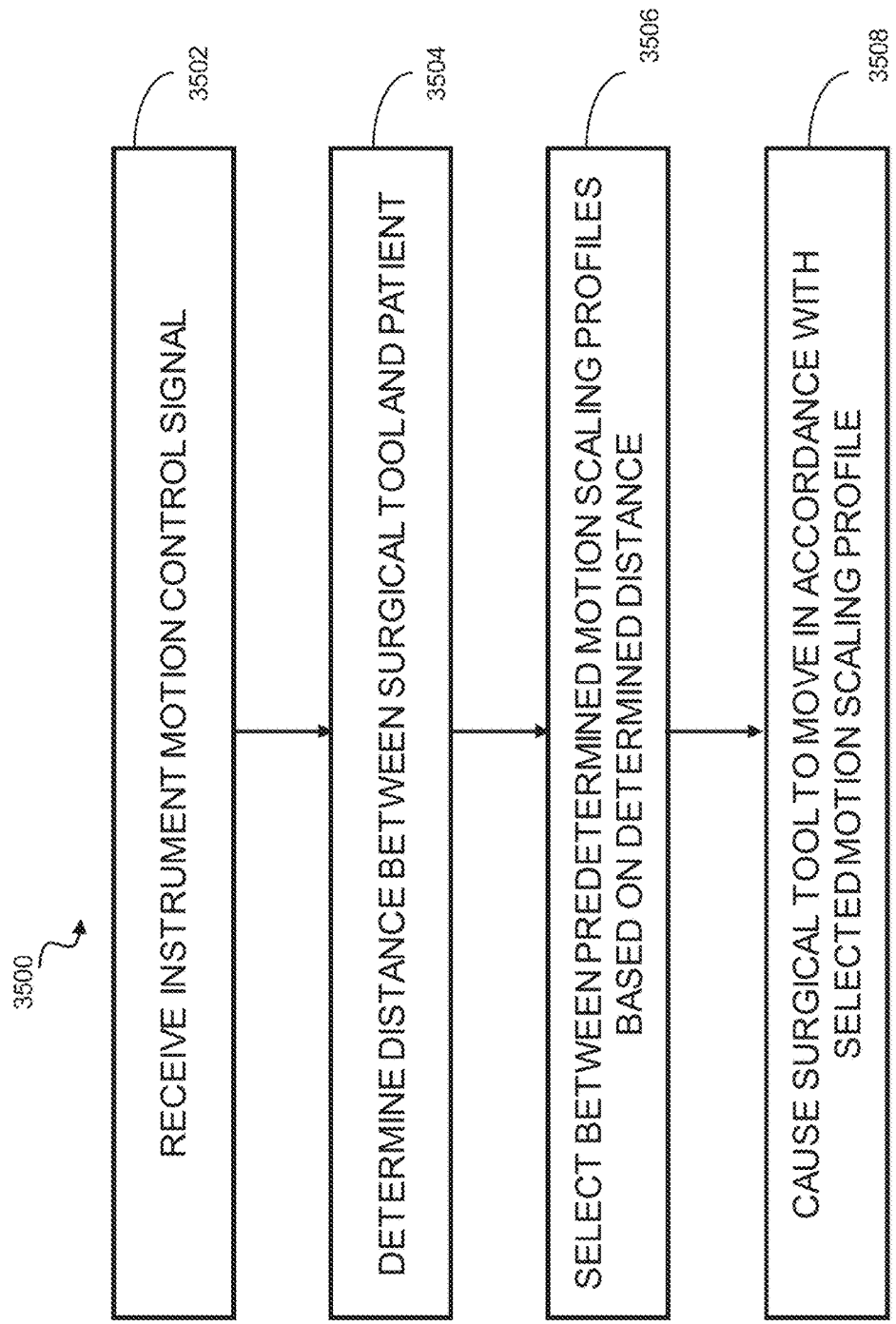

FIG. 33 is a logic flow diagram of a process for selecting between motion scaling profiles for a surgical tool, in accordance with at least one aspect of the present disclosure.

Figure 34:
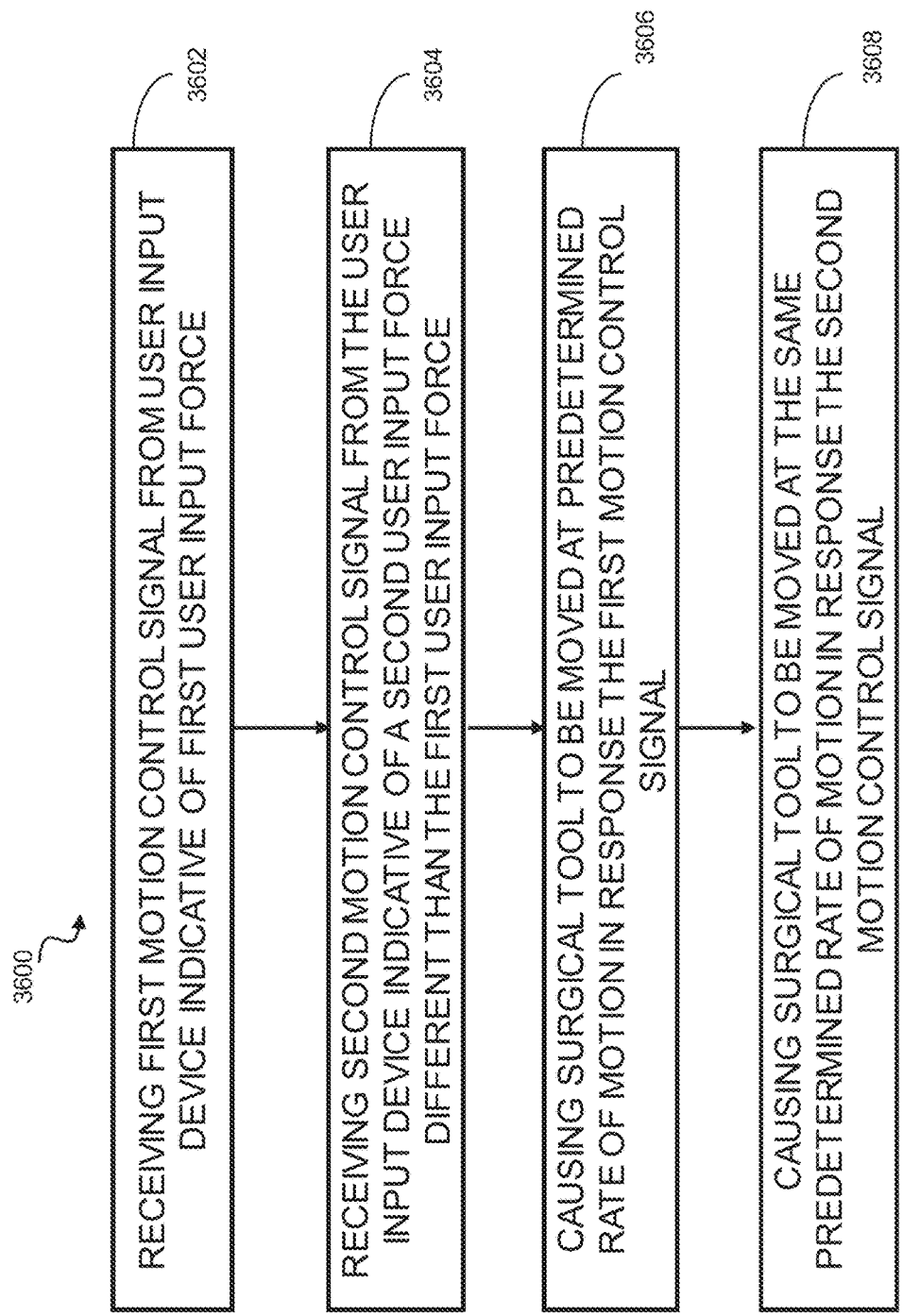

FIG. 34 is a logic flow diagram of a process for selecting between motion scaling profiles for a surgical tool, in accordance with at least one aspect of the present disclosure.

DESCRIPTION

Applicant of the present application owns the following U.S. Patent Applications, filed on Mar. 15, 2019, each of which is herein incorporated by reference in its entirety:
- U.S. patent application Ser. No. 16/354,417, titled INPUT CONTROLS FOR ROBOTIC SURGERY, now U.S. Patent Application Publication No. 2020/0289219;
- U.S. patent application Ser. No. 16/354,420, titled DUAL MODE CONTROLS FOR ROBOTIC SURGERY, now U.S. Patent Application Publication No. 2020/0289228;
- U.S. patent application Ser. No. 16/354,422, titled MOTION CAPTURE CONTROLS FOR ROBOTIC SURGERY, now U.S. Patent Application Publication No. 2020/289216;
- U.S. patent application Ser. No. 16/354,444, titled ROBOTIC SURGICAL SYSTEMS WITH MECHANISMS FOR SCALING CAMERA MAGNIFICATION ACCORDING TO PROXIMITY OF SURGICAL TOOL TO TISSUE, now U.S. Patent Application Publication No. 2020/0289205;
- U.S. patent application Ser. No. 16/354,454, titled ROBOTIC SURGICAL SYSTEMS WITH SELECTIVELY LOCKABLE END EFFECTORS, now U.S. Patent Application Publication No. 2020/0289221;
- U.S. patent application Ser. No. 16/354,461, titled Selectable Variable response of shaft motion of surgical robotic systems, now U.S. Patent Application Publication No. 2020/0289222;
- U.S. patent application Ser. No. 16/354,470, titled SEGMENTED CONTROL INPUTS FOR SURGICAL ROBOTIC SYSTEMS, now U.S. Patent Application Publication No. 2020/0289223;
- U.S. patent application Ser. No. 16/354,474, titled ROBOTIC SURGICAL CONTROLS HAVING FEEDBACK CAPABILITIES, now U.S. Patent Application Publication No. 2020/0289229;
- U.S. patent application Ser. No. 16/354,478, titled ROBOTIC SURGICAL CONTROLS WITH FORCE FEEDBACK, now U.S. Patent Application Publication No. 2020/0289230; and
- U.S. patent application Ser. No. 16/354,481, titled JAW COORDINATION OF ROBOTIC SURGICAL CONTROLS, now U.S. Patent Application Publication No. 2020/0289217.

Applicant of the present application also owns the following U.S. Patent Applications, filed on Sep. 11, 2018, each of which is herein incorporated by reference in its entirety:
- U.S. patent application Ser. No. 16/128,179, titled SURGICAL VISUALIZATION PLATFORM;
- U.S. patent application Ser. No. 16/128,180, titled CONTROLLING AN EMITTER ASSEMBLY PULSE SEQUENCE;
- U.S. patent application Ser. No. 16/128,198, titled SINGULAR EMR SOURCE EMITTER ASSEMBLY;
- U.S. patent application Ser. No. 16/128,207, titled COMBINATION EMITTER AND CAMERA ASSEMBLY;
- U.S. patent application Ser. No. 16/128,176, titled SURGICAL VISUALIZATION WITH PROXIMITY TRACKING FEATURES;
- U.S. patent application Ser. No. 16/128,187, titled SURGICAL VISUALIZATION OF MULTIPLE TARGETS;
- U.S. patent application Ser. No. 16/128,192, titled VISUALIZATION OF SURGICAL DEVICES;
- U.S. patent application Ser. No. 16/128,163, titled OPERATIVE COMMUNICATION OF LIGHT;
- U.S. patent application Ser. No. 16/128,197, titled ROBOTIC LIGHT PROJECTION TOOLS;
- U.S. patent application Ser. No. 16/128,164, titled SURGICAL VISUALIZATION FEEDBACK SYSTEM;
- U.S. patent application Ser. No. 16/128,193, titled SURGICAL VISUALIZATION AND MONITORING;
- U.S. patent application Ser. No. 16/128,195, titled INTEGRATION OF IMAGING DATA;
- U.S. patent application Ser. No. 16/128,170, titled ROBOTICALLY-ASSISTED SURGICAL SUTURING SYSTEMS;
- U.S. patent application Ser. No. 16/128,183, titled SAFETY LOGIC FOR SURGICAL SUTURING SYSTEMS;
- U.S. patent application Ser. No. 16/128,172, titled ROBOTIC SYSTEM WITH SEPARATE PHOTOACOUSTIC RECEIVER; and
- U.S. patent application Ser. No. 16/128,185, titled FORCE SENSOR THROUGH STRUCTURED LIGHT DEFLECTION.

Applicant of the present application also owns the following U.S. Patent Applications, filed on Mar. 29, 2018, each of which is herein incorporated by reference in its entirety:
- U.S. patent application Ser. No. 15/940,627, titled DRIVE ARRANGEMENTS FOR ROBOT-ASSISTED SURGICAL PLATFORMS;
- U.S. patent application Ser. No. 15/940,676, titled AUTOMATIC TOOL ADJUSTMENTS FOR ROBOT-ASSISTED SURGICAL PLATFORMS;
- U.S. patent application Ser. No. 15/940,711, titled SENSING ARRANGEMENTS FOR ROBOT-ASSISTED SURGICAL PLATFORMS; and
- U.S. patent application Ser. No. 15/940,722, titled CHARACTERIZATION OF TISSUE IRREGULARITIES THROUGH THE USE OF MONO-CHROMATIC LIGHT REFRACTIVITY.

Before explaining various aspects of a robotic surgical platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Before explaining various aspects of a robotic surgical platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Robotic Systems

Figure 1:
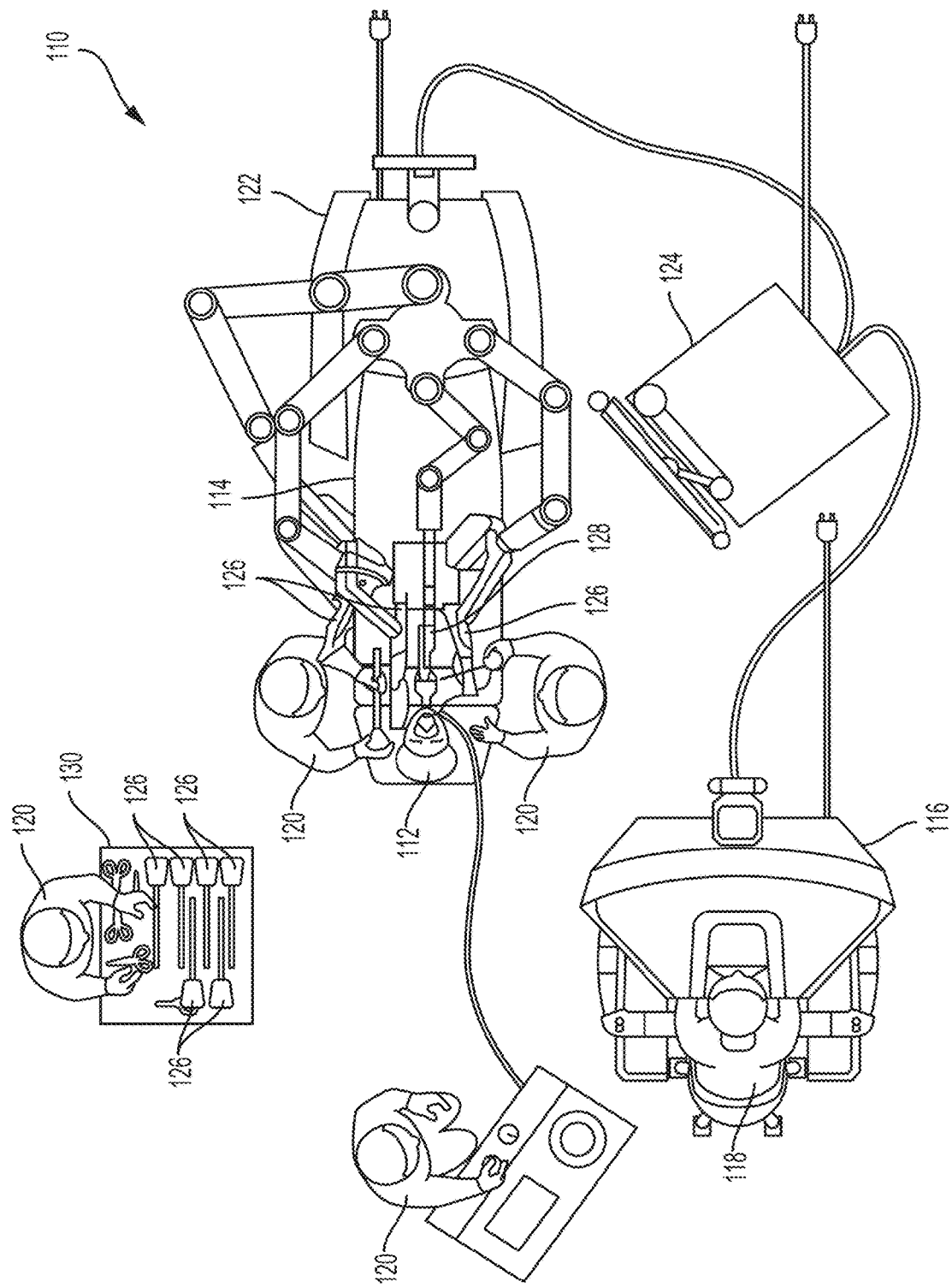
FIG. 1 is a plan view of a robotic surgical system being used to perform a surgery, according to at least one aspect of the present disclosure.

An exemplary robotic system 110 is depicted in FIG. 1. The robotic system 110 is a minimally invasive robotic surgical (MIRS) system typically used for performing a minimally invasive diagnostic or surgical procedure on a patient 112 who is lying down on an operating table 114. The robotic system 110 includes a surgeon's console 116 for use by a surgeon 118 during the procedure. One or more assistants 120 may also participate in the procedure. The robotic system 110 can further include a patient side cart 122, i.e. a surgical robot, and an electronics cart 124. The surgical robot 122 can manipulate at least one removably coupled tool assembly 126 (hereinafter referred to as a "tool") through a minimally invasive incision in the body of the patient 112 while the surgeon 118 views the surgical site through the console 116. An image of the surgical site can be obtained by an imaging device such as a stereoscopic endoscope 128, which can be manipulated by the surgical robot 122 to orient the endoscope 128. Alternative imaging devices are also contemplated.

The electronics cart 124 can be used to process the images of the surgical site for subsequent display to the surgeon 118 through the surgeon's console 116. In certain instances, the electronics of the electronics cart 124 can be incorporated into another structure in the operating room, such as the operating table 114, the surgical robot 122, the surgeon's console 116, and/or another control station, for example. The number of robotic tools 126 used at one time will generally depend on the diagnostic or surgical procedure and the space constraints within the operating room among other factors. If it is necessary to change one or more of the robotic tools 126 being used during a procedure, an assistant 120 may remove the robotic tool 126 from the surgical robot 122 and replace it with another tool 126 from a tray 130 in the operating room.

Figure 2:
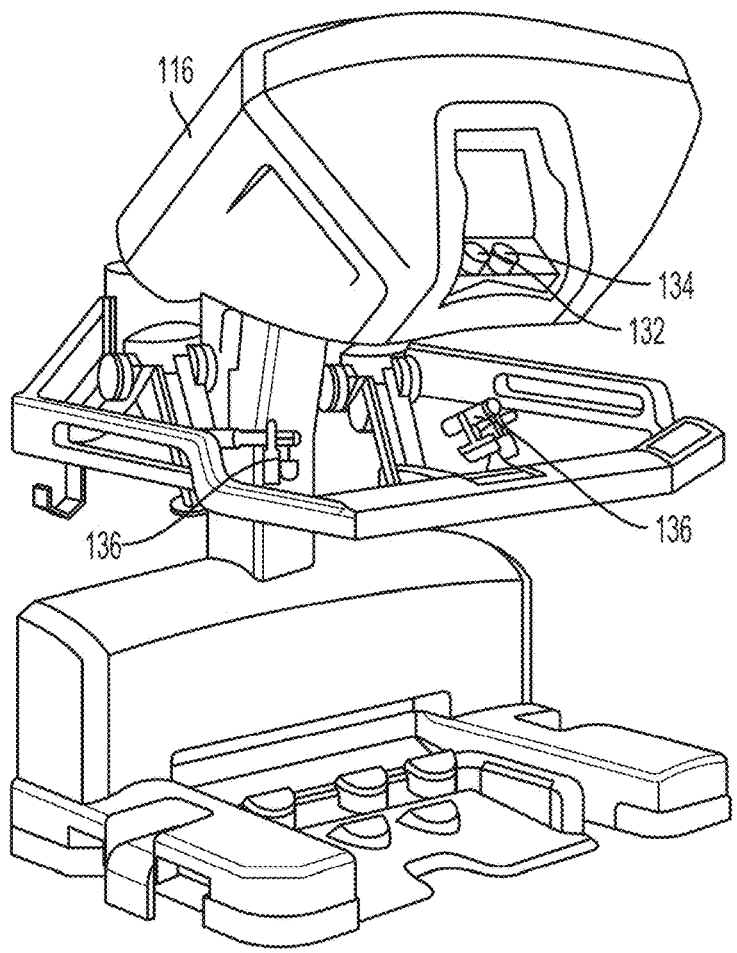
FIG. 2 is a perspective view of a surgeon's control console of the robotic surgical system of FIG. 1, according to at least one aspect of the present disclosure.

Referring primarily to FIG. 2, the surgeon's console 116 includes a left eye display 132 and a right eye display 134 for presenting the surgeon 118 with a coordinated stereo view of the surgical site that enables depth perception. The console 116 further includes one or more input control devices 136, which in turn cause the surgical robot 122 to manipulate one or more tools 126. The input control devices 136 can provide the same degrees of freedom as their associated tools 126 to provide the surgeon with telepresence, or the perception that the input control devices 136 are integral with the robotic tools 126 so that the surgeon has a strong sense of directly controlling the robotic tools 126. To this end, position, force, and tactile feedback sensors may be employed to transmit position, force, and tactile sensations from the robotic tools 126 back to the surgeon's hands through the input control devices 136. The surgeon's console 116 can be located in the same room as the patient 112 so that the surgeon 118 may directly monitor the procedure, be physically present if necessary, and speak to an assistant 120 directly rather than over the telephone or other communication medium. However, the surgeon 118 can be located in a different room, a completely different building, or other remote location from the patient 112 allowing for remote surgical procedures. A sterile field can be defined around the surgical site. In various instances, the surgeon 118 can be positioned outside the sterile field.

Referring again to FIG. 1, the electronics cart 124 can be coupled with the endoscope 128 and can include a processor to process captured images for subsequent display, such as to a surgeon on the surgeon's console 116, or on another suitable display located locally and/or remotely. For example, when the stereoscopic endoscope 128 is used, the electronics cart 124 can process the captured images to present the surgeon with coordinated stereo images of the surgical site. Such coordination can include alignment between the opposing images and can include adjusting the stereo working distance of the stereoscopic endoscope. As another example, image processing can include the use of previously-determined camera calibration parameters to compensate for imaging errors of the image capture device, such as optical aberrations, for example. In various instances, the robotic system 110 can incorporate a surgical visualization system, as further described herein, such that an augmented view of the surgical site that includes hidden critical structures, three-dimensional topography, and/or one or more distances can be conveyed to the surgeon at the surgeon's console 116.

Figure 3:
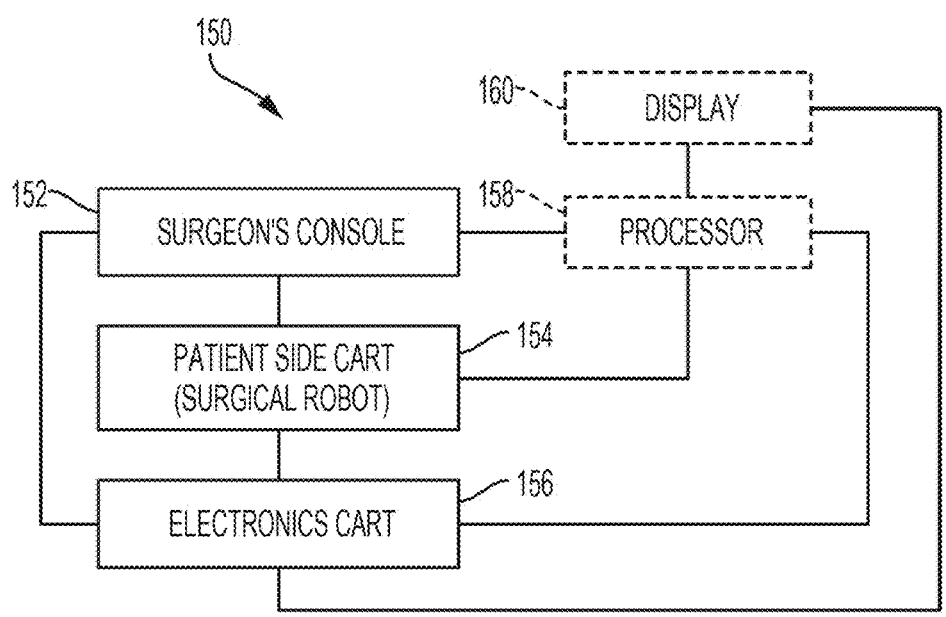
FIG. 3 is a diagram of a robotic surgical system, according to at least one aspect of the present disclosure.

FIG. 3 diagrammatically illustrates a robotic surgery system 150, such as the MIRS system 110 (FIG. 1). As discussed herein, a surgeon's console 152, such as the surgeon's console 116 (FIGS. 1 and 2), can be used by a surgeon to control a surgical robot 154, such as the surgical robot 122 (FIG. 1), during a minimally invasive procedure. The surgical robot 154 can use an imaging device, such as a stereoscopic endoscope, for example, to capture images of the surgical site and output the captured images to an electronics cart 156, such as the electronics cart 124 (FIG. 1). As discussed herein, the electronics cart 156 can process the captured images in a variety of ways prior to any subsequent display. For example, the electronics cart 156 can overlay the captured images with a virtual control interface prior to displaying the combined images to the surgeon via the surgeon's console 152. The surgical robot 154 can output the captured images for processing outside the electronics cart 156. For example, the surgical robot 154 can output the captured images to a processor 158, which can be used to process the captured images. The images can also be processed by a combination of the electronics cart 156 and the processor 158, which can be coupled together to process the captured images jointly, sequentially, and/or combinations thereof. One or more separate displays 160 can also be coupled with the processor 158 and/or the electronics cart 156 for local and/or remote display of images, such as images of the surgical site, or other related images.

The reader will appreciate that various robotic tools can be employed with the surgical robot 122 and exemplary robotic tools are described herein. Referring again to FIG. 1, the surgical robot 122 shown provides for the manipulation of three robotic tools 126 and the imaging device 128, such as a stereoscopic endoscope used for the capture of images of the site of the procedure, for example. Manipulation is provided by robotic mechanisms having a number of robotic joints. The imaging device 128 and the robotic tools 126 can be positioned and manipulated through incisions in the patient so that a kinematic remote center or virtual pivot is maintained at the incision to minimize the size of the incision. Images of the surgical site can include images of the distal ends of the robotic tools 126 when they are positioned within the field-of-view (FOV) of the imaging device 128. Each tool 126 is detachable from and carried by a respective surgical manipulator, which is located at the distal end of one or more of the robotic joints. The surgical manipulator provides a moveable platform for moving the entirety of a tool 126 with respect to the surgical robot 122, via movement of the robotic joints. The surgical manipulator also provides power to operate the robotic tool 126 using one or more mechanical and/or electrical interfaces. In various instances, one or more motors can be housed in the surgical manipulator for generating controls motions. One or more transmissions can be employed to selectively couple the motors to various actuation systems in the robotic tool.

The foregoing robotic systems are further described in U.S. patent application Ser. No. 15/940,627, titled DRIVE ARRANGEMENTS FOR ROBOT-ASSISTED SURGICAL PLATFORMS, filed Mar. 29, 2018, which is incorporated by reference herein in its entirety. Alternative robotic systems are also contemplated.

Figure 4:
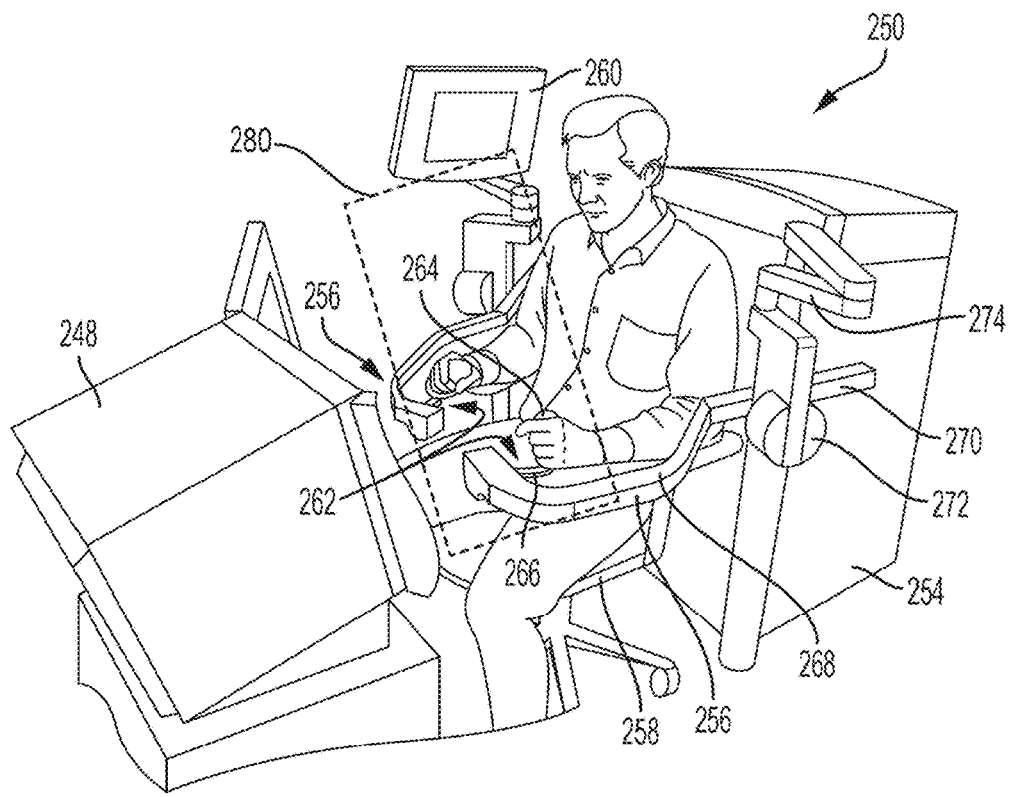
FIG. 4 is a perspective view of a surgeon's control console of a robotic surgical system, according to at least one aspect of the present disclosure.

Referring now to FIG. 4, a surgeon's console, or control unit, 250 is shown. The surgeon's console 250 can be used in connection with a robotic system to control any two surgical tools coupled to the robotic system. The surgical tools can be controlled by the handle assemblies 256 of the surgeon's console 250. For example, the handle assemblies 256 and robotic arms have a master-slave relationship so that movement of the handle assemblies 256 produces a corresponding movement of the surgical tools. A controller 254 receives input signals from the handle assemblies 256, computes a corresponding movement of the surgical tools, and provides output signals to move the robotic arms and the surgical tools.

The handle assemblies 256 are located adjacent to a surgeon's chair 258 and coupled to the controller 254. The controller 254 may include one or more microprocessors, memory devices, drivers, etc. that convert input information from the handle assemblies 256 into output control signals which move the robotic arms and/or actuate the surgical tools. The surgeon's chair 258 and the handle assemblies 256 may be in front of a video console 248, which can be linked to an endoscope to provide video images of the patient. The surgeon's console 250 may also include a screen 260 coupled to the controller 254. The screen 260 may display graphical user interfaces (GUIs) that allow the surgeon to control various functions and parameters of the robotic system.

Each handle assembly 256 includes a handle/wrist assembly 262. The handle/wrist assembly 262 has a handle 264 that is coupled to a wrist 266. The wrist 266 is connected to a forearm linkage 268 that slides along a slide bar 270. The slide bar 270 is pivotally connected to an elbow joint 272. The elbow joint 272 is pivotally connected to a shoulder joint 274 that is attached to the controller 254. The surgeon sitting at the surgeon's console 250 can provide input control motions to the handle assemblies 256 to effect movements and/or actuations of a surgical tool communicatively coupled thereto. For example, the surgeon can advance the forearm linkage 268 along the slide bar 270 to advance the surgical tool toward a surgical site. Rotations at the wrist 266, elbow joint 272, and/or shoulder joint 274 can effect rotation and/or articulation of the surgical tool about the corresponding axes. The robotic system and surgeon's console 250 are further described in U.S. Pat. No. 6,951,535, titled TELE-MEDICINE SYSTEM THAT TRANSMITS AN ENTIRE STATE OF A SUBSYSTEM, which issued Oct. 4, 2005, the entire disclosure of which is incorporated by reference herein.

Figure 5:
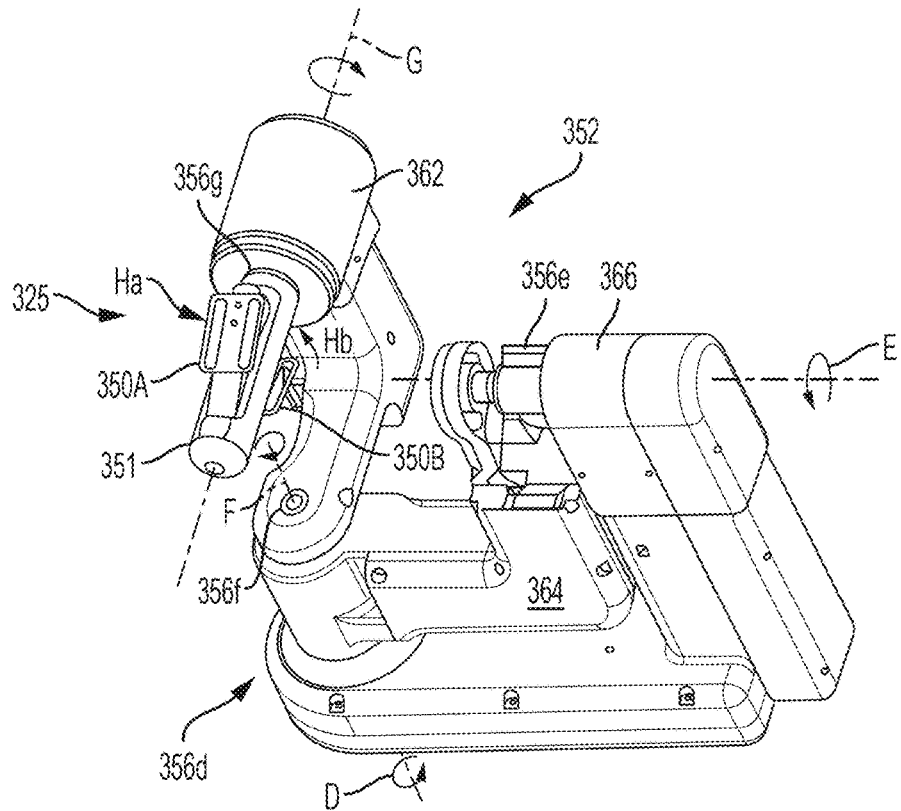
FIG. 5 is a perspective view of an input control device at a surgeon's control console, according to at least one aspect of the present disclosure.

A handle assembly for use at a surgeon's console is further depicted in FIG. 5. The handle assembly of FIG. 5 includes a control input wrist 352 and a touch sensitive handle 325. The control input wrist 352 is a gimbaled device that pivotally supports the touch sensitive handle 325 to generate control signals that are used to control a robotic surgical manipulator and the robotic surgical tools. A pair of control input wrists 352 and touch sensitive handles 325 can be supported by a pair of control input arms in a workspace of the surgeon's console.

The control input wrist 352 includes first, second, and third gimbal members 362, 364, and 366, respectively. The third gimbal member 366 can be rotationally mounted to a control input arm. The touch sensitive handle 325 include a tubular support structure 351, a first grip 350A, and a second grip 350B. The first grip 350A and the second grip 350B are supported at one end by the tubular support structure 351. The touch sensitive handle 325 can be rotated about axis G. The grips 350A, 350B can be squeezed or pinched together about the tubular support structure 351. The "pinching" or grasping degree of freedom in the grips is indicated by arrows Ha and Hb.

The touch sensitive handle 325 is rotatably supported by the first gimbal member 362 by means of a rotational joint 356g. The first gimbal member 362 is in turn, rotatably supported by the second gimbal member 364 by means of the rotational joint 356f. Similarly, the second gimbal member 364 is rotatably supported by the third gimbal member 366 using a rotational joint 356e. In this manner, the control input wrist 352 allows the touch sensitive handle 325 to be moved and oriented in the workspace using three degrees of freedom.

The movements in the gimbals 362, 364, 366 of the control input wrist 352 to reorient the touch sensitive handle 325 in space can be translated into control signals to control a robotic surgical manipulator and the robotic surgical tools. The movements in the grips 350A and 350B of the touch sensitive handle 325 can also be translated into control signals to control the robotic surgical manipulator and the robotic surgical tools. In particular, the squeezing motion of the grips 350A and 350B over their freedom of movement indicated by arrows Ha and Hb, may be used to control the end effectors of the robotic surgical tools.

To sense the movements in the touch sensitive handle 325 and generate controls signals, sensors can be mounted in the handle 325 as well as the first gimbal member 362 of the control input wrist 352. Exemplary sensors may be a pressure sensor, a Hall Effect transducer, a potentiometer, and/or an encoder, for example. The robotic surgical systems and handle assembly of FIG. 5 are further described in U.S. Pat. No. 8,224,484, titled METHODS OF USER INTERFACE WITH ALTERNATIVE TOOL MODE FOR ROBOTIC SURGICAL TOOLS, which issued Jul. 17, 2012, the entire disclosure of which is incorporated by reference herein.

Existing robotic systems can incorporate a surgical visualization system, as further described herein. In such instances, additional information regarding the surgical site can be determined and/or conveyed to the clinician(s) in the surgical theater, such as to a surgeon positioned at a surgeon's console. For example, the clinician(s) can observe an augmented view of reality of the surgical site that includes additional information such as various contours of the tissue surface, hidden critical structures, and/or one or more distances with respect to anatomical structures. In various instances, proximity data can be leveraged to improve one or more operations of the robotic surgical system and or controls thereof, as further described herein.

Input Control Devices

Referring again to the robotic system 150 in FIG. 3, the surgeon's console 152 allows the surgeon to provide manual input commands to the surgical robot 154 to effect control of the surgical tool and the various actuations thereof. Movement of an input control device by a surgeon at the surgeon's console 152 within a predefined working volume, or work envelope, results in a corresponding movement or operation of the surgical tool. For example, referring again to FIG. 2, a surgeon can engage each input control device 136 with one hand and move the input control devices 136 within the work envelope to provide control motions to the surgical tool. Surgeon's consoles (e.g. the surgeon's console 116 in FIGS. 1 and 2 and the surgeon's console 250 in FIG. 4) can be expensive and require a large footprint. For example, the working volume of the input control device (e.g. the handle/wrist assembly 262 in FIG. 4 and the control input wrist 352 and touch sensitive handle 325 in FIG. 5) at the surgeon's consoles can necessitate a large footprint, which impacts the usable space in the operating room (OR), training modalities, and cooperative procedures, for example. For example, such a large footprint can preclude the option of having multiple control stations in the OR, such as additional control stations for training or use by an assistant. Additionally, the size and bulkiness of a surgeon's console can be cumbersome to relocate within an operating room or move between operating rooms, for example.

Ergonomics is an important consideration for surgeons who may spend many hours each day in surgery and/or at the surgeon's console. Excessive, repetitive motions during surgical procedures can lead to fatigue and chronic injury for the surgeon. It can be desirable to maintain a comfortable posture and/or body position while providing inputs to the robotic system. However, in certain instances, the surgeon's posture and/or position may be compromised to ensure proper positioning of a surgical tool. For example, surgeons are often prone to contort their hands and/or extend their arms for long durations of time. In one instance, a gross control motion to move the surgical tool to the surgical site may result in the surgeon's arms being uncomfortably too outstretched and/or cramped uncomfortably close upon reaching the surgical site. In certain instances, poor ergonomic posturing achieved during the gross control motion may be maintained during a subsequent fine control motion, e.g. when manipulating tissue at the surgical site, which can further exasperate the poor ergonomics for the surgeon. Existing input control devices propose a one-size-fits-all approach regardless of the surgeon's anthropometrics; however, the ergonomic impact to a surgeon can vary and certain body types may be more burdened by the architecture of existing input control devices.

In certain instances, an input control device can be restrained within the work envelope that defines its range of motion. For example, the structure of the surgeon's console and/or the linkages on the input control device can limit the range of the motion of the input control device. In certain instances, the input control device can reach the end of its range of motion before the surgical tool is appropriately positioned. In such instances, a clutching mechanism can be required to reposition the input control device within the work envelope to complete the positioning of the surgical tool. A hypothetical work envelope 280 is shown in FIG. 4, for example. In various instances, the surgeon can be required to actuate a clutch (often in the form of a foot pedal or additional button on the handle of the input control device) to temporarily disengage the input control device from the surgical tool while the input control device is relocated to a desired position within the work envelope. This non-surgical motion by the surgeon can be referred to as a "rowing" motion to properly reposition the input control device within the work envelope because of the arm motion of the surgeon at the surgeon's console. Upon release of the clutch, the motions of the input control device can again control the surgical tool.

Clutching the input control device to maintain a suitable position within the work envelope poses an additional cognitive burden to the surgeon. In such instances, the surgeon is required to constantly monitor the position and orientation of his/her hands relative to the boundaries of the work envelope. Additionally, the clutching or "rowing" motion can be tedious to the surgeon and such a monotonous, repetitive motion does not match the analogous workflow of a surgical procedure outside the context of robotic surgery. Clutching also requires the surgeon to match a previous orientation of the handle when reengaging the system. For example, upon completion of a complex range of motion in which the surgeon "rows" or clutches the input control device back to a comfortable, home position, the surgeon and/or surgical robot must match the orientation of the handle of the input control device in the home position to the previous orientation of the handle in the extended position, which can be challenging. and/or require complex logic and/or mechanics.

Requiring a clutch mechanism also limits the availability of controls on the handle of the input control device. For example, a clutch actuator can take up valuable real estate on the handle, which cognitively and physically limits the availability of other controls on the handle. In turn, the complexity of other subsystems, such as a peddle board, is increased and the surgeon may be required to utilize multiple input systems to complete a simple task.

Non-clutched alternatives to such input control devices can reduce the footprint and cost of the surgeon's console, improve the surgeon's ergonomic experience, eliminate the physical and cognitive burdens associated with clutching, and/or provide additional real estate on the input control device for additional input controls, for example. Exemplary non-clutched input control devices are further described herein. Such non-clutched input control devices can be employed with a variety of robotic systems. Moreover, as further described herein, the non-clutched input control devices can leverage information from various distance determining subsystems also disclosed herein. For example, real-time structured light and three-dimensional shape modeling can inform the logic of such non-clutched input control devices such that a first mode and/or first collection of controls are enabled outside a predefined distance from an anatomical surface and/or critical structure and a second mode and/or second collection of controls are enabled within a predefined distance of the anatomical structure and/or critical structure. Various tissue proximity applications are further described herein.

Figure 6:
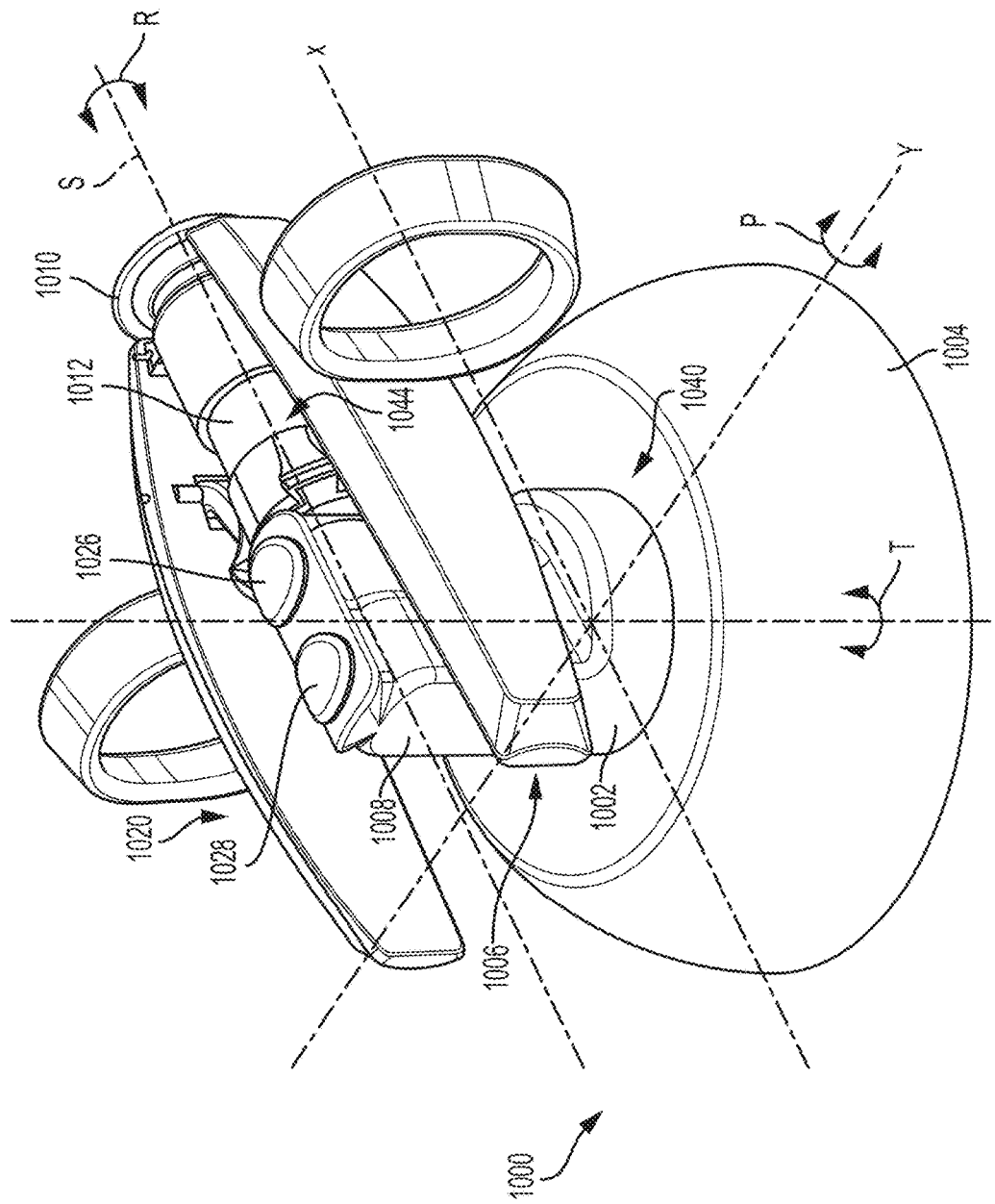
FIG. 6 is a perspective view of an input control device for a robotic surgical system, according to at least one aspect of the present disclosure.

Referring now to FIG. 6, an input control device 1000 is shown. The input control device 1000 is a clutchless input control device, as further described herein. The input control device 1000 can be utilized at a surgeon's console or workspace for a robotic surgical system. For example, the input control device 1000 can be incorporated into a surgical system, such as the surgical system 110 (FIG. 1) or the surgical system 150 (FIG. 3), for example, to provide control signals to a surgical robot and/or surgical tool coupled thereto based on a user input. The input control device 1000 includes input controls for moving the robotic arm and/or the surgical tool in three-dimensional space. For example, the surgical tool controlled by the input control device 1000 can be configured to move and/or rotate relative to X, Y, and Z axes.

Figure 7:
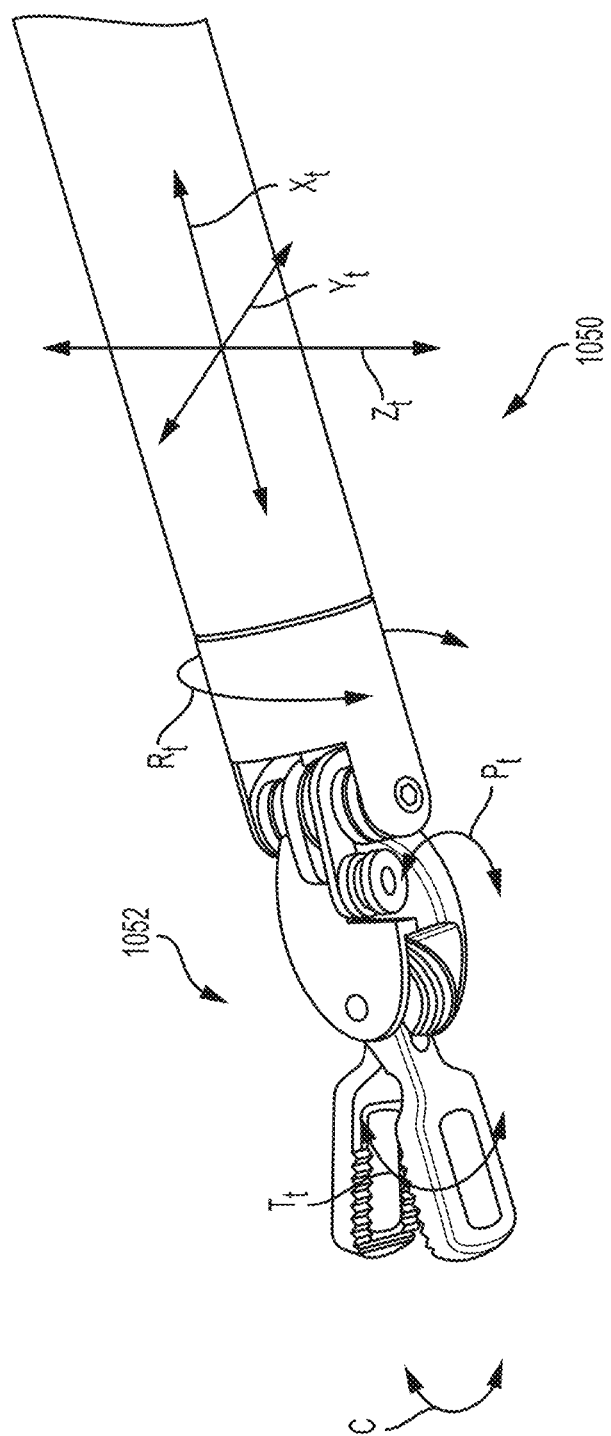
FIG. 7 is a perspective view of an end effector of a surgical tool operably controllable by control motions supplied to the input control device of FIG. 6, according to at least one aspect of the present disclosure.

An exemplary surgical tool 1050 is shown in FIG. 7. The surgical tool 1050 is a grasper that includes an end effector 1052 having opposing jaws, which are configured to releasably grab tissue. The surgical tool 1050 can be maneuvered in three dimensional space by translating the surgical tool 1050 along the $X_t$, $Y_t$, and $Z_t$ axes thereof. The surgical tool 1050 also includes a plurality of joints such that the surgical tool can be rotated and/or articulated into a desired configuration. The surgical tool 1050 can be configured to rotate or roll about the $X_t$ axis defined by the longitudinal shaft of the surgical tool 1050, rotate or articulate about a first articulation axis parallel to the $Y_t$ axis, and rotate or articulate about a second articulation axis parallel to the $Z_t$ axis. Rolling about the $X_t$ axis corresponds to a rolling motion of the end effector 1052 in the direction $R_t$, articulation about the first articulation axis corresponds to a pitching motion of the end effector 1052 in the direction $P_t$, and articulation about the second articulation axis corresponds to a yawing or twisting motion in the direction $T_t$.

An input control device, such as the input control device 1000, for example, can be configured to control the translation and rotation of the end effector 1052. To control such motion, the input control device 1000 includes corresponding input controls. For example, the input control device 1000 includes at least six degrees of freedom of input controls for moving the surgical tool 1050 in three dimensional space along the $X_t$, $Y_t$, and $Z_t$ axes, for rolling the end effector 1052 about the $X_t$ axis, and for articulating the end effector 1052 about the first and second articulation axes. Additionally, the input control device 1000 includes an end effector actuator for actuating the opposing jaws of the end effector 1052 to manipulate or grip tissue.

Referring again to FIG. 6, the input control device 1000 includes a multi-dimensional space joint 1006 having a central portion 1002 supported on a base 1004. The base 1004 is structured to rest on a surface, such as a desk or work surface at a surgeon's console or workspace. The base 1004 defines a circular base with a contoured edge; however, alternative geometries are contemplated. The base 1004 can remain in a fixed, stationary position relative to an underlying surface upon application of the input controls thereto. In certain instances, the base 1004 can be releasably secured and/or clamped to the underlying surface with fasteners, such as threaded fasteners, for example. In other instances, fasteners may not be required to hold the base 1004 to the underlying surface. In various instances, the base 1004 can include a sticky or tacking bottom surface and/or suction features (e.g. suction cups or magnets) for gripping an underlying surface. In certain instances, the base 1004 can include a ribbed and/or grooved bottom surface for engaging a complementary underlying support surface to maintain the base 1004 in a stationary state.

The space joint 1006 is configured to receive multi-dimensional manual inputs from a surgeon (e.g. the surgeon's hand or arm) corresponding to control motions for the surgical tool 1050 in multi-dimensional space. The central portion 1002 of the space joint 1006 is configured to receive input forces in multiple directions, such as forces along and/or about the X, Y, and Z axes. The central portion 1002 can include a raising, lowering, and rotating cylinder, shaft, or hemisphere, for example, projecting from the base 1004. The central portion 1002 is flexibly supported relative to the base 1004 such that the cylinder, shaft, and/or hemisphere is configured to move or float within a small predefined zone upon receipt of force control inputs thereto. For example, the central portion 1002 can be a floating shaft that is supported on the base 1004 by one or more elastomeric members such as springs, for example. The central portion 1002 can be configured to move or float within a predefined three-dimensional volume. For example, elastomeric couplings can permit movement of the central portion 1002 relative to the base 1004; however, restraining plates, pins, and/or other structures can be configured to limit the range of motion of the central portion 1002 relative to the base 1004.

In various instances, the space joint 1006 includes a multi-axis force and/or torque sensor arrangement 1048 (see FIG. 9) configured to detect the input forces and moments applied to the central portion 1002 and transferred to the space joint 1006. The sensor arrangement 1048 is positioned on one or more of the surfaces at the interface between the central portion 1002 and the base 1004. In other instances, the sensor arrangement 1048 can be embedded in the central portion 1002 or the base 1004. In still other instances, the sensor arrangement 1048 can be positioned on a floating member positioned intermediate the central portion 1002 and the base 1004.

The sensor arrangement 1048 can include one or more resistive strain gauges, optical force sensors, optical distance sensors, miniature cameras in the range of about 1.0 mm to about 3.0 mm in size, and/or time of flight sensors utilizing a pulsed light source, for example. In one aspect, the sensor arrangement 1048 includes a plurality of resistive strain gauges configured to detect the different force vectors applied thereto. The strain gauges can define a Wheatstone bridge configuration, for example. Additionally or alternatively, the sensor arrangement 1048 can include a plurality of optoelectronic sensors, such as measuring cells comprising a position-sensitive detector illuminated by a light-emitting element, such as an LED. Alternative force-detecting sensor arrangements are also contemplated. Exemplary multi-dimensional input devices and/or sensor arrangements are further described in the following references, which are incorporated by reference herein in their respective entireties:

U.S. Pat. No. 4,785,180, titled OPTOELECTRIC SYSTEM HOUSED IN A PLASTIC SPHERE, issued Nov. 15, 1988;

U.S. Pat. No. 6,804,012, titled ARRANGEMENT FOR THE DETECTION OF RELATIVE MOVEMENTS OR RELATIVE POSITION OF TWO OBJECTS, issued Oct. 12, 2004;

European Patent Application No. 1,850,210, titled OPTOELECTRONIC DEVICE FOR DETERMINING RELATIVE MOVEMENTS OR RELATIVE POSITIONS OF TWO OBJECTS, published Oct. 31, 2007;

U.S. Patent Application Publication No. 2008/0001919, titled USER INTERFACE DEVICE, published Jan. 3, 2008; and U.S. Pat. No. 7,516,675, titled JOYSTICK SENSOR APPARATUS, issued Apr. 14, 2009.

Referring again to the input device 1000 in FIG. 6, a joystick 1008 extends from the central portion 1002. Forces exerted on the central portion 1002 via the joystick 1008 define input motions for the sensor arrangement 1048. For example, the sensor arrangement 1048 in the base 1004 can be configured to detect the input forces and moments applied by a surgeon to the joystick 1008. The joystick 1008 can be spring-biased toward a central, or home, position, in which the joystick 1008 is aligned with the Z axis, a vertical axis through the joystick 1008, central portion 1002, and the space joint 1006. Driving (e.g. pushing and/or pulling) the joystick 1008 away from the Z axis in any direction can be configured to "drive" an end effector of an associated surgical tool in the corresponding direction. When the external driving force is removed, the joystick 1008 can be configured to return to the central, or home, position and motion of the end effector can be halted. For example, the central portion 1002 and joystick 1008 can be spring-biased toward the home position.

In various instances, the space joint 1006 and the joystick 1008 coupled thereto define a six degree-of-freedom input control. Referring again now to the end effector 1052 of the surgical tool 1050 in FIG. 7, the forces on the joystick 1008 of the input device 1000 in the X direction correspond to displacement of the end effector 1052 along the $X_t$ axis thereof (e.g. longitudinally), forces on the joystick 1008 in the Y direction correspond to displacement of the end effector 1052 along the $Y_t$ axis thereof (e.g. laterally), and forces on the joystick 1008 in the Z direction correspond to displacement of the end effector 1052 along the $Z_t$ axis (e.g. vertically/up and down). Additionally, forces on the joystick 1008 about the X axis (the moment forces R) result in rotation of the end effector 1052 about the $X_t$ axis (e.g. a rolling motion about a longitudinal axis in the direction $R_t$), forces on the joystick 1008 about the Y axis (the moments forces P) result in articulation of the end effector 1052 about the $Y_t$ axis (e.g. a pitching motion in the direction $P_t$), and forces on the joystick 1008 about the Z axis (the moment forces T) result in articulation of the end effector 1052 about the $Z_t$ axis of the end effector (e.g. a yawing or twisting motion in the direction $T_t$). In such instances, the input device 1000 comprises a six-degree of freedom joystick, which is configured to receive and detect six degrees-of-freedom—forces along the X, Y, and Z axes and moments about the X, Y, and Z axes. The forces can correspond to translational input and the moments can correspond to rotational inputs for the end effector 1052 of the associated surgical tool 1050. Six degree-of-freedom input devices are further described herein. Additional degrees of freedom (e.g. for actuating the jaws of an end effector or rolling the end effector about a longitudinal axis) can be provided by additional joints supported by the joystick 1008, as further described herein.

In various instances, the input control device 1000 includes a joint or wrist 1010 that is offset from the space joint 1006. The wrist 1010 is offset from the space joint 1006 by a shaft, or lever, 1012 extending along the shaft axis S that is parallel to the axis X in the configuration shown in FIG. 6. For example, the joystick 1008 can extend upright vertically from the central portion 1002 and the base 1004, and the joystick 1008 can support the shaft 1012.

As further described herein, the space joint 1006 can define the input control motions for multiple degrees of freedom. For example, the space joint 1006 can define the input control motions for translation of the surgical tool in three-dimensional space and articulation of the surgical tool about at least one axis. Rolling motions can also be controlled by inputs to the space joint 1006, as further described herein. Moreover, the wrist 1010 can define input control motions for at least one degree of freedom. For example, the wrist 1010 can define the input control motions for the rolling motion of the end effector. Moreover, the wrist 1010 can support an end effector actuator 1020, which is further described herein, to apply open and closing motions to the end effector.

In certain instances, the rolling, yawing, and pitching motions of the input control device 1000 are translatable motions that define corresponding input control motions for the related end effector. In various instances, the input control device 1000 can utilize adjustable scaling and/or gains such that the motion of the end effector is scalable in relationship to the control motions delivered at the wrist 1010.

In one aspect, the input control device 1000 includes a plurality of mechanical joints, which can be elastically-coupled components, sliders, journaled shafts, hinges, and/or rotary bearings, for example. The mechanical joints include a first joint 1040 (at the space joint 1006) intermediate the base 1004 and the central portion 1002, which allows rotation and tilting of the central portion 1002 relative to the base 1004, and a second joint 1044, which allows rotation of the wrist 1010 relative to the joystick 1008. In various instances, six degrees of freedom of a robotic end effector (e.g. three-dimensional translation and rotation about three different axes) can be controlled by user inputs at only these two joints 1040, 1044, for example. With respect to motion at the first joint 1040, the central portion 1002 can be configured to float relative to the base 1004 at elastic couplings. With respect to the second joint 1044, the wrist 1010 can be rotatably coupled to the shaft 1012, such that the wrist 1010 can rotate in the direction R (FIG. 6) about the shaft axis S. Rotation of the wrist 1010 relative to the shaft 1012 can correspond to a rolling motion of an end effector about a central tool axis, such as the rolling of the end effector 1052 about the $X_t$ axis. Rotation of the wrist 1010 by the surgeon to roll an end effector provides control of the rolling motion at the surgeon's fingertips and corresponds to a first-person perspective control of the end effector (i.e. from the surgeon's perspective, being "positioned" at the jaws of the remotely-positioned end effector at the surgical site). As further described herein, such placement and perspective can be utilized to supply precision control motions to the input control device 1000 during portions of a surgical procedure (e.g. a precision motion mode).

The various rotary joints of the input control device can include a sensor arrangement configured to detect the rotary input controls applied thereto. The wrist 1010 can include a rotary sensor, which can be a rotary force/torque sensor and/or transducer, rotary strain gauge and/or strain gauge on a spring, and/or an optical sensor to detect rotary displacement at the joint, for example.

In certain instances, the input control device 1000 can include one or more additional joints and/or hinges for the application of rotational input motions corresponding to articulation of an end effector. For example, the input control device 1000 can include a hinge along the shaft 1012 and/or between the shaft 1012 and the joystick 1008. In one instance, hinged input motions at such a joint can be detected by another sensor arrangement and converted to rotary input control motions for the end effector, such as a yawing or pitching articulation of the end effector. Such an arrangement requires one or more additional sensor arrangements and would increase the mechanical complexity of the input control device.

The input control device 1000 also includes at least one additional actuator, such as the actuation buttons 1026, 1028, for example, which can provide additional controls at the surgeon's fingertips. For example, the actuation buttons 1026, 1028 are positioned on the joystick 1008 of the input control device. The actuation buttons 1026, 1028 can correspond to buttons for activating the surgical tool, such as firing and/or retracting a knife, energizing one or more electrodes, and/or adjusting an energy modularity, for example. In other instances, the actuation buttons 1026, 1028 can provide inputs to an imaging system to adjust a view of the surgical tool, such as zooming in/out, panning, tracking, titling and/or rotating, for example.

In various aspects, the actuation buttons 1026 and 1028 are used to select between different motion scaling modes of the surgical tool 1050. For example, the actuation buttons 1026 and 1028 can be assigned to a gross motion mode and fine motion mode of the surgical tool 1050. The motion scaling of the surgical tool 1050 can be selectably adjusted to user input forces received by the input control device 1000, for example.

Additional details regarding the input control device 1000 and other robotic surgical system input control mechanisms can be found in U.S. patent application Ser. No. 16/354,417, titled INPUT CONTROLS FOR ROBOTIC SURGERY, which is herein incorporated by reference in its entirety.

Surgical Visualization Systems

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 8:
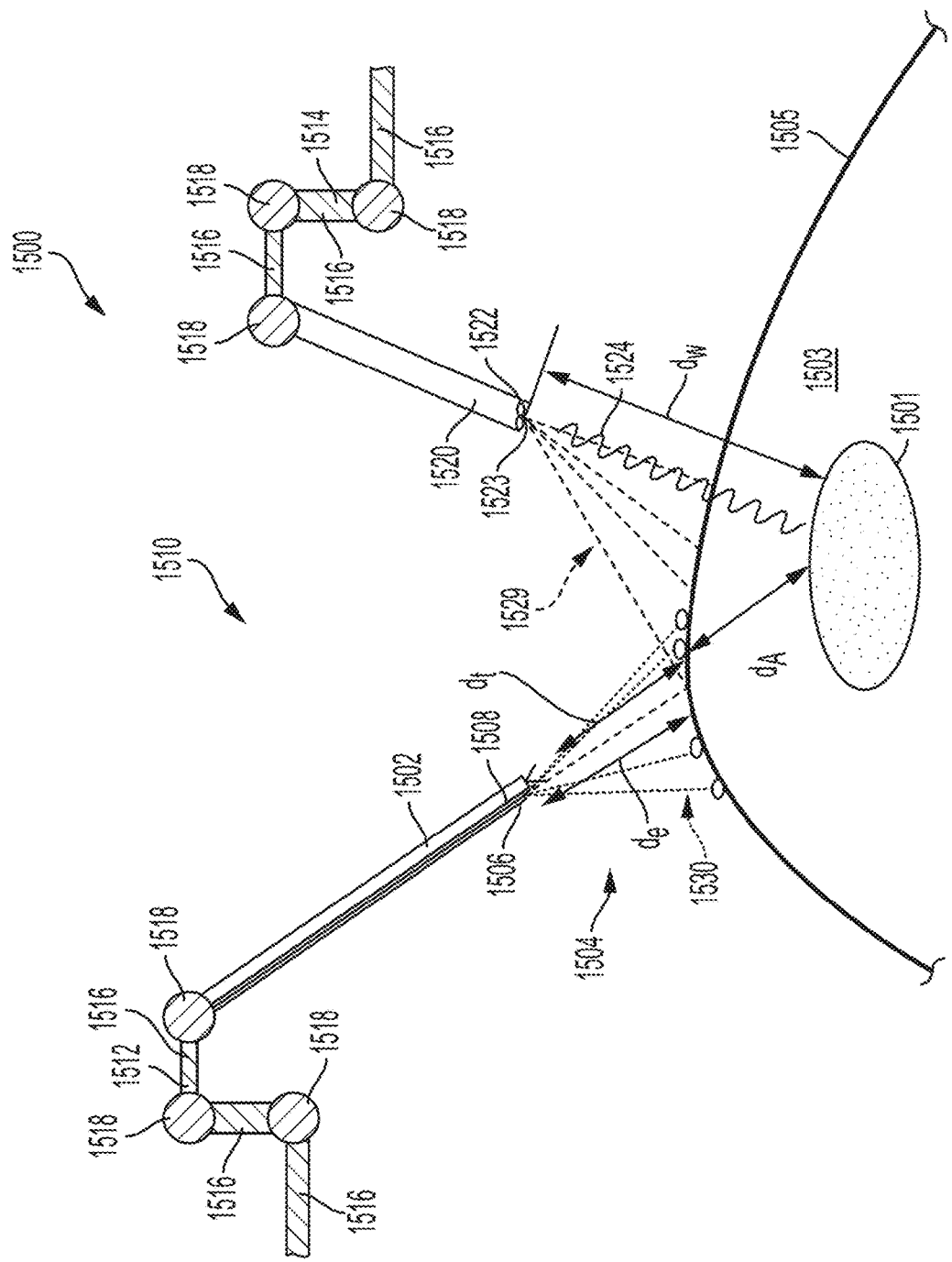
FIG. 8 is a schematic of a surgical visualization system including an imaging device and a surgical device, the surgical visualization system configured to identify a critical structure below a tissue surface, according to at least one aspect of the present disclosure.

FIG. 8 is a schematic of a surgical visualization system 1500 according to at least one aspect of the present disclosure. The surgical visualization system 1500 can create a visual representation of a critical structure 1501 within an anatomical field. The surgical visualization system 1500 can be used for clinical analysis and/or medical intervention, for example. In certain instances, the surgical visualization system 1500 can be used intraoperatively to provide real-time, or near real-time, information to the clinician regarding proximity data, dimensions, and/or distances during a surgical procedure. The surgical visualization system 1500 is configured for intraoperative identification of critical structure(s) and/or to facilitate the avoidance of the critical structure(s) 1501 by a surgical device. For example, by identifying the critical structure 1501, a clinician can avoid maneuvering a surgical device around the critical structure 1501 and/or a region in a predefined proximity of the critical structure 1501 during a surgical procedure. The clinician can avoid dissection of and/or near a vein, artery, nerve, and/or vessel, for example, identified as the critical structure 1501, for example. In various instances, the critical structure 1501 can be determined on a patient-by-patient and/or a procedure-by-procedure basis.

The surgical visualization system 1500 incorporates tissue identification and geometric surface mapping in combination with a distance sensor system 1504. In combination, these features of the surgical visualization system 1500 can determine a position of a critical structure 1501 within the anatomical field and/or the proximity of a surgical device 1502 to the surface 1505 of the visible tissue and/or to the critical structure 1501. Moreover, the surgical visualization system 1500 includes an imaging system that includes an imaging device 1520, such as a camera, for example, configured to provide real-time views of the surgical site. In various instances, the imaging device 1520 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 1520 can be provided to a clinician and, in various aspects of the present disclosure, can be augmented with additional information based on the tissue identification, landscape mapping, and the distance sensor system 1504. In such instances, the surgical visualization system 1500 includes a plurality of subsystems—an imaging subsystem, a surface mapping subsystem, a tissue identification subsystem, and/or a distance determining subsystem. These subsystems can cooperate to intraoperatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled METHODS AND APPARATUS FOR IMAGING OF OCCLUDED OBJECTS, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 9:
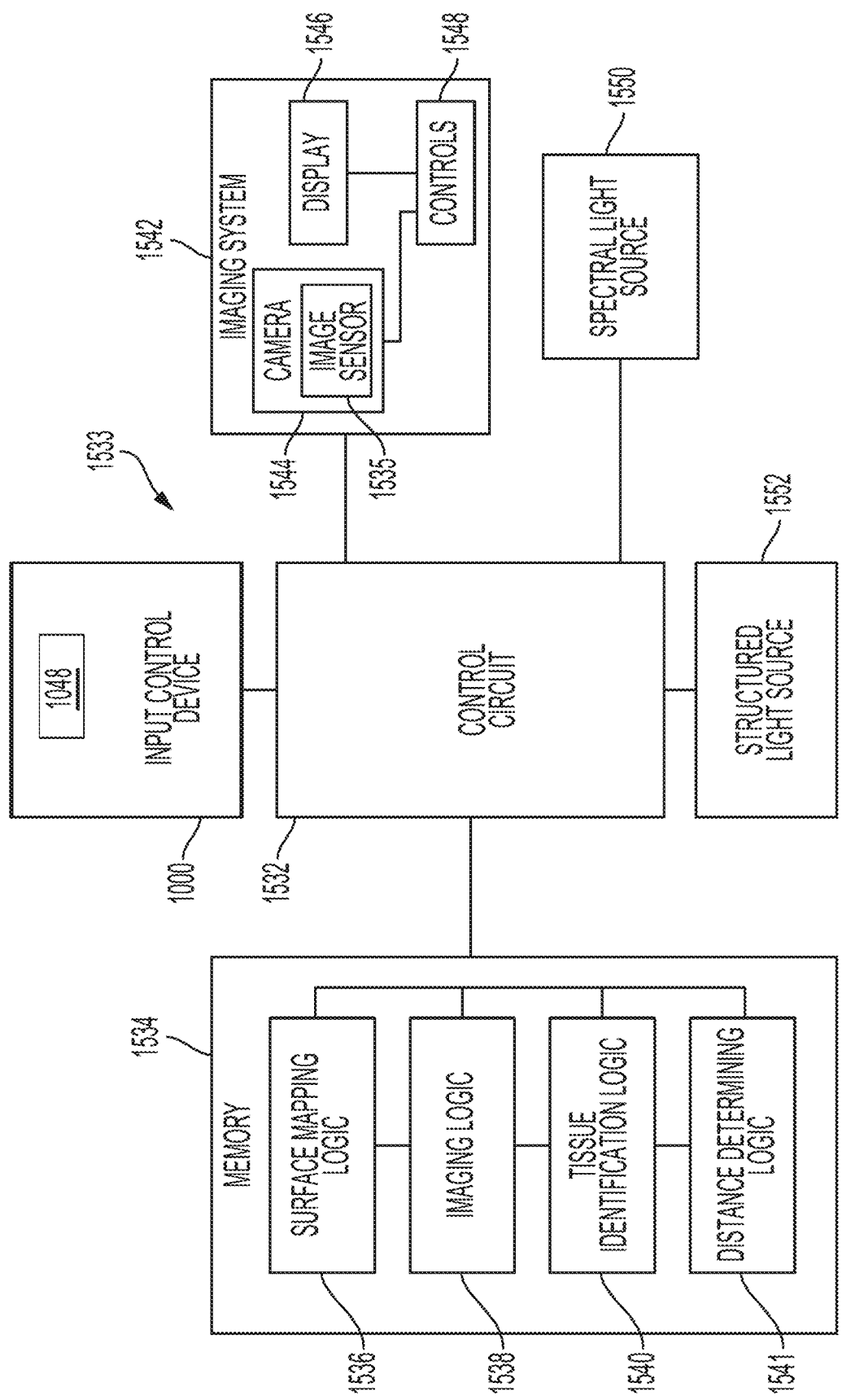
FIG. 9 is a schematic of a control system for a surgical visualization system, according to at least one aspect of the present disclosure.

FIG. 9 is a schematic diagram of a control system 1533, which can be utilized with the surgical visualization system 1500. The control system 1533 includes a control circuit 1532 in signal communication with a memory 1534. The memory 1534 stores instructions executable by the control circuit 1532 to determine and/or recognize critical structures (e.g. the critical structure 1501 in FIG. 8), determine and/or compute one or more distances and/or three-dimensional digital representations, and to communicate certain information to one or more clinicians. For example, the memory 1534 stores surface mapping logic 1536, imaging logic 1538, tissue identification logic 1540, or distance determining logic 1541 or any combinations of the logic 1536, 1538, 1540, and 1541. The control system 1533 also includes an imaging system 1542 having one or more cameras 1544 (like the imaging device 1520 in FIG. 8), one or more displays 1546, or one or more controls 1548 or any combinations of these elements. The camera 1544 can include one or more image sensors 1535 to receive signals from various light sources emitting light at various visible and invisible spectra (e.g. visible light, spectral imagers, three-dimensional lens, among others). The display 1546 can include one or more screens or monitors for depicting real, virtual, and/or virtually-augmented images and/or information to one or more clinicians.

In various aspects, the heart of the camera 1544 is the image sensor 1535. Generally, modern image sensors 1535 are solid-state electronic devices containing up to millions of discrete photodetector sites called pixels. The image sensor 1535 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 1535 employs a hybrid CCD/CMOS architecture (sold under the name "sCMOS") and consists of CMOS readout integrated circuits (ROICs) that are bump bonded to a CCD imaging substrate. CCD and CMOS image sensors 1535 are sensitive to wavelengths from approximately 350-1050 nm, although the range is usually given from 400-1000 nm. CMOS sensors are, in general, more sensitive to IR wavelengths than CCD sensors. Solid state image sensors 1535 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 1533 also includes a spectral light source 1550 and a structured light source 1552. In certain instances, a single source can be pulsed to emit wavelengths of light in the spectral light source 1550 range and wavelengths of light in the structured light source 1552 range. Alternatively, a single light source can be pulsed to provide light in the invisible spectrum (e.g. infrared spectral light) and wavelengths of light on the visible spectrum. The spectral light source 1550 can be a hyperspectral light source, a multispectral light source, and/or a selective spectral light source, for example. In various instances, the tissue identification logic 1540 can identify critical structure(s) via data from the spectral light source 1550 received by the image sensor 1535 portion of the camera 1544. The surface mapping logic 1536 can determine the surface contours of the visible tissue based on reflected structured light. With time-of-flight measurements, the distance determining logic 1541 can determine one or more distance(s) to the visible tissue and/or the critical structure 1501. One or more outputs from the surface mapping logic 1536, the tissue identification logic 1540, and the distance determining logic 1541, can be provided to the imaging logic 1538, and combined, blended, and/or overlaid to be conveyed to a clinician via the display 1546 of the imaging system 1542.

Figure 9A:
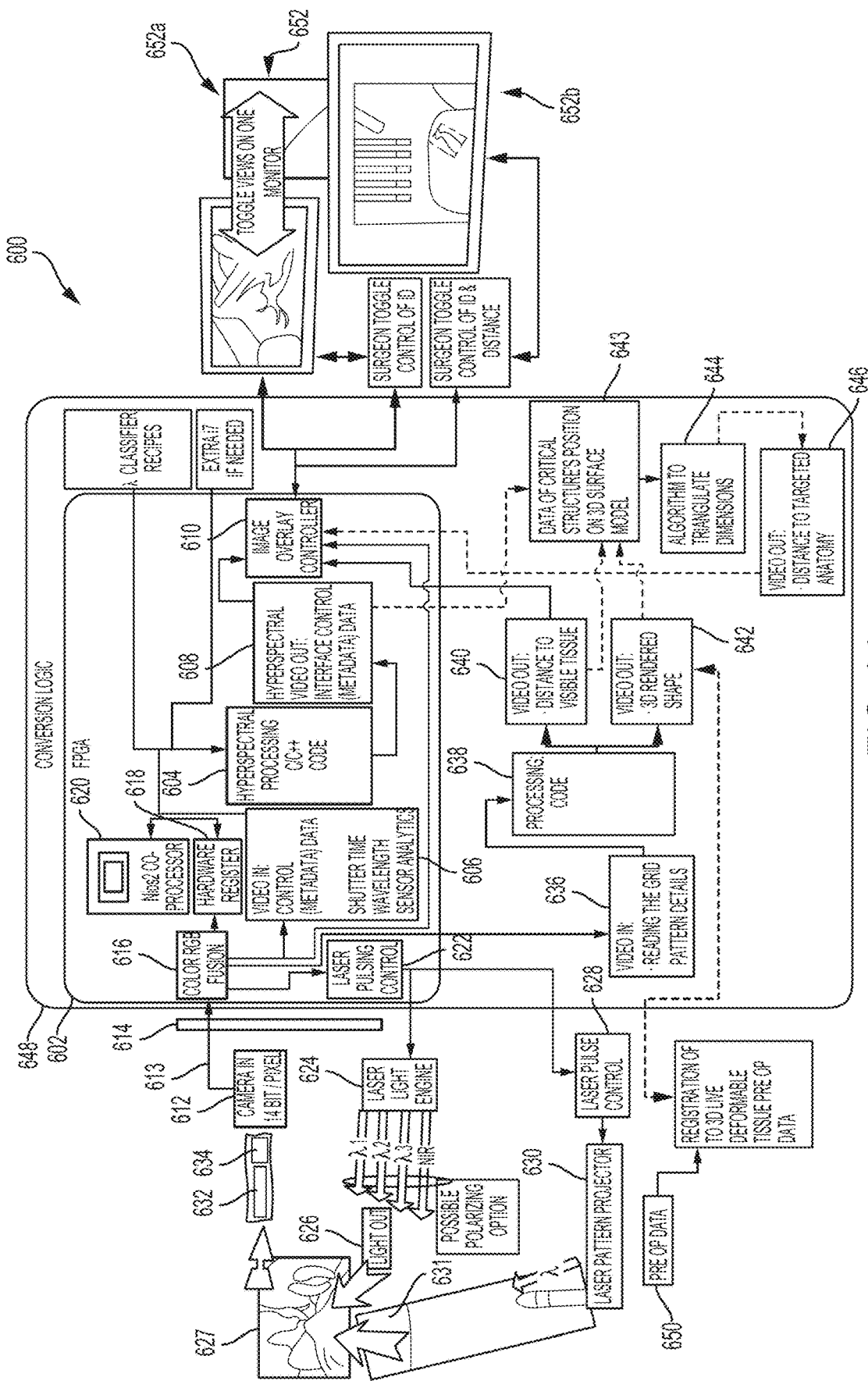
FIG. 9A is a schematic of a control system for a surgical visualization system, according to at least one aspect of the present disclosure.

Referring now to FIG. 9A, where a schematic of a control system 600 for a surgical visualization system, such as the surgical visualization system 1500, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 612, the laser light engine 624, and laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 10A:
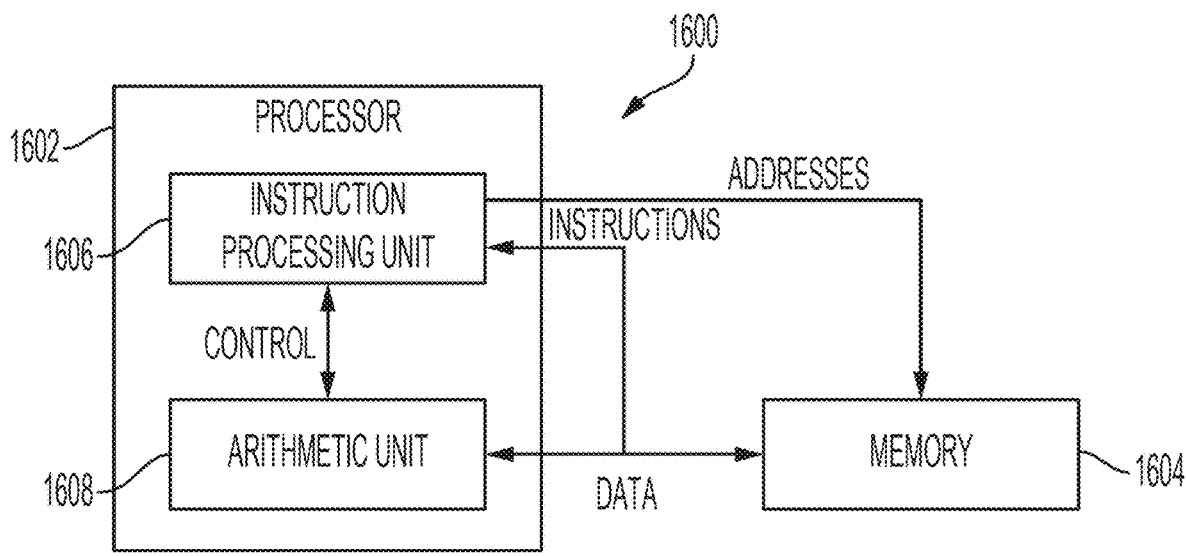
FIG. 10A illustrates a control circuit configured to control aspects of a surgical visualization system, according to at least one aspect of the present disclosure.
Figure 10B:
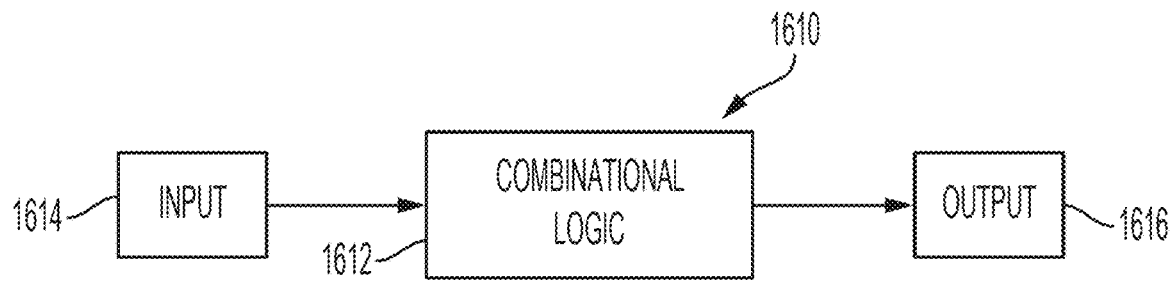
FIG. 10B illustrates a combinational logic circuit configured to control aspects of a surgical visualization system, according to at least one aspect of the present disclosure.
Figure 10C:
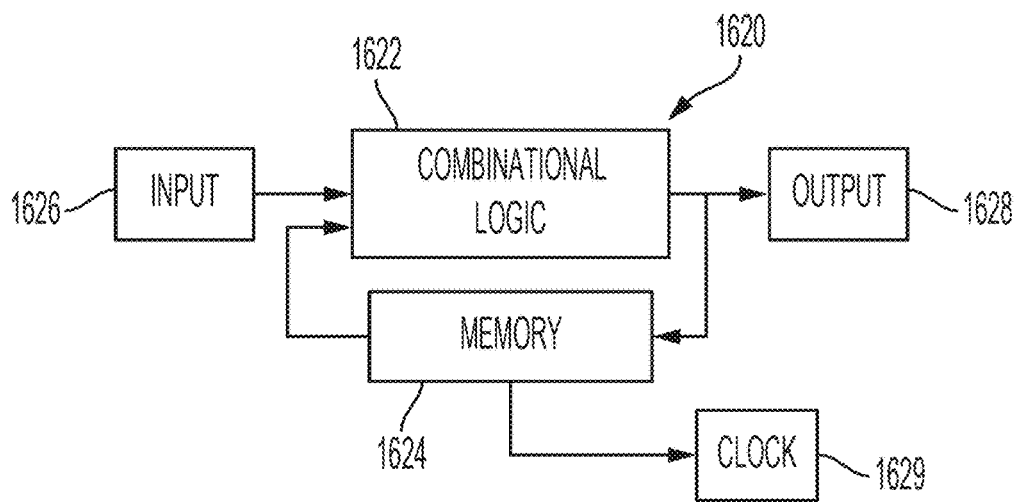
FIG. 10C illustrates a sequential logic circuit configured to control aspects of a surgical visualization system, according to at least one aspect of the present disclosure.

The description now turns briefly to FIGS. 10A-10C to describe various aspects of the control circuits 1532, 600 for controlling various aspects of the surgical visualization system 1500. Turning to FIG. 10A, there is illustrated a control circuit 1600 configured to control aspects of the surgical visualization system 1500, according to at least one aspect of this disclosure. The control circuit 1600 can be configured to implement various processes described herein. The control circuit 1600 may comprise a microcontroller comprising one or more processors 1602 (e.g., microprocessor, microcontroller) coupled to at least one memory circuit 1604. The memory circuit 1604 stores machine-executable instructions that, when executed by the processor 1602, cause the processor 1602 to execute machine instructions to implement various processes described herein. The processor 1602 may be any one of a number of single-core or multicore processors known in the art. The memory circuit 1604 may comprise volatile and non-volatile storage media. The processor 1602 may include an instruction processing unit 1606 and an arithmetic unit 1608. The instruction processing unit may be configured to receive instructions from the memory circuit 1604 of this disclosure.

FIG. 10B illustrates a combinational logic circuit 1610 configured to control aspects of the surgical visualization system 1500, according to at least one aspect of this disclosure. The combinational logic circuit 1610 can be configured to implement various processes described herein. The combinational logic circuit 1610 may comprise a finite state machine comprising a combinational logic 1612 configured to receive data associated with the surgical instrument or tool at an input 1614, process the data by the combinational logic 1612, and provide an output 1616.

FIG. 10C illustrates a sequential logic circuit 1620 configured to control aspects of the surgical visualization system 1500, according to at least one aspect of this disclosure. The sequential logic circuit 1620 or the combinational logic 1622 can be configured to implement various processes described herein. The sequential logic circuit 1620 may comprise a finite state machine. The sequential logic circuit 1620 may comprise a combinational logic 1622, at least one memory circuit 1624, and a clock 1629, for example. The at least one memory circuit 1624 can store a current state of the finite state machine. In certain instances, the sequential logic circuit 1620 may be synchronous or asynchronous. The combinational logic 1622 is configured to receive data associated with a surgical device or system from an input 1626, process the data by the combinational logic 1622, and provide an output 1628. In other aspects, the circuit may comprise a combination of a processor (e.g., processor 1602 in FIG. 10A) and a finite state machine to implement various processes herein. In other aspects, the finite state machine may comprise a combination of a combinational logic circuit (e.g., combinational logic circuit 1610, FIG. 10B) and the sequential logic circuit 1620.

Referring again to the surgical visualization system 1500 in FIG. 8, the critical structure 1501 can be an anatomical structure of interest. For example, the critical structure 1501 can be a ureter, an artery such as a superior mesenteric artery, a vein such as a portal vein, a nerve such as a phrenic nerve, and/or a tumor, among other anatomical structures. In other instances, the critical structure 1501 can be a foreign structure in the anatomical field, such as a surgical device, surgical fastener, clip, tack, bougie, band, and/or plate, for example. Example critical structures are further described in U.S. patent application Ser. No. 16/128,192, titled VISUALIZATION OF SURGICAL DEVICES, filed Sep. 11, 2018, which is hereby incorporated by reference herein in its entirety.

In one aspect, a critical structure can be on the surface 1505 of the tissue 1503. In another aspect, the critical structure 1501 may be embedded in tissue 1503. Stated differently, the critical structure 1501 may be positioned below the surface 1505 of the tissue 1503. In such instances, the tissue 1503 conceals the critical structure 1501 from the clinician's view. The critical structure 1501 is also obscured from the view of the imaging device 1520 by the tissue 1503. The tissue 1503 can be fat, connective tissue, adhesions, and/or organs, for example. In other instances, the critical structure 1501 can be partially obscured from view.

FIG. 8 also depicts the surgical device 1502. The surgical device 1502 includes an end effector having opposing jaws extending from the distal end of the shaft of the surgical device 1502. The surgical device 1502 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 1502 can include another imaging or diagnostic modality, such as an ultrasound device, for example. In one aspect of the present disclosure, the surgical visualization system 1500 can be configured to achieve identification of one or more critical structures 1501 and the proximity of the surgical device 1502 to the critical structure(s) 1501.

The imaging device 1520 of the surgical visualization system 1500 is configured to detect light at various wavelengths, such as, for example, visible light, spectral light waves (visible or invisible), and a structured light pattern (visible or invisible). The imaging device 1520 may include a plurality of lenses, sensors, and/or receivers for detecting the different signals. For example, the imaging device 1520 can be a hyperspectral, multispectral, or selective spectral camera, as further described herein. The imaging device 1520 can also include a waveform sensor 1522 (such as a spectral image sensor, detector, and/or three-dimensional camera lens). For example, the imaging device 1520 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 1520 can be configured to receive images indicative of the topography of the visible tissue and the identification and position of hidden critical structures, as further described herein. For example, the field of view of the imaging device 1520 can overlap with a pattern of light (structured light) on the surface 1505 of the tissue, as shown in FIG. 8.

In one aspect, the surgical visualization system 1500 may be incorporated into a robotic system 1510. For example, the robotic system 1510 may include a first robotic arm 1512 and a second robotic arm 1514. The robotic arms 1512, 1514 include rigid structural members 1516 and joints 1518, which can include servomotor controls. The first robotic arm 1512 is configured to maneuver the surgical device 1502, and the second robotic arm 1514 is configured to maneuver the imaging device 1520. A robotic control unit can be configured to issue control motions to the robotic arms 1512, 1514, which can affect the surgical device 1502 and the imaging device 1520, for example.

The surgical visualization system 1500 also includes an emitter 1506, which is configured to emit a pattern of light, such as stripes, grid lines, and/or dots, to enable the determination of the topography or landscape of the surface 1505. For example, projected light arrays 1530 can be used for three-dimensional scanning and registration on the surface 1505. The projected light arrays 1530 can be emitted from the emitter 1506 located on the surgical device 1502 and/or one of the robotic arms 1512, 1514 and/or the imaging device 1520, for example. In one aspect, the projected light array 1530 is employed to determine the shape defined by the surface 1505 of the tissue 1503 and/or the motion of the surface 1505 intraoperatively. The imaging device 1520 is configured to detect the projected light arrays 1530 reflected from the surface 1505 to determine the topography of the surface 1505 and various distances with respect to the surface 1505.

In one aspect, the imaging device 1520 also may include an optical waveform emitter 1523 that is configured to emit an array 1529 of electromagnetic radiation 1524 (NIR photons) that can penetrate the surface 1505 of the tissue 1503 and reach the critical structure 1501. The imaging device 1520 and the optical waveform emitter 1523 thereon can be positionable by the robotic arm 1514. A corresponding waveform sensor 1522 (an image sensor, spectrometer, or vibrational sensor, for example) on the imaging device 1520 is configured to detect the effect of the electromagnetic radiation received by the waveform sensor 1522. The wavelengths of the electromagnetic radiation 1524 emitted by the optical waveform emitter 1523 can be configured to enable the identification of the type of anatomical and/or physical structure, such as the critical structure 1501. The identification of the critical structure 1501 can be accomplished through spectral analysis, photo-acoustics, and/or ultrasound, for example. In one aspect, the wavelengths of the electromagnetic radiation 1524 may be variable. The waveform sensor 1522 and optical waveform emitter 1523 may be inclusive of a multispectral imaging system and/or a selective spectral imaging system, for example. In other instances, the waveform sensor 1522 and optical waveform emitter 1523 may be inclusive of a photoacoustic imaging system, for example. In other instances, the optical waveform emitter 1523 can be positioned on a separate surgical device from the imaging device 1520.

The surgical visualization system 1500 also may include the distance sensor system 1504 configured to determine one or more distances at the surgical site. In one aspect, the time-of-flight distance sensor system 1504 may be a time-of-flight distance sensor system that includes an emitter, such as the emitter 1506, and a receiver 1508, which can be positioned on the surgical device 1502. In other instances, the time-of-flight emitter can be separate from the structured light emitter. In one general aspect, the emitter 1506 portion of the time-of-flight distance sensor system 1504 may include a very tiny laser source and the receiver 1508 portion of the time-of-flight distance sensor system 1504 may include a matching sensor. The time-of-flight distance sensor system 1504 can detect the "time of flight," or how long the laser light emitted by the emitter 1506 has taken to bounce back to the sensor portion of the receiver 1508. Use of a very narrow light source in the emitter 1506 enables the distance sensor system 1504 to determining the distance to the surface 1505 of the tissue 1503 directly in front of the distance sensor system 1504. Referring still to FIG. 8, $d_e$ is the emitter-to-tissue distance from the emitter 1506 to the surface 1505 of the tissue 1503 and $d_t$ is the device-to-tissue distance from the distal end of the surgical device 1502 to the surface 1505 of the tissue. The distance sensor system 1504 can be employed to determine the emitter-to-tissue distance $d_e$. The device-to-tissue distance $d_t$ is obtainable from the known position of the emitter 1506 on the shaft of the surgical device 1502 relative to the distal end of the surgical device 1502. In other words, when the distance between the emitter 1506 and the distal end of the surgical device 1502 is known, the device-to-tissue distance $d_t$ can be determined from the emitter-to-tissue distance $d_e$. In certain instances, the shaft of the surgical device 1502 can include one or more articulation joints, and can be articulatable with respect to the emitter 1506 and the jaws. The articulation configuration can include a multi-joint vertebrae-like structure, for example. In certain instances, a three-dimensional camera can be utilized to triangulate one or more distances to the surface 1505.

In various instances, the receiver 1508 for the time-of-flight distance sensor system 1504 can be mounted on a separate surgical device instead of the surgical device 1502. For example, the receiver 1508 can be mounted on a cannula or trocar through which the surgical device 1502 extends to reach the surgical site. In still other instances, the receiver 1508 for the time-of-flight distance sensor system 1504 can be mounted on a separate robotically-controlled arm (e.g. the robotic arm 1514), on a movable arm that is operated by another robot, and/or to an operating room (OR) table or fixture. In certain instances, the imaging device 1520 includes the time-of-flight receiver 1508 to determine the distance from the emitter 1506 to the surface 1505 of the tissue 1503 using a line between the emitter 1506 on the surgical device 1502 and the imaging device 1520. For example, the distance $d_e$ can be triangulated based on known positions of the emitter 1506 (on the surgical device 1502) and the receiver 1508 (on the imaging device 1520) of the time-of-flight distance sensor system 1504. The three-dimensional position of the receiver 1508 can be known and/or registered to the robot coordinate plane intraoperatively.

In certain instances, the position of the emitter 1506 of the time-of-flight distance sensor system 1504 can be controlled by the first robotic arm 1512 and the position of the receiver 1508 of the time-of-flight distance sensor system 1504 can be controlled by the second robotic arm 1514. In other instances, the surgical visualization system 1500 can be utilized apart from a robotic system. In such instances, the distance sensor system 1504 can be independent of the robotic system.

In certain instances, one or more of the robotic arms 1512, 1514 may be separate from a main robotic system used in the surgical procedure. At least one of the robotic arms 1512, 1514 can be positioned and registered to a particular coordinate system without a servomotor control. For example, a closed-loop control system and/or a plurality of sensors for the robotic arms 1512, 1514 can control and/or register the position of the robotic arm(s) 1512, 1514 relative to the particular coordinate system. Similarly, the position of the surgical device 1502 and the imaging device 1520 can be registered relative to a particular coordinate system.

Figure 11:
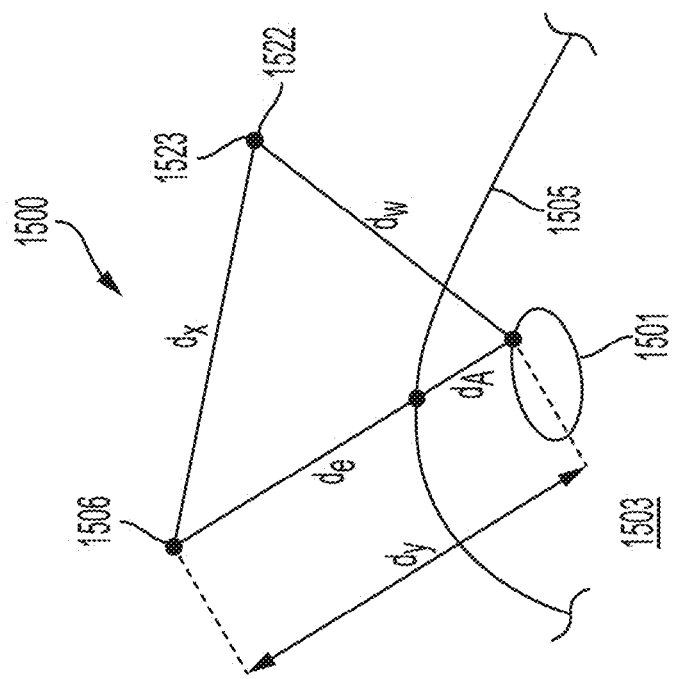
FIG. 11 is a schematic depicting triangularization between the surgical device, the imaging device, and the critical structure of FIG. 8 to determine a depth $d_A$ of the critical structure below the tissue surface, according to at least one aspect of the present disclosure.

Referring still to FIG. 8, $d_w$ is the camera-to-critical structure distance from the optical waveform emitter 1523 located on the imaging device 1520 to the surface of the critical structure 1501, and $d_A$ is the depth of the critical structure 1501 below the surface 1505 of the tissue 1503 (i.e., the distance between the portion of the surface 1505 closest to the surgical device 1502 and the critical structure 1501). In various aspects, the time-of-flight of the optical waveforms emitted from the optical waveform emitter 1523 located on the imaging device 1520 can be configured to determine the camera-to-critical structure distance $d_w$. The use of spectral imaging in combination with time-of-flight sensors is further described herein. Moreover, referring now to FIG. 11, in various aspects of the present disclosure, the depth $d_A$ of the critical structure 1501 relative to the surface 1505 of the tissue 1503 can be determined by triangulating from the distance $d_w$ and known positions of the emitter 1506 on the surgical device 1502 and the optical waveform emitter 1523 on the imaging device 1520 (and, thus, the known distance $d_x$ therebetween) to determine the distance $d_y$, which is the sum of the distances $d_e$ and $d_A$.

Additionally or alternatively, time-of-flight from the optical waveform emitter 1523 can be configured to determine the distance from the optical waveform emitter 1523 to the surface 1505 of the tissue 1503. For example, a first waveform (or range of waveforms) can be utilized to determine the camera-to-critical structure distance $d_w$ and a second waveform (or range of waveforms) can be utilized to determine the distance to the surface 1505 of the tissue 1503. In such instances, the different waveforms can be utilized to determine the depth of the critical structure 1501 below the surface 1505 of the tissue 1503.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 12:
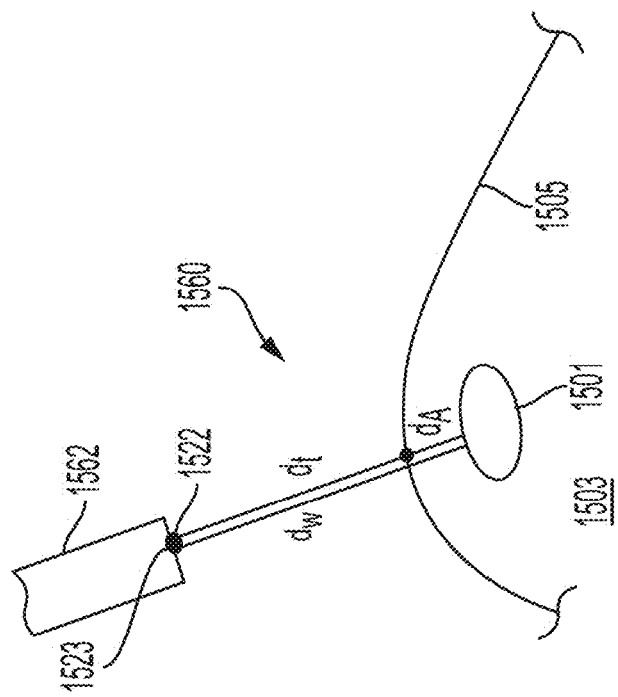
FIG. 12 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 1560 in FIG. 12, in which a surgical device 1562 includes the optical waveform emitter 1523 and the waveform sensor 1522 that is configured to detect the reflected waveforms. The optical waveform emitter 1523 can be configured to emit waveforms for determining the distances $d_t$ and $d_w$ from a common device, such as the surgical device 1562, as further described herein. In such instances, the distance $d_A$ from the surface 1505 of the tissue 1503 to the surface of the critical structure 1501 can be determined as follows:

$$d_A = d_w - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 1520 can include multiple image sensors.

FIG. 13 depicts a surgical visualization system 1700, which is similar to the surgical visualization system 1500 in many respects. In various instances, the surgical visualization system 1700 can be a further exemplification of the surgical visualization system 1500. Similar to the surgical visualization system 1500, the surgical visualization system 1700 includes a surgical device 1702 and an imaging device 1720. The imaging device 1720 includes a spectral light emitter 1723, which is configured to emit spectral light in a plurality of wavelengths to obtain a spectral image of hidden structures, for example. The imaging device 1720 can also include a three-dimensional camera and associated electronic processing circuits in various instances. The surgical visualization system 1700 is shown being utilized intraoperatively to identify and facilitate avoidance of certain critical structures, such as a ureter 1701a and vessels 1701b in an organ 1703 (the uterus in this example), that are not visible on the surface.

The surgical visualization system 1700 is configured to determine an emitter-to-tissue distance $d_e$ from an emitter 1706 on the surgical device 1702 to a surface 1705 of the uterus 1703 via structured light. The surgical visualization system 1700 is configured to extrapolate a device-to-tissue distance $d_t$ from the surgical device 1702 to the surface 1705 of the uterus 1703 based on the emitter-to-tissue distance $d_e$. The surgical visualization system 1700 is also configured to determine a tissue-to-ureter distance $d_A$ from the ureter 1701a to the surface 1705 and a camera-to ureter distance $d_w$ from the imaging device 1720 to the ureter 1701a. As described herein with respect to FIG. 8, for example, the surgical visualization system 1700 can determine the distance $d_w$ with spectral imaging and time-of-flight sensors, for example. In various instances, the surgical visualization system 1700 can determine (e.g. triangulate) the tissue-to-ureter distance $d_A$ (or depth) based on other distances and/or the surface mapping logic described herein.

In still other aspects, the surgical visualization systems 1500, 1700 can determine the distance or relative position of critical structures utilizing fluoroscopy visualization techniques (e.g., utilizing a pair of cameras to triangulate the position of a structure or the contents thereof treated with a fluorescent agent) or employing dithering cameras, as are disclosed in U.S. patent application Ser. No. 16/128,180, titled CONTROLLING AN EMITTER ASSEMBLY PULSE SEQUENCE, filed Sep. 11, 2018, which is hereby incorporated by reference herein in its entirety. In one aspect, a fluoroscopy visualization technology, such as fluorescent Indocyanine green (ICG), for example, can be utilized to illuminate a critical structure 3201, as shown in FIGS. 13F-13I. A camera 3220 can include two optical waveforms sensors 3222, 3224, which take simultaneous left-side and right-side images of the critical structure 3201 (FIGS. 13G and 13H). In such instances, the camera 3220 can depict a glow of the critical structure 3201 below the surface 3205 of the tissue 3203, and the distance $d_w$ can be determined by the known distance between the sensors 3222 and 3224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

In still other aspects, the surgical visualization system 1500 may employ two separate waveform receivers (i.e. cameras/image sensors) to determine $d_w$. Referring now to FIG. 13J, if a critical structure 3301 or the contents thereof (e.g. a vessel or the contents of the vessel) can emit a signal 3302, such as with fluoroscopy, then the actual location can be triangulated from two separate cameras 3320a, 3320b at known locations.

FIG. 13K illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 520 (FIG. 24), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which case the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured light.

In various instances, hyperspectral imaging technology, can be employed to identify signatures in anatomical structures in order to differentiate a critical structure from obscurants. Hyperspectral imaging technology may provide a visualization system that can provide a way to identify critical structures such as ureters and/or blood vessels, for example, especially when those structures are obscured by fat, connective tissue, blood, or other organs, for example. The use of the difference in reflectance of different wavelengths in the infrared (IR) spectrum may be employed to determine the presence of key structures versus obscurants. Referring now to FIGS. 13L-13N, illustrative hyperspectral signatures for a ureter, an artery, and nerve tissue with respect to obscurants such as fat, lung tissue, and blood, for example, are depicted.

FIG. 13L is a graphical representation 950 of an illustrative ureter signature versus obscurants. The plots represent reflectance as a function of wavelength (nm) for wavelengths for fat, lung tissue, blood, and a ureter. FIG. 13M is a graphical representation 952 of an illustrative artery signature versus obscurants. The plots represent reflectance as a function of wavelength (nm) for fat, lung tissue, blood, and a vessel. FIG. 13N is a graphical representation 954 of an illustrative nerve signature versus obscurants. The plots represent reflectance as a function of wavelength (nm) for fat, lung tissue, blood, and a nerve.

In another aspect, a surgical visualization system 1500 may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 13A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 13B, the camera 440 is moved axially along the axis A and is rotated an angle $\theta_3$ about the axis A. A pivot point 442 for rotation of the camera 440 is positioned at the cannula/patient interface. In FIG. 13B, the camera 440 is translated and rotated to a location 440". As the camera 440 moves and the edge of view changes with respect to the critical structure 401, the distance to the critical structure 401 can be calculated. In FIG. 13B, a distance $d_2$ can be 9.01 mm, for example, and the angle $\theta_3$ can be 0.9 degrees, for example.

Spectral imaging can be utilized intraoperatively to measure the distance between a waveform emitter and a critical structure that is obscured by tissue. In one aspect of the present disclosure, referring now to FIGS. 13C and 13D, a time-of-flight sensor system 1104 utilizing waveforms 1124, 1125 is shown. The time-of-flight sensor system 1104 can be incorporated into the surgical visualization system 1500 (FIG. 8) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 13D, for example, which can be measured by the receiver 1108.

Based on the delay between the emitted wave 1124 and the received wave 1125, the time-of-flight sensor system 1104 is configured to determine the distance d (FIG. 13C). A time-of-flight timing diagram 1130 for the emitter 1106 and the receiver 1108 of FIG. 13C is shown in FIG. 13D. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 1124, 1125 corresponds to the distance d in FIG. 13C. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t.$$

where:
$d_A$=the depth of the critical structure 1101 below the surface 1105 of the obscuring tissue 1103;
$d_w$=the distance from the emitter 1106 to the critical structure 1101 (d in FIG. 13C); and
$d_t$=the distance from the emitter 1106 (on the distal end of the surgical device 1102) to the surface 1105 of the obscuring tissue 1103.

In one aspect of the present disclosure, referring now to FIG. 13E, a time-of-flight sensor system 1204 utilizing waves 1224*a*, 1224*b*, 1224*c*, 1225*a*, 1225*b*, 1225*c* is shown. The time-of-flight sensor system 1204 can be incorporated into the surgical visualization system 1500 (FIG. 8) in certain instances. The time-of-flight sensor system 1204 includes a waveform emitter 1206 and a waveform receiver 1208. The waveform emitter 1206 is positioned on a first surgical device 1202*a*, and the waveform receiver 1208 is positioned on a second surgical device 1202*b*. The surgical devices 1202*a*, 1202*b* are positioned through their respective trocars 1210*a*, 1210*b*, respectively, which extend into a cavity 1207 in a patient. The emitted waves 1224*a*, 1224*b*, 1224*c* extend toward a surgical site from the emitter 1206 and the received waves 1225*a*, 1225*b*, 1225*c* are reflected back to the receiver 1208 from various structures and/or surfaces at the surgical site.

The different emitted waves 1224*a*, 1224*b*, 1224*c* are configured to target different types of material at the surgical site. For example, the wave 1224*a* targets the obscuring tissue 1203, the wave 1224*b* targets a first critical structure 1201*a* (e.g. a vessel), and the wave 1224*c* targets a second critical structure 1201*b* (e.g. a cancerous tumor). The wavelengths of the waves 1224*a*, 1224*b*, 1224*c* can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224*b*, 1224*c* can be selected to target the critical structures 1201*a*, 1201*b* within the tissue 1203 based on the spectral signature of the critical structure 1201*a*, 1201*b*, as further described herein. Photoacoustic imaging is further described herein and in the aforementioned contemporaneously-filed U.S. Patent Applications, which are incorporated by reference herein in their respective entireties.

The emitted waves 1224*a*, 1224*b*, 1224*c* can be reflected off the targeted material (i.e. the surface 1205, the first critical structure 1201*a*, and the second structure 1201*b*, respectively). The received waveforms 1225*a*, 1225*b*, 1225*c* can be delayed due to the distances $d_{1a}$, $d_{2a}$, $d_{3a}$, $d_{1b}$, $d_{2b}$, $d_{3b}$ indicated in FIG. 13E.

In the time-of-flight sensor system 1204, in which the emitter 1206 and the receiver 1208 are independently positionable (e.g., on separate surgical devices 1202*a*, 1202*b* and/or controlled by separate robotic arms), the various distances $d_{1a}$, $d_{2a}$, $d_{3a}$, $d_{1b}$, $d_{2b}$, $d_{3b}$ can be calculated from the known position of the emitter 1206 and the receiver 1208. For example, the positions can be known when the surgical devices 1202*a*, 1202*b* are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}$, $d_{2a}$, $d_{3a}$, $d_{1b}$, $d_{2b}$, $d_{3b}$. In one aspect, the distance to the obscured critical structures 1201*a*, 1201*b* can be triangulated using penetrating wavelengths. Because the speed of light is constant for any wavelength of visible or invisible light, the time-of-flight sensor system 1204 can determine the various distances.

Referring still to FIG. 13E, in various instances, in the view provided to the clinician, the receiver 1208 can be rotated such that the center of mass of the target structure in the resulting images remains constant, i.e., in a plane perpendicular to the axis of a select target structures 1203, 1201*a*, or 1201*b*. Such an orientation can quickly communicate one or more relevant distances and/or perspectives with respect to the critical structure. For example, as shown in FIG. 13E, the surgical site is displayed from a viewpoint in which the critical structure 1201*a* is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210*b*, for example, through which the surgical device 1202*b* is positioned. In other instances, the receiver 1208 can be mounted on a separate robotic arm for which the three-dimensional position is known. In various instances, the receiver 1208 can be mounted on a movable arm that is separate from the robot that controls the surgical device 1202*a* or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Scaling Movement According to Tissue Proximity

Many surgical robotic control interfaces force the user to move their arms within a control space having a set "working volume" to manipulate the movement and position of the surgical tools 126, 1050 (FIGS. 1 and 7) and/or imaging devices 128 (FIG. 1) of the robotic surgical system 110, 150 (FIGS. 1, 3) within the operative space (i.e., the total volume within which a user may wish to move or position the surgical tools 1050 and/or imaging devices 128 during a surgical procedure). Oftentimes, a user can reach the outer limits of their control space but not the outer limits of their operative space. In other words, the control space for a robotic surgical system 110 may not be coextensive with the available operative space in which the user may wish to manipulate the surgical tools 1050 during a surgical procedure. In such instances, the user must clutch out of the robotic input control devices 136 (FIG. 2), move their hands back to a "home position" closer to their bodies, clutch back into the input control devices 136, and then continue the surgical procedure. However, forcing users to clutch in and out of the input control devices 136 is time consuming and unintuitive, which can impact the efficiency of the surgical procedure. When a surgical procedure is not time efficient or movement efficient for the operator of the robotic surgical system 110, the additional time and exertion required by the surgeon to perform the procedure can lead to fatigue, which can in turn impact the success of the surgical procedure. Therefore, it can be desirable to scale the movement of the robotic surgical system 110 such that the range of movement of the surgical system 110 is scaled with respect to the movement of the input control devices 136.

Further, surgical robotic interfaces that utilize set relationships between input received from the input control devices 136 and the resulting movement in the surgical system 110 fail to account for the fact that, in some circumstances, it is not desirable for the robotic surgical system 110 to be equally sensitive to movement input. For example, when a surgical tool 1050 is in close proximity to a patient to be treated by the surgical tool, inadvertent control inputs have much larger consequences than when the surgical tool 1050 is far from the patient because in the former situation the surgical tool 1050 can inadvertently contact and cause harm to the patient. Therefore, it can be desirable to adjust the movement of the robotic surgical system 110 when a surgical tool 1050 or another component thereof is near the patient. In other words, the scaling of the movement of a surgical tool is adjusted in accordance with its distance from the patient. Accordingly, a robotic surgical system 110 can be configured to tailor the movement of its surgical tools 1050 in response to a user input according to the distance between the surgical tool 1050 or a component thereof, such as an end effector 1052 (FIG. 7), and the patient.

As used herein, the term "surgical tool" can refer to a grasper (as illustrated in FIG. 7), a surgical stapler, an ultrasonic surgical instrument, a monopolar or bipolar electrosurgical instrument, and so on. By causing the movement of the robotic surgical system 110 to be a function of the proximity of the surgical tools 1050 to the patient, the robotic control interface's control space can be coextensive with the operative space of the robotic surgical system 110. For example, the relationship between the amount of movement in the robotic surgical system 110 and the input received from the input control devices 136 can be inconstant such that the robotic surgical system 110 translates surgical tools 1050 through the operative space more quickly when the surgical tools 1050 are farther from the patient and more slowly when the surgical tools 1050 are closer to the patient based on the same input received from the input control devices 136 (e.g., the amount of force being exerted on the input control devices 136 by the surgeon). Because the movement of the robotic surgical system 110 is adjustably related to the input from the input control devices 136, the control space can be scaled to the operative space of the robotic surgical system 110. In particular, the robotic surgical system 110 can be configured to scale its movement such that it translates the surgical tools 1050 more quickly when the surgical tools 1050 are far from the patient and then automatically scales its movement as the surgical tools 1050 approach the patient to avoid risking contact with the patient. Further, decreasing the rate at which the robotic surgical system 110 moves the surgical tools 1050 when the surgical tools 1050 are in close proximity to the patient has the additional benefit of reducing the amount of movement caused by inadvertent control inputs to the robotic surgical system 110, which can prevent damage to the patient caused by inadvertent contact between the robotic surgical system components and the patient.

Various aspects of the present disclosure discuss movement of a robotic surgical system component such as a surgical tool 1050, which may include an end effector 1052 (FIG. 7) or another component of the robotic surgical system near a patient. Various aspects of the present disclosure also discuss a distance $d_t$ between the robotic surgical system component and the patient. For the purpose of these discussions, the term patient comprises any tissue of the patient from which a distance to the surgical tool is determined. In at least one example, the tissue of the patient is a tissue along the path of the surgical tool. In at least one example, the tissue of the patient is a tissue that is ultimately contacted and/or treated by the surgical tool. In at least one example, the tissue of the patient is a tissue within the patient such as, for example, a tissue within a patient cavity. In at least one example, the tissue of the patient is any critical tissue, as described herein. In certain examples, the term patient encompasses an object such as, for example, a tag or another surgical tool or component of the robotic surgical system that is positioned near, on, or within the patient.

Various processes can be implemented to modify the movement of the robotic surgical system as a function of the distance between a component (e.g., an end effector) of the robotic surgical system and the patient. For example, FIGS. 14 and 15 are logic flow diagrams of processes 2000, 2050 for controlling the movement of a robotic surgical system, in accordance with at least one aspect of the present disclosure. The processes 2000, 2050 can be executed by a control circuit of a computer system, such as the processor 158 of the robotic surgical system 150 illustrated in FIG. 3 or the control circuit 1532 of the control system 1533 illustrated in FIG. 9. Accordingly, the processes 2000, 2050 can be embodied as a set of computer-executable instructions stored in a memory 1534 (FIG. 9) that, when executed by the control circuit 1532, cause the computer system (e.g., the control system 1533) to perform the described steps. Further, although the processes 2000, 2050 depicted in FIGS. 14 and 15 are described as being executed by a control circuit 1532 of a control system 1533, this is merely for brevity, and it should be understood that the depicted processes 2000, 2050 can be executed by circuitry that can include a variety of hardware and/or software components and may be located in or associated with various systems integral or connected to a robotic surgical system 150.

In some aspects, the control circuit 1532 can scale the movement of the robotic surgical system according to whether the measured distance between the robotic surgical system and/or a component thereof meets or exceeds one or more thresholds. For example, FIG. 14 illustrates a process 2000 for scaling the motion of the robotic surgical system based on the distance between the robotic surgical system and/or a component thereof relative to one threshold. The control circuit 1532 can be coupled to a motor of the robotic surgical system 150 that may cause a component of the robotic surgical system 150 such as, for example, a surgical tool 1050 to move in response to an instrument motion control signal received 2002 through the input control device 1000. In one aspect, the input control device 1000 and/or robotic surgical system 150 can be operable in gross or fine (i.e., precision) motion control modes, as described above under the heading INPUT CONTROL DEVICES.

Accordingly, a control circuit 1532 executing the process 2000 determines 2004 the distance $d_t$ between a component of the robotic surgical system 150, such as a surgical tool 1050 or an end effector 1052 thereof, and the tissue of the patient. The control circuit 1532 can measure the distance $d_t$ utilizing TOF, structured light, and other such techniques via the visualization system 1500 (FIG. 8) described above under the heading SURGICAL VISUALIZATION SYSTEMS, for example. In one aspect, the control circuit 1532 can receive the distance $d_t$ from a distance sensor system 1504 (FIG. 8), which can include a TOF sensor or other such distance sensors, as described above.

Accordingly, the control circuit 1532 compares 2006 the distance $d_t$ to a threshold distance to determine whether the robotic surgical system component is within the threshold distance to the patient. The control circuit 1532 can, for example, retrieve the threshold distance from a memory. In one aspect, the control circuit 1532 determines whether the distance $d_t$ is greater than or equal to the threshold distance.

If the distance $d_t$ is greater than or equal to the threshold distance (i.e., the robotic surgical system component is farther away from the patient than the threshold distance), then the process 2000 proceeds along the YES branch and the control circuit 1532 scales 2008 the amount of movement of the robotic surgical system 150 caused by the gross motion controls of the input control device 1000 according to the distance $d_t$. In one example, the control circuit 1532 activates a gross motion mode, which can scale the sensitivity of the movement generated by the robotic surgical system 150 with respect to the user input received via the input control device 1000. As another example, the control circuit 1532 can scale the control signal generated by the input control device 1000 or scale the amount of force required to be exerted by the user on the input control device 1000 to cause the robotic system to move a set distance or speed.

If the distance $d_t$ is not greater than or equal to the threshold distance (i.e., the robotic surgical system component is at the threshold distance from the patient or closer to the patient than the threshold distance), then the process 2000 proceeds along the NO branch and the control circuit 1532 deactivates 2010 gross motion of the robotic surgical system or otherwise prevents the robotic surgical system 150 from being operated in a gross motion mode. In one aspect, the control circuit 1532 changes an internal setting of the robotic surgical system 150 from a gross motion mode to a fine-movement mode. Regardless of the evaluation of the distance $d_t$, the control circuit 1532 can continue to monitor the position of the robotic surgical system component and the patient and control the movement of the robotic surgical system 150 accordingly throughout the course of the surgical procedure.

As another example, FIG. 15 illustrates a process 2050 for scaling the motion of the robotic surgical system 150 based on the distance between the robotic surgical system 150 and/or a component thereof relative to multiple thresholds. The control circuit 1532 can take a variety of different actions according to the distance $d_t$ relative to particular thresholds.

Accordingly, as described above with respect to the process 2050 illustrated in FIG. 15, the control circuit 1532 receives 2052 an instrument motion control signal from, for example, a robotic input control device 1000 and determines 2054 the distance $d_t$ between a component of the robotic surgical system and a tissue of the patient.

Accordingly, the control circuit 1532 compares 2056 the distance $d_t$ to a first threshold distance $D_1$ to determine whether the robotic surgical system component is within the threshold distance $D_1$ to the patient. In one aspect, the control circuit 1532 determines whether the distance $d_t$ is greater than or equal to the threshold distance $D_1$. If the distance $d_t$ is greater than or equal to the threshold distance $D_1$ (i.e., the robotic surgical system component is farther away from the patient than the threshold distance $D_1$), then the process 2050 proceeds along the YES branch and the control circuit 1532 causes the robotic surgical system component to scale 2058 the movement of the robotic surgical system 150 such as, for example, by activating the gross motion mode, as described above. In various aspects, the control circuit 1532 can cause the robotic surgical system to operate at a default speed or cause the motion controls to operate at the default sensitivity in the gross motion mode, wherein the default speed and/or sensitivity are scaled in accordance with predetermined parameters of the gross motion mode. If the distance $d_t$ is not greater than the threshold distance $D_1$ (i.e., the robotic surgical system component is at the threshold distance $D_1$ from the patient or closer to the patient than the threshold distance $D_1$), then the process 2050 proceeds along the NO branch.

Accordingly, the control circuit 1532 compares 2060 the distance $d_t$ to a second threshold distance $D_2$ to determine whether the robotic surgical system component is within the threshold distance $D_2$ to the patient. In one aspect, the control circuit 1532 determines whether the distance $d_t$ is greater than the threshold distance $D_2$. If the distance $d_t$ is greater than the threshold distance $D_2$, then the process 2050 proceeds along the YES branch and the control circuit 1532 adjusts 2062 the scaling of the gross motion controls according to the distance $d_t$.

If the distance $d_t$ is not greater than the threshold distance $D_2$, then the process 2050 proceeds along the NO branch and the control circuit 1532 deactivates 2064 gross motion of the robotic surgical system, as described above. In one aspect, the control circuit 1532 changes an internal setting of the robotic surgical system 150 from a gross motion mode to a fine-movement mode. Regardless of the evaluation of the distance $d_t$, the control circuit 1532 can continue to monitor the position of the robotic surgical system component and the patient and control the movement of the robotic surgical system accordingly throughout the course of the surgical procedure.

The values of the thresholds distances $D_1$ and/or $D_2$ can be stored in a memory of the control unit 1532 and can be accessed by a processor executing the process 2050 and/or the process 2000. Although the processes 2000 and 2050 use the inequality symbol "≥" in comparing the distance $d_t$ to threshold, this is not limiting. In alternative embodiments, the processes 2000, 2050 may use the inequality symbol ">" instead of the inequality symbol "≥". For example, in the process 2000, the scaling 2008 can be limited to situations where the distance $d_t$ is greater than the threshold, and the deactivation 2010 of the scaling can be triggered by any distance $d_t$ that is less than or equal to the threshold.

FIG. 16 is a graph 2100 of the relationship between input from the input control device 1000 and the movement of the robotic surgical system 150 based on the proximity of the surgical tool 1050 to a tissue of a patient, according to a prophetic implementation of the process 2050. In the graph 2100, the vertical axis 2102 represents the user input force required to be exerted on the input control device 1000 to move the robotic surgical system 150 a particular distance or at a particular speed, the horizontal axis 2104 represents the distance $d_t$, and the line 2106 represents the change in the user input force required to move the robotic surgical system 150 according to the process 2050 illustrated in FIG. 15.

In various examples, the input control device 1000 includes a sensor arrangement 1048 (FIG. 9), which may include one or more force sensors for assessing the user input force. In such examples, the sensor arrangement 1048 transmits an instrument motion control signal to the control circuit 1532 commensurate with the user input force detected by the sensor arrangement 1048.

Notably, aspects of the processes for controlling the movement of a robotic surgical system 150 discussed herein that incorporate or utilize multiple thresholds can define various zones for particular parameters (e.g., the distance $d_t$) in which the control system 1533 controls the robotic surgical system differently. For example, the thresholds $D_1$, $D_2$ define various zones 2110, 2112, 2114 in which the control system 1533 causes the robotic surgical system 150 to exhibit different behaviors or properties. For example, a control circuit 1532 executing the process 2050 can cause the robotic surgical system 150 to operate in a default gross motion mode within the zone 2114, an intermediate or adjustable gross motion mode within the zone 2112, and/or a fine-movement mode within the zone 2110.

In one example, the default gross motion mode is applied to the movement of the surgical tool while the distance $d_t$ between the surgical tool and the tissue of the patient is greater than or equal to the threshold distance $D_2$. Additionally, or alternatively, the adjustable gross motion mode is applied to the movement of the surgical tool while the distance $d_t$ between the surgical tool and the tissue of the patient is between the threshold distances $D_1$ and $D_2$. Additionally, or alternatively, the fine-movement mode is applied to the movement of the surgical tool while the distance $d_t$ between the surgical tool and the tissue of the patient is less than the threshold distance $D_1$.

As described above, the movement of the surgical tool is scaled to the user input force according to the distance $d_t$. In various examples, the movement of the surgical tool is scaled to the user input force in a manner that generates a greater speed for a given user input force within the zone 2114 in comparison to the same given force within zones 2112 and 2110. In other words, the movement of the surgical tool is scaled to the user input force in a manner that requires a lesser user input force to move the surgical tool at a particular rate of motion within the zone 2114 in comparison to the zones 2112 and 2110.

In various examples, the movement of the surgical tool is scaled to the user input force in a manner that generates a lesser speed for a given user input force within the zone 2110 in comparison to the same given force within zones 2112 and 2114. In other words, the movement of the surgical tool is scaled to the user input force in a manner that requires a greater user input force to move the surgical tool at a particular rate of motion within the zone 2110 in comparison to the zones 2112 and 2114.

In various examples, a default maximum scale factor or scale factor range is utilized to scale the movement of the surgical tool to the user input force in the zone 2114. Additionally, or alternatively, a default minimum scale factor or scale factor range is utilized to scale the movement of the surgical tool to the user input force in the zone 2110. Additionally, or alternatively, an adjustable scale factor or scale factor range is utilized to scale the movement of the surgical tool to the user input force in the zone 2112.

In various aspects, the control circuit 1532 can adjust the scaling of the movement of the surgical tool to the user input force via a linear, or substantially linear, algorithm or other types of algorithms. Still further, the control circuit 1532 can cause the robotic surgical system 150 to deactivate the gross motion controls, i.e., only permit fine motion of the surgical system 150, when the robotic surgical system component is within a third zone 2110.

Although the examples described above track a user input force and scale the movement of the surgical tool to the user input force, it is foreseeable to track a user input movement and scale the movement of the surgical tool to the user input movement or to the combined user input force and user input movement, as detected by the input control device 1000.

In effect, a control circuit 1532 executing the processes 2000, 2050 permits gross motion by the robotic surgical system 150 when a component thereof is far from the patient and enforces finer movement by the robotic surgical system 150 when the component is near the patient. By adjustably scaling the movement of the robotic surgical system 150 according to the proximity to the patient, the robotic surgical system 150 can allow quicker movement of surgical tools 1050 controlled by the robotic surgical system 150 through the unoccupied areas that are far from the patient so that a surgeon does not have to repeatedly clutch out of the controls when trying to move the surgical tools 1050 relatively large distances to the patient. Further, the robotic surgical system 150 can automatically switch to a fine or precision movement mode as the surgical tools 150 approach the patient.

In various aspects, the gross motions described in the present disclosure are gross translational motions characterized by speeds selected from a range of about 3 inches/second to about 4 inches/second. In at least one example, a gross translational motion, in accordance with the present disclosure, is about 3.5 inches/second. In various aspects, by contrast, the fine motions described in the present disclosure can be fine translational motions characterized by speeds less than or equal to 1.5 inch/second. In various aspects, the fine motions described in the present disclosure can be fine translational motions characterized by speeds selected from a range of about 0.5 inches/second to about 2.5 inches/second.

In various aspects, the gross motions described in the present disclosure are gross rotational motions characterized by speeds selected from a range of about 10 radians/second to about 14 radians/second. In at least one example, a gross rotational motion, in accordance with the present disclosure, is about 12.6 radians/second. In various aspects, by contrast, the fine motions described in the present disclosure can be fine rotational motions characterized by speeds selected from a range of about 2 radians/second to about 4 radians/ second. In at least one example, a fine rotational motion, in accordance with the present disclosure, is about 2.3 radians/second.

In various aspects, the gross motions of the present disclosure are two to six times greater than the fine motions. In various aspects, the gross motions of the present disclosure are three to five times greater than the fine motions.

Scaling Camera Magnification According to Tissue Proximity

Many robotic surgical systems force users to manually adjust the magnification or FOV of the visualization system during the course of a surgical procedure. However, this can force users to divert their attention from the surgical task at hand, which can cause mistakes during the surgical procedure and force surgeons to reorient themselves each time the magnification is changed, which can take up time during the surgical procedure. Therefore, it can be desirable for the visualization system 1500 associated with a robotic surgical system 150 to automatically adjust or scale its magnification depending upon the needs of the surgeon during the surgical procedure.

Accordingly, a visualization system 1500 for a robotic surgical system 150 can be configured to control the magnification of a camera 1520 (FIG. 8) in use during the surgical procedure as a function of the distance between a robotic surgical system component, such as a surgical tool 1050 or an end effector 1052 thereof, and the patient. For example, FIG. 17 is a logic flow diagram of a process 2200 for controlling a visualization system 1500 of a robotic surgical system, in accordance with at least one aspect of the present disclosure. The process 2200 can be executed by a control circuit of a computer system, such as the processor 158 of the robotic surgical system 150 illustrated in FIG. 3 or the control circuit 1532 of the control system 1533 illustrated in FIG. 9. Accordingly, the process 2200 can be embodied as a set of computer-executable instructions stored in a memory 1534 (FIG. 9) that, when executed by the control circuit 1532, cause the computer system (e.g., the control system 1533) to perform the described instructions. Further, although the process 2200 depicted in FIG. 17 is described as being executed by a control circuit 1532 of a control system 1533, this is merely for brevity, and it should be understood that the depicted process 2200 can be executed by circuitry that can include a variety of hardware and/or software components and may be located in or associated with various systems integral or connected to a robotic surgical system 150.

Accordingly, a control circuit 1532 executing the process 2200 determines 2202 the distance $d_t$ between a component of the robotic surgical system 150, such as a surgical tool 1050 or an end effector 1052 thereof, and the patient. The control circuit 1532 can measure the distance $d_t$ utilizing TOF, structured light, and other such techniques via the visualization system 1500 described above under the heading SURGICAL VISUALIZATION SYSTEMS, for example.

Accordingly, the control circuit 1532 sets 2204 the magnification of the visualization system 1500 based on the distance $d_t$. The relationship between the visualization system magnification and the distance $d_t$ can be defined algorithmically, represented by a series of magnification values stored in a lookup table or other storage that are indexed according to distance values and so on. For example, the relationship between the distance $d_t$ and the visualization system magnification can be linear, nonlinear, binary, and so on. Further, the relationship between the distance $d_t$ and the visualization system magnification can correspond to modes or settings that are selectable by users of the visualization system 1500. The control circuit 1532 can be configured to continue to monitor the position of the robotic surgical system component and the patient and control the visualization system 1500 accordingly throughout the course of the surgical procedure.

FIGS. 18 and 19 are graphs 2250, 2300 of the magnification and FOV, respectively, of the visualization system 1500 versus the distance $d_t$ between the robotic surgical system component and the patient according to prophetic implementations of the process 2200 illustrated in FIG. 17. In the first graph 2250, the vertical axis 2252 represents the magnification of the visualization system 1500 and the horizontal axis 2254 represents the distance $d_t$ between the robotic surgical system component and the patient. The first line 2256 and the second line 2258 represent the relationship between magnification and the distance $d_t$ in different implementations of the process 2200. In the implementation represented by the first line 2256, the visualization system magnification is linearly related to the distance $d_t$ such that the magnification increases linearly as the distance $d_t$ decreases (as the robotic surgical system component approaches the patient tissue). Accordingly, the control circuit 1532 can set 2204 the visualization system magnification based on the distance $d_t$ utilizing a linear algorithm, for example. In the implementation represented by the second line 2258, the visualization system magnification is related to the distance $d_t$ by a binary relationship, i.e., once the distance $d_t$ reaches a threshold value $D_{z1}$, the magnification increases from a first value to a second value. Accordingly, the control circuit 1532 can set 2204 the visualization system magnification based on the distance $d_t$ utilizing a step function where the control circuit 1532 sets 2204 the visualization system 1500 to a first magnification if $d_t$ is less than $D_{z1}$ or a second magnification if $d_t$ is greater than or equal to $D_{z1}$.

In the second graph 2300, the vertical axis 2302 represents the FOV of the visualization system 1500 and the horizontal axis 2304 represents the distance $d_t$ between the robotic surgical system component and the patient. The third line 2306 represents the relationship between magnification and the distance $d_t$ in another implementations of the process 2200. In the implementation represented by the third line 2306, the visualization system FOV is nonlinearly related to the distance $d_t$ such that the FOV gradually decreases (i.e., the magnification increases) as the distance $d_t$ decreases (as the robotic surgical system component approaches the patient tissue) until the distance $d_t$ reaches a threshold distance $D_{z2}$. At and/or below the threshold distance $D_{z2}$, the visualization system magnification is set to a particular predetermined value.

Accordingly, the control circuit 1532 can set 2204 the visualization system FOV based on the distance $d_t$ by comparing the distance $d_t$ to the threshold value $D_{z2}$ and either setting the visualization system FOV to a calculated FOV value if the distance $d_t$ is greater than or equal to the threshold $D_{z2}$ or setting the visualization system FOV to a predetermined FOV value if the distance $d_t$ is less than or equal to the threshold $D_{z2}$. This implementation causes the visualization system 1500 to gradually decrease its FOV as a surgical tool 1050 (or other robotic system component) approaches the patient and then, once the surgical tool 1050 is at or closer than a particular distance from the patient, set the FOV to a particular value so that further movement of the surgical tool 1050 within a zone 2301 defined by the threshold distance $D_{z2}$ thereby maintaining the FOV within the zone 2301.

In effect, a control circuit 1532 executing the process 2200 automatically sets the magnification of the visualization system 1500 to an appropriate level based on the proximity of a surgical tool 1050 or another robotic surgical system component to the patient. When the surgical tool 1050 is far from the patient, the visualization system 1500 can be set to a low magnification to provide a large FOV to the surgeon suitable for visualizing gross motions by the surgical tool 1050 and viewing anatomy adjacent to the surgical site. Conversely, when the surgical tool 1050 is in close proximity to the patient, the visualization system 1500 can be set to a high magnification to provide a tight FOV suitable for performing precise and delicate movements with the surgical tool 1050. In various aspects, the FOV is adjusted by changing the magnification.

Location Tagging

During a surgical procedure, there may be particular structures or landmarks that a surgeon may wish to return to throughout the procedure or that the surgeon desires to be particularly cautious of when moving a surgical tool 1050 near (e.g., a structure that may shift or move during the surgical procedure). Accordingly, in some aspects the robotic surgical system 150 can be configured to allow users to tag or select certain locations prior to and/or during the surgical procedure. In various aspects, tagged locations can be returned to automatically during the surgical procedure, which can reduce the amount of physical manipulation that surgeons are required to perform, and/or define zones through which the robotic surgical system 150 is to move any surgical tools 1050 or other components more slowly, which can improve the safety in using the robotic surgical system 150.

In one aspect, the robotic surgical system 150 provides a user interface via, for example, a display 160 (FIG. 3) that users can utilize to mark particular locations or other points of interest during a surgical procedure. Once marked, the robotic surgical system 150 can automatically return to the selected location or perform various functions when a surgical tool 1050 or another component of the robotic surgical system 150 is located within a zone defined by the selected location.

FIGS. 20 and 21 are various views of a robotic surgical system user interface for tagging locations, in accordance with at least one aspect of the present disclosure. A user can tag a location by, for example, selecting a location on a display 160 and displaying a video feed from the surgical procedure and/or other information captured by the visualization system 1500. The display 160 can include, for example, a touchscreen display on which users can directly select a location. Once selected, the control circuit 1532 can determine the coordinates of the tissue located at the selected point by, for example, mapping the surface of the tissue and determining what location on the mapped tissue the selected point corresponds to using one or more of the aforementioned techniques for mapping a tissue surface. The control circuit 1532 can then save the coordinates of the selected location (e.g., in the memory 1534). In one aspect, the control circuit 1532 can be configured to control the robotic surgical system 150 to move the surgical tool 1050 to a position that corresponds to the coordinates for the selected location. For example, the control circuit 1532 can be configured to move the surgical tool 1050 such that it is positioned above the coordinates for the selected location.

In one aspect, the robotic surgical system 150 can be configured to define zones around the selected or tagged locations. The tagged zones can be defined algorithmically based upon the tagged location selected by the user, tissue parameters associated with the tissue at or adjacent to the tagged location, and so on. In the aspect illustrated in FIGS. 20 and 21, the tagged location 2452 is the point selected by the user, as described above, and the tagged zone 2450 is the zone defined around the tagged location 2452. In the depicted aspect, the tagged zone 2450 is defined as the zone of height H above the surface of the tissue 2460, length L along the surface of the tissue 2460, and width W along the surface of the tissue 2460, wherein the tagged location 2452 is positioned, or substantially positioned, at the midpoint of the tagged zone 2450. Accordingly, the tagged zones 2450 are defined based upon the location of the particular tagged location 2452. Accordingly, the tagged zones 2450 can be defined and updated in real time during a surgical procedure and displayed on a display 160 or another visualization system. In some aspects, the tagged zones 2450 and/or tagged locations 2452 can be overlaid on the video feed relayed from a camera 1520 or another component of the visualization system 1500.

In another aspect, the tagged zones 2450 can be created preoperatively, rather than intraoperatively, by scanning the tissue surface via a preoperative CT scan, MRI scan, or other scanning technique. A control system can then model the tissue surface and any locations of interest can be tagged. Thereafter, the control system can save the preoperatively defined tagged zones 2450 and control the function(s) of the robotic surgical system 150 according to the predefined tagged zones 2450 during the course of the surgical procedure.

In one aspect, the robotic surgical system 150 can be configured to change its functionality when a surgical tool 1050 controlled by the robotic surgical system 150 is at or within the tagged zone. For example, FIG. 22 is a logic flow diagram of a process 2400 for controlling a robotic surgical system 150 according to whether a component thereof is positioned within a tagged zone, in accordance with at least one aspect of the present disclosure. The process 2400 can be executed by a control circuit of a computer system, such as the processor 158 of the robotic surgical system 150 illustrated in FIG. 3 or the control circuit 1532 of the control system 1533 illustrated in FIG. 9. Accordingly, the process 2400 can be embodied as a set of computer-executable instructions stored in a memory 1534 (FIG. 9) that, when executed by the control circuit 1532, cause the computer system (e.g., the control system 1533) to perform the described steps. Further, although the process 2400 depicted in FIG. 22 is described as being executed by a control circuit 1532 of a control system 1533, this is merely for brevity, and it should be understood that the depicted process 2400 can be executed by circuitry that can include a variety of hardware and/or software components and may be located in or associated with various systems integral or connected to a robotic surgical system 150.

Accordingly, a control circuit 1532 executing the process 2400 determines 2402 the position of a surgical tool 1050 controlled by the robotic surgical system 150 via the techniques discussed above under the heading SURGICAL VISUALIZATION SYSTEMS, for example. Accordingly, the control circuit 1532 determines 2404 whether the position of the surgical tool 1050 lies at or within one of the tagged zones 2450 (which can be defined preoperatively or intraoperatively). If the surgical tool position does intersect with one of the tagged zones 2450, the process 2400 proceeds along the YES branch and the control circuit 1532 sets 2406 the robotic surgical system 150 to a fine or precision movement mode (e.g., from a gross motion mode). If the surgical tool position does not intersect with one of the tagged zones 2450, the process 2400 proceeds along the NO branch and the control circuit 1532 operates 2408 normally or according to other processes. Regardless, the control circuit 1532 can continue monitoring the position of the surgical tool 1050 to determine whether the surgical tool 1050 is located within a tagged zone 2450 and controlling the robotic surgical system 150 accordingly throughout the surgical procedure.

In effect, a control circuit 1532 executing the process 2400 switches the robotic surgical system 150 into a fine-movement mode when a surgical tool 1050 enters the area around a location of interest that has been tagged by a user. Therefore, users can tag particular locations near which they want the robotic surgical system 150 to be particularly cautious in moving a surgical tool 1050 or where more precise control of the robotic surgical system 150 is otherwise desired.

Scaling Surgical System Movement According to Camera Magnification

In robotic surgery, properly scaling the motion of the surgical tool relative to surgeon input motion is critical for two reasons. First, it is very important that that the surgeon is able to accurately move the surgical tools during a surgical procedure because many surgical tasks require precise motions to complete, and inaccurate movements with surgical tools risk causing harm to the patient. Second, the overall user experience associated with the robotic surgical system must be intuitive and comfortable because unintuitive controls can create more risks for mistakes and can cause surgical procedures to take more time, thereby requiring that the patient be under anesthesia for a longer period of time and potentially leading to surgeon fatigue. Therefore, it can be desirable to scale the robotic surgical system motion to the surgeon input motion in a manner that promotes an intuitive user experience in controlling the robotic surgical system.

Some evidence has indicated that scaling the surgeon input motion according to the perceived on-screen motion of the surgical tools makes for an intuitive user experience in controlling the surgical tools. The perceived on-screen motion of the surgical tools is affected by the magnification and other lens parameters associated with the visualization system 1500 or a camera 1520 thereof. Accordingly, various processes can be implemented to correlate the robotic surgical system output motion scaling and the magnification of the visualization system 1500. For example, FIG. 23 is a logic flow diagram of a process 2500 for controlling the movement of a robotic surgical system according to camera magnification. The process 2500 can be executed by a control circuit of a computer system, such as the processor 158 of the robotic surgical system 150 illustrated in FIG. 3 or the control circuit 1532 of the control system 1533 illustrated in FIG. 9. Accordingly, the process 2500 can be embodied as a set of computer-executable instructions stored in a memory 1534 (FIG. 9) that, when executed by the control circuit 1532, cause the computer system (e.g., the control system 1533) to perform the described steps. Further, although the process 2500 depicted in FIG. 23 is described as being executed by a control circuit 1532 of a control system 1533, this is merely for brevity, and it should be understood that the depicted process 2500 can be executed by circuitry that can include a variety of hardware and/or software components and may be located in or associated with various systems integral or connected to a robotic surgical system 150.

Accordingly, the control circuit 1532 executing the process 2500 determines 2502 the current magnification of the visualization system 1500. In one aspect, the visualization system 1500, the camera 1520, or a control system thereof is configured to continually update a memory or database with the current magnification value at which the visualization system 1500 is set. In such an aspect, the control circuit 1532 can determine 2502 the visualization system 1500 magnification by retrieving the magnification value reflecting the current magnification of the visualization system 1500 from the memory or database. In another aspect, the control circuit 1532 can be configured to determine 2502 the visualization system 1500 magnification from parameters associated with the visualization system 1500. For example, the visualization system 1500 magnification can be based on the distance from the endoscope camera lens to the subject tissue, the distance of a surgical tool to a subject tissue, and/or camera lens parameters.

In various aspects, the control circuit 1532 is configured to set the visualization system 1500 magnification based on the distance between the camera 1520 of the visualization system 1500 and the patient's tissue as a proxy for the actual visualization system magnification. Furthermore, the control circuit 1532 can be configured to set the visualization system 1500 visual scaling based on the motion scaling of the camera 1520 relative to the patient's tissue. In various aspects, as the camera 1520 moves closer to the subject tissue, which causes the image observed by the camera 1520 to be magnified, the motion scaling factor decreases to enable precise motions thereby maintaining, or substantially maintaining, a 1-to-1 relationship between input motions with perceived on-screen motions. Other scaling factors can also be applied based on other measured distances.

The control circuit 1532 can determine the camera-to-tissue distance by, for example, utilizing structured light and/or other techniques described above under the heading SURGICAL VISUALIZATION SYSTEMS to calculate the distance between the visualization system 1500 and the tissue and/or critical structures. This or other visualization system 1500 parameters can then be utilized as a baseline for scaling the output motion of the robotic system based on the surgeon input motion.

Accordingly, the control circuit 1532 scales 2504 the movement of the robotic surgical system component based on the actual or estimated visualization system magnification. In one aspect, the control circuit 1532 can scale 2504 the robotic surgical system component movement by applying a scale factor that is applied to the generated control signals for controlling the movement of the various components of the robotic surgical system component to produce the robotic surgical system output motion. The relationship between the visualization system magnification and the scaling applied to the robotic surgical system component movement can be defined algorithmically (which can be computed at run-time or pre-calculated for particular values), represented by a series of movement scale factors stored in a (e.g., prefetched) lookup table or other storage that are indexed according to magnification values, and so on. In various aspects, the control circuit 1532 can continue monitoring the visualization system magnification and adjusting the output movement of the robotic surgical system component accordingly throughout a surgical procedure.

FIG. 24 is a graph 2550 of the magnification of the camera assembly versus the distance between the robotic surgical system component and the patient according to prophetic implementations of the process 2500 illustrated in FIG. 23. The vertical axis 2552 represents the movement scale factor µ and the horizontal axis 2554 represents the magnification of the visualization system 1500. As represented in this particular graph 2550, as the magnitude of the scale factor µ increases vertically along the vertical axis 2552, the relative output movement of the robotic surgical system is decreased, requiring more input motion by the user to move the surgical tools 1050 a smaller distance. The first line 2560 and the second line 2562 represent examples of the relationship between the movement scale factor µ and the visualization system magnification in different implementations of the process 2550.

In one aspect, represented by the first line 2560, there is a non-linear relationship between the movement scale factor µ and the visualization system magnification. In another aspect, represented by the second line 2562, there is a linear relationship between the movement scale factor µ and the visualization system magnification. In this aspect, the magnitude of scaling of the robotic surgical system component movement decreases as the robotic surgical system component, for example, the camera 1520, approaches the tissue and/or critical structure. In various aspects, the amount or character (e.g., linear or non-linear) of scaling of the robotic surgical system component movement relative to the visualization system magnification can be selected by the user. In various other aspects, various other parameters associated with the visualization system 1500 and/or distances between the patient and the robotic surgical system components are selected by the user.

In effect, a control circuit 1532 executing the process 2500 causes the movement of the robotic surgical system component to decrease in response to input from an input control device 1000 (i.e., become more precise) as the magnification of the visualization system 1500 increases. In various aspects, the magnification of the visualization system 1500 can be retrieved from a memory or determined indirectly by monitoring a parameter associated with the visualization system 1500, such as the distance between a camera 1520 of the visualization system 1500 and the tissue (because as the camera 1520 moves closer to the tissue, the image produced by the camera 1520 is magnified). Therefore, the output movement of the robotic surgical system is intuitively scaled to the perceived on-screen motion of the robotic system component.

Locking End Effector According to Tissue Proximity

Various drive mechanisms for manipulating a robotic surgical tool, such as cable drive mechanisms, are disclosed in U.S. Pat. No. 8,224,484, titled METHODS OF USER INTERFACE WITH ALTERNATE TOOL MODE FOR ROBOTIC SURGICAL TOOLS, which is hereby incorporated by reference herein in its entirety. Articulating, manipulating, or otherwise actuating an end effector 1052 (FIG. 7) while moving the end effector 1052 toward a patient, for example, in gross motion mode, may cause the end effector 1052 to unintentionally contact or engage a tissue of the patient and/or other surgical tools positioned along the path of the end effector 1052 and can place strain on the drive mechanism(s) of the surgical tool 1050 and/or robotic surgical system 150 effectuating those movements. The strain placed on the cables or other drive mechanism components can, over time, cause those components to fail, which can cause damage to the surgical tool 1050 and/or robotic surgical system 150 and necessitate costly and time-consuming repairs.

The present disclosure provides various solutions for reducing the unintentional contact between a moving end effector 1052 and a tissue of the patient and/or other surgical tools and for minimizing the amount of stress placed on the drive mechanism for controlling an end effector 1052 in order to prolong the lifespan of the surgical tool 1050 and/or robotic surgical system 150.

Various processes are implemented to reduce the unintentional contact between a moving end effector 1052 and a tissue of the patient and/or other surgical tools, and to minimize the stress placed on the end effector drive mechanism(s), by maintaining the end effector 1052 in a locked configuration in a position where the drive mechanism(s) are unstressed or minimally stressed when there would generally be no need to actuate the end effector 1052. Maintaining the end effector 1052 in an unstressed position when there would be no need to actuate the end effector 1052 reduces the overall amount of stress applied to the end effector drive mechanism(s) by reducing the number of instances during which the drive mechanisms are being stressed without sacrificing the usability of the end effector 1052.

FIGS. 25 and 26 are logic flow diagrams of processes for controlling an end effector to minimize unintentional contact or engagement between a moving end effector 1052 and a tissue of the patient and/or other surgical tools positioned along the path of the end effector 1052, in accordance with at least one aspect of the present disclosure. FIGS. 25A and 26A are logic flow diagrams of processes for controlling an end effector to reduce the amount of stress applied to the end effector drive mechanism(s), in accordance with at least one aspect of the present disclosure.

The processes 2600, 2601, 2650, 2651 can be executed by a control circuit of a computer system, such as the processor 158 of the robotic surgical system 150 illustrated in FIG. 3 or the control circuit 1532 of the control system 1533 illustrated in FIG. 9. Accordingly, the processes 2600, 2601, 2650, 2651 can be embodied as a set of computer-executable instructions stored in a memory 1534 (FIG. 9) that, when executed by the control circuit 1532, cause the computer system (e.g., the control system 1533) to perform the described steps. Further, although the processes 2600, 2601, 2650, 2651 depicted in FIGS. 25-26A are described as being executed by a control circuit 1532 of a control system 1533, this is merely for brevity, and it should be understood that the depicted processes 2600, 2601, 2650, 2651 can be executed by circuitry that can include a variety of hardware and/or software components and may be located in or associated with various systems integral or connected to a robotic surgical system 150.

In certain aspects illustrated in FIGS. 25 and 25A, the processes 2600, 2601 control whether the end effector 1052 is locked or unlocked according to the distance $d_t$ between the end effector 1052 and the patient. Accordingly, a control circuit 1532 executing the processes 2600, 2601 determines 2602 the distance $d_t$ between the end effector 1052 and the patient. The control circuit 1532 can measure the distance $d_t$ utilizing TOF, structured light, and other such techniques via the visualization system 1500 described under the heading SURGICAL VISUALIZATION SYSTEMS, for example.

Accordingly, the control circuit 1532 compares 2604 the distance $d_t$ to a threshold distance. The control circuit 1532 can, for example, retrieve the threshold distance from a memory. In one aspect, the control circuit 1532 can determine whether the distance $d_t$ is greater than or equal to the threshold distance. The threshold distance can correspond to the distance at which the control of the surgical tool is change from a gross control mode to a fine control mode. If the distance $d_t$ is greater than or equal to the threshold, then the process 2600 proceeds along the YES branch and the control circuit 1532 causes the end effector 1052 to be in a locked 2606 configuration. If the distance $d_t$ is less than the threshold, then the process 2600 proceeds along the NO branch and the control circuit 1532 unlocks 2608 the end effector 1052.

In the process 2601, however, an additional inquiry is made as to whether 2603 the end effector 1052 is in an unstressed position. If it is, the process 2601 proceeds along the YES branch and the control circuit 1532 locks 2607 the end effector 1052 in the unstressed position. However, if the process 2601 determines that the end effector 1052 is not in an unstressed position, the process 2601 proceeds along the NO branch and transitions 2605 the end effector 1052 to an unstressed position before locking 2607 the end effector 1052.

In other aspects illustrated in FIGS. 26 and 26A, the processes 2650, 2651 control whether the end effector 1052 is locked or unlocked according to whether the robotic surgical system 150 is in the gross motion mode. In some aspects, whether the robotic surgical system 150 is in the gross motion mode or the fine motion mode depends upon the position of the surgical tool 1050 relative to the patient, as discussed above with respect to FIGS. 14 and 15. Accordingly, a control circuit 1532 executing the processes 2650, 2651 determines 2654 whether the gross motion mode for the robotic surgical system 150 is activated. In one aspect, the control circuit 1532 can determine whether the robotic surgical system 150 is in the gross motion mode by retrieving a current state variable from a memory, an output of a state machine, and so on. In some aspects, a control system (such as the control system 1533) can maintain or update a current state variable or a state machine corresponding to the state (e.g., mode or position) of the robotic surgical system 150 and/or a surgical tool 1050 depending upon received input or actions taken by the robotic surgical system 150 and/or surgical tool 1050. Therefore, in these aspects, the control circuit 1532 can determine 2654 whether the robotic surgical system 150 is in the gross motion state by retrieving the value of this variable or the output the state machine.

If the robotic surgical system 150 is in the gross motion mode, the process 2650 proceeds along the YES branch and the control circuit 1532 locks 2656 the end effector 1052. If, however, the robotic surgical system 150 is not in the gross motion mode, then the process 2650 proceeds along the NO branch and the control circuit 1532 unlocks 2658 the end effector 1052.

In the process 2651, however, an additional inquiry is made as to whether 2653 the end effector 1052 is in an unstressed position. If it is, the process 2651 proceeds along the YES branch and the control circuit 1532 locks 2657 the end effector 1052 in the unstressed position. However, if the process 2651 determines that the end effector 1052 is not in an unstressed position, the process 2651 proceeds along the NO branch and transitions 2655 the end effector 1052 to an unstressed position before locking 2657 the end effector 1052.

In various aspects, a locked configuration is one that prevents the end effector 1052 for articulating, rotating, and/or actuating in response to a user input signal. The end effector 1052 can be locked mechanically, electronically via software control, or in any other manner that prevents control input (e.g., via the input control device 1000) from causing the end effector 1052 to articulate, rotate, and/or open and close its jaws. In particular, the end effector 1052 can be locked in a manner that prevents the cable assembly from straining or otherwise exerting force on the end effector 1052. As noted above, various systems and techniques for locking surgical drive mechanisms are described in U.S. Pat. No. 8,224,484. When the end effector 1052 is unlocked, it can be actuated or otherwise controlled by a user via, for example, an input control device 1000 to perform a surgical procedure, as described above under the heading INPUT CONTROL DEVICES.

In effect, the processes 2601, 2651 illustrated in FIGS. 25A and 26A can prevent or minimize the strain on the robotic drive mechanisms by locking the joint of the end effector 1052 in an unstressed position when there would generally be no need to actuate the end effector 1052, i.e., when the end effector 1052 is not in a close proximity to the patient. The unstressed position can include, for example, a position where the end effector 1052 is aligned with the longitudinal axis of the surgical tool shaft (i.e., the $X_T$ axis illustrated in FIG. 7).

Referring now to FIG. 27, in one aspect, the control circuit 1532 can further be configured to control an indicator 2660 based upon the lock state of the surgical tool 1050. In particular, the control circuit 1532 can be configured to shift the indicator 2660 between a first state and a second state according to whether the surgical tool 1050 is locked or unlocked. The indicator 2660 can include, for example, an LED configured to illuminate in different colors or in different patterns (e.g., flash when locked), a speaker assembly configured to emit sounds or alerts, or a display 160 (FIG. 3) configured to present icons, graphics, or textual alerts. The indicator 2660 can be disposed on or associated with the end effector 1052, the surgical tool 1050, the surgeon's console 116, 150 (FIGS. 1, 2, and 4), and so on. For example, a control circuit 1532 executing either or both of the processes 2600, 2650 can cause the indicator 2660 to illuminate in a first color when the surgical tool 1050 is locked 2606, 2656 and a second color when the surgical tool 1050 is unlocked 2608, 2658.

Selectable Variable Response of Shaft Motion

Referring now to FIG. 28, a graph 3001 represents four motion scaling profiles 3002, 3004, 3006, 3008 of the motion of a surgical tool 1050 (FIG. 7) with respect to a user input force 3010. The X-axis represents the user input force 3010 and the Y-axis represents corresponding rates of motion 3012 of the surgical tool 1050 in response to the user input force 3010 for each of the motion scaling profiles 3002, 3004, 3006, 3008.

In at least one example, the user input force 3010 is detected by a sensor arrangement 1048 (FIG. 9) in the base 1004 (FIG. 6) of the input control device 1000. When a user actuates the space joint 1006 (FIG. 6), the input control device 1000 transmits a motion control signal to the control circuit 1532 (FIG. 9), for example. In at least one example, the motion control signal represents the value(s) of the user input force(s) 3010 detected by the sensor arrangement 1048. The control circuit 1532 then causes the surgical tool 1050 to move in response to the motion control signal at rates of motion defined by the motion scaling profiles 3002, 3004, 3006, 3008.

As illustrated in FIG. 28, a given user input force 3010 yields a different rate of motion for each one of the motion scaling profiles 3002, 3004, 3006, 3008. For example, a first user input force F1 yields a first rate of motion V1 when the motion scaling profile 3004 is selected, and yields a second rate of motion V2 when the motion scaling profile 3002 is selected.

FIG. 29 illustrates an example motion-scaling profile selector 3014 in the form of a dial that includes four settings corresponding to the four motion scaling profiles 3002, 3004, 3006, 3008. A user may select a desired motion scaling profile through the selector 3014. Other forms of the selector 3014 are contemplated by the present disclosure. The selector 3014 can be integrated with the input control device 1000. For example, the actuation buttons 1026, 1028 (FIG. 6) of the input control device 1000 can be assigned to motion scaling profiles. In at least one example, the selector 3014 is in the form of a touch screen, which can be integrated with the input control device 1000. Alternatively, as illustrated in FIG. 30, the selector 3014 can be implemented in a pedal device 3016 that includes pedals 3018, 3020, 3022, for example, which can be assigned to various motion scaling profiles.

Although four motion scaling profiles are depicted in the graph 3001, more or less than four motion scaling profiles can be utilized. In one example, various motion scaling profiles (e.g. P1, P2, ..., Pn) can be stored in the memory 1534 (FIG. 9) in the form of a look up table 3024, as illustrated in FIG. 31. The look up table 3024 represents the user input forces (e.g. F1, F2, ..., Fn) and corresponding rates of motion ((e.g. $V_{a1}$, $V_{a2}$, ..., $V_{an}$), (e.g. $V_{b1}$, $V_{b2}$, ..., $V_{bn}$), (e.g. $V_{z1}$, $V_{z2}$, ..., $V_{zn}$)) that are available for each of the motion scaling profiles. Alternatively, various motion scaling profiles can be stored in the memory 1534 in the form of algorithms, or any other suitable form.

In the example of FIGS. 28 and 31, actual rates of motion 3012 of the surgical tool 1050 in response to user input forces 3010 are utilized to represent the motion scaling profiles 3002, 3004, 3006, 3008. In other examples, a multiplier or any other parameter of the motion of the surgical tool 1050 can be used to represent available motion scaling profiles of a surgical tool 1050.

FIG. 32 depicts a process 3100 for moving a surgical tool 1050 and/or an end effector 1052 based on selected motion scaling profiles. In at least one example, the process 3100 is executed by a control circuit such as, for example, the control circuit 1532. As illustrated in FIG. 32, the process 3100 includes receiving 3102 a user selection signal. In at least one example, the user selection signal is received 3102 by the control circuit 1532 from a motion-scaling profile selector 3014. The received 3102 user selection signal may indicate a selection between a first motion scaling profile of the motion of the surgical tool 1050 and a second motion scaling profile of the motion of the surgical tool 1050, wherein the first motion scaling profile is different than the second motion scaling profile. The process 3100 further includes receiving 3104 a motion control signal from the input control device 1000 indicative of a user input force 3010.

The process 3100 further includes causing 3106 the surgical tool 1050 to be moved in response to the motion control signal in accordance with the first motion scaling profile or the second motion scaling profile based on the user selection signal. Moving the surgical tool 1050 can be accomplished using one or more motors, for example, as described above in connection with FIGS. 1-6, for example.

In various examples, different motion scaling profiles are assigned to motions of the surgical tool 1050 along different directions. For example, a first motion scaling profile can be assigned to a motion of the surgical tool 1050 along the $X_t$ axis, while a second motion scaling profile, different than the first motion scaling profile, can be assigned to a motion of the surgical tool 1050 along the $Y_t$ axis. In other words, the user input forces 3010 can yield different rates of motion 3012 for motions of the surgical tool 1050 along different axes or for motions of the surgical tool 1050 in different directions. A control circuit such as, for example, the control circuit 1532 may determine a desired direction of motion through the sensor arrangement 1048 of the input control device 1000. The control circuit 1532 may then select a suitable motion scaling profile based on the detected direction of motion.

As described above, a user may select from a number of available profiles of motion scaling using the motion-scaling profile selector 3014, but the user-selected motion scaling profiles can be further tweaked or adjusted by the control circuit 1532 based upon certain factors such as, for example, the direction of motion of the surgical tool 1050. Other factors are also considered such as, for example, whether the input control device 1000 is in a gross motion mode or a fine motion mode. In various examples, certain motion scaling profiles are only available to the user in only one of the gross motion mode and the fine motion mode.

For example, the motion scaling profiles 3002, 3004, 3006, 3008 are gross motion scaling profiles that are available in a gross motion mode of the surgical input device 1000, and are configured to scale the motion of the surgical tool 1050 to user input forces 3010. Other suitable motion scaling profiles can be employed to scale the motion of the end effector 1052 to the user input forces 3010, for example.

Further to the above, in certain examples, motion scaling profiles for a surgical tool 1050 and/or an end effector 1052 are automatically selected by a control circuit such as, for example, the control circuit 1532. In one example, the motion scaling profiles can be automatically selected based on the distance between the surgical tool 1050 and a patient, in accordance with a process 3500. As illustrated in FIG. 33, the process 3500 includes receiving 3502 a motion control signal from the input control device 1000 indicative of a user input force 3010, and determining 3504 a distance $d_t$ between the surgical tool and a patient, which can be accomplished using one or more of the techniques described above under the heading "Surgical Visualization Systems." In at least one example, the process 3500 may determine 3404 the distance $d_t$ by transmitting an electromagnetic wave from the surgical tool 1050 to the patient, and calculating a time-of-flight of the electromagnetic wave reflected by the patient.

The process 3500 further includes selecting 3506 between predetermined motion scaling profiles based on the determined distance $d_t$. The process 3500 further includes causing 3508 the surgical tool 1050 to be moved in response to the motion control signal in accordance the selected motion scaling profile. Moving the surgical tool 1050 can be accomplished using one or more motors, for example, as described above in connection with FIGS. 1-6, for example.

In various aspects, the process 3500 further includes the distance $d_t$ to a threshold distance. In at least one example, the threshold distance can be stored in a memory 1534. The control circuit 1532 may retrieve the threshold distance from the memory 1534 and perform the comparison. In at least one example, the process 3500 includes selecting the first motion scaling profile if the distance is greater than or equal to the threshold distance. In another example, the process 3500 includes selecting the second motion scaling profile if the distance is less than or equal to the threshold distance.

Referring now to FIG. 34, a process 3600 is depicted. In at least one example, the process 3600 is executed by a control circuit such as, for example, the control circuit 1532. The process 3600 includes receiving 3602 a first motion control signal from the input control device 1000 indicative of a first user input force, and receiving a second motion control signal from the input control device 1000 indicative of a second user input force different than the first user input force. The process 3600 further includes causing 3606 the surgical tool 1050 to be moved at a predetermined rate of motion in response the first motion control signal, and causing 3608 the surgical tool 1050 to be moved at the same predetermined rate of motion in response the second motion control signal. In other words, two different user input forces may yield the same rate of motion of the surgical tool 1050. In at least one example, a control circuit such as, for example, the control circuit 1532 may select the same rate of motion of the surgical tool 1050 in response to a first user input force in a gross motion mode, and in response to a second user input force in a fine motion mode.

EXAMPLES

Various aspects of the subject matter described herein are set out in the following numbered examples:

A list of Examples follows:

Example 1—A surgical system comprising a surgical tool, a motor operably coupled to the surgical tool, and a control circuit coupled to the motor. The control circuit is configured to receive an instrument motion control signal indicative of a user input, cause the motor to move the surgical tool in response to the instrument motion control signal, receive an input signal indicative of a distance between the surgical tool and tissue, and scale the movement of the surgical tool to the user input in accordance with the input signal.

Example 2—The surgical system of Example 1, wherein the control circuit is configured to scale the movement of the surgical tool to the user input while the distance is greater than or equal to a threshold.

Example 3—The surgical system of Example 2, wherein the control circuit is configured to deactivate the scaling of the movement of the surgical tool to the user input when the distance is below the threshold.

Example 4—The surgical system of Examples 2 or 3, wherein the threshold is a first threshold. The control circuit is configured to adjust the scaling in accordance with the distance while the distance is between the first threshold and a second threshold.

Example 5—The surgical system of any one of Examples 1-4, wherein the control circuit is configured to determine the distance between the surgical tool and the tissue by causing a transmission of an electromagnetic wave from the surgical tool to the tissue and calculating a time-of-flight of the electromagnetic wave reflected by the tissue.

Example 6—The surgical system of any one of Examples 1-5, further comprising an input control device configured to transmit the instrument motion control signal to the control circuit.

Example 7—The surgical system of Example 6, wherein the input control device comprises a sensor for measuring a parameter of the user input.

Example 8—The surgical system of Example 7, wherein the sensor is a force sensor and the parameter is a force applied to the input control device.

Example 9—The surgical system of any one of Examples 1-8, wherein scaling the movement of the surgical tool comprises adjusting a force required to move the surgical tool at a given speed.

Example 10—A surgical system comprising a surgical tool, a motor operably coupled to the surgical tool, and a control circuit coupled to the motor. The control circuit is configured to receive an instrument motion control signal indicative of a user input, cause the motor to move the surgical tool in response to the instrument motion control signal, determine a distance between the surgical tool and tissue, and scale the movement of the surgical tool to the user input in accordance with the distance.

Example 11—The surgical system of Example 10, wherein the control circuit is configured to scale the movement of the surgical tool to the user input while the distance is greater than or equal to a threshold.

Example 12—The surgical system of Example 11, wherein the control circuit is configured to deactivate the scaling of the movement of the surgical tool to the user input when the distance is below the threshold.

Example 13—The surgical system of Examples 11 or 12, wherein the threshold is a first threshold. The control circuit is configured to adjust the scaling in accordance with the distance while the distance is between the first threshold and a second threshold.

Example 14—The surgical system of any one of Examples 10-13, wherein determining the distance between the surgical tool and the tissue comprises causing a transmission of an electromagnetic wave from the surgical tool to the tissue and calculating a time-of-flight of the electromagnetic wave reflected by the tissue.

Example 15—The surgical system of any one of Examples 10-14, further comprising an input control device configured to transmit the instrument motion control signal to the control circuit.

Example 16—The surgical system of Example 15, wherein the input control device comprises a sensor for measuring a parameter of the user input.

Example 17—The surgical system of Example 16, wherein the sensor is a force sensor and the parameter is a force applied to the input control device.

Example 18—A surgical system comprising a surgical tool, a motor operably coupled to the surgical tool, and a control circuit coupled to the motor. The control circuit is configured to receive an instrument motion control signal indicative of a user input, cause the motor to move the surgical tool in response to the instrument motion control signal, receive an input signal indicative of a distance between the surgical tool and tissue, and select between a gross motion mode and a fine motion mode of the surgical tool based on distance between the surgical tool and the tissue.

Example 19—The surgical system of Example 18, wherein the control circuit is configured to select the gross motion mode when the input signal is indicative of a distance greater than or equal to a threshold.

Example 20—The surgical system of Example 18, wherein the control circuit is configured to select the fine motion mode when the input signal is indicative of a distance less than or equal to a threshold.

Another list of examples follow:

Example 1—A surgical visualization system for use with a robotic surgical system that includes a surgical tool movable with respect to a tissue of a patient in response to an instrument motion control signal. The surgical visualization system comprises a camera and a control circuit coupled to the camera. The control circuit is configured to determine a distance between the surgical tool and the tissue and adjust a magnification of the camera based on the distance between the surgical tool and the tissue.

Example 2—The surgical visualization system of Example 1, wherein adjusting the magnification of the camera comprises retrieving a magnification value from a memory.

Example 3—The surgical visualization system of Examples 1 or 2, wherein determining the distance between the surgical tool and the tissue comprises receiving a signal indicative of a distance value.

Example 4—The surgical visualization system of Examples 1 or 2, wherein determining the distance between the surgical tool and the tissue comprises causing a transmission of an electromagnetic wave to the tissue and calculating a time-of-flight of the electromagnetic wave reflected by the tissue.

Example 5—The surgical visualization system of any one of Examples 1-4, wherein the magnification is linearly scaled to movement of the surgical tool.

Example 6—The surgical visualization system of any one of Examples 1-4, wherein the magnification is non-linearly scaled to movement of the surgical tool.

Example 7—The surgical visualization system of any one of Examples 1-6, further comprising a toggling mechanism for switching the surgical visualization system between automatic magnification and manual magnification.

Example 8—A robotic surgical system comprising a surgical visualization system, an input control device, and a robotic surgical system component movable with respect to a tissue of a patient in response to an instrument motion control signal generated by the input control device in response to a user input. The robotic surgical system further comprises a control circuit configured to determine a distance between the robotic surgical system component and the tissue and set a field of view of the surgical visualization system in accordance with the distance between the robotic surgical system component and the tissue.

Example 9—The robotic surgical system of Example 8, wherein the robotic surgical system component comprises a camera.

Example 10—The robotic surgical system of Examples 8 or 9, wherein determining the distance between the robotic surgical system component and the tissue comprises causing a transmission of an electromagnetic wave to the tissue and calculating a time-of-flight of the electromagnetic wave reflected by the tissue.

Example 11—The robotic surgical system of Examples 8 or 9, wherein determining the distance between the robotic surgical system component and the tissue comprises receiving a signal indicative of a distance value.

Example 12—The robotic surgical system of any one of Examples 8-11, wherein setting the field of view of the surgical visualization system comprises gradually adjusting.

Example 13—The robotic surgical system of any one of Examples 8-11, wherein setting the field of view of the surgical visualization system comprising selecting between a first field of view and a second field of view.

Example 14—A robotic surgical system comprising a surgical visualization system, an input control device, and a robotic surgical system component movable with respect to a tissue of a patient in response to an instrument motion control signal generated by the input control device in response to a user input. The robotic surgical system further comprises a control circuit configured to determine a distance between the robotic surgical system component and the tissue, select between a gross motion mode and a fine motion mode of the robotic surgical system component based on the distance between the robotic surgical system component and the tissue, and increase a field of view of the surgical visualization system in the gross motion mode.

Example 15—The robotic surgical system of Example 14, wherein the robotic surgical system component comprises a camera.

Example 16—The robotic surgical system of Examples 14 or 15, wherein determining the distance between the robotic surgical system component and the tissue comprises causing a transmission of an electromagnetic wave to the tissue and calculating a time-of-flight of the electromagnetic wave reflected by the tissue.

Example 17—The robotic surgical system of Examples 14 or 15, wherein determining the distance between the robotic surgical system component and the tissue comprises receiving a signal indicative of a distance value.

Example 18—The robotic surgical system of any one of Examples 14-17, wherein increasing the field of view is a gradual increase.

Example 19—A robotic surgical system comprising a surgical visualization system and a surgical tool movable with respect to a tissue of a patient. The robotic surgical system further comprises a control circuit configured to receive a user input signal indicative of a user input identifying a target location in the tissue, identify a target zone with respect to the target location, determine a distance between the surgical tool and the target zone, and select between a gross motion mode and a fine motion mode of the surgical tool based on the distance between the surgical tool and the target zone.

Example 20—The robotic surgical system of Example 19, wherein the control circuit is configured to cause the surgical tool to automatically return to the target zone.

Another list of examples follow:

Example 1—A robotic surgical system comprising an end effector movable relative to a tissue of a patient. The robotic surgical system further comprises a control circuit configured to determine a distance between the end effector and the tissue and cause the end effector to be transitioned between a locked configuration and an unlocked configuration based on the distance.

Example 2—The robotic surgical system of Example 1, wherein determining the distance between the end effector and the tissue comprises transmitting an electromagnetic wave from the end effector to the tissue and calculating a time-of-flight of the electromagnetic wave reflected by the tissue.

Example 3—The robotic surgical system of Examples 1 or 2, wherein the control circuit is configured to cause the end effector to be in the locked configuration if the distance is greater than or equal to a predetermined threshold.

Example 4—The robotic surgical system of Examples 1 or 2, wherein the control circuit is configured to cause the end effector to be in the unlocked configuration if the distance is less than or equal to a predetermined threshold.

Example 5—The robotic surgical system of any one of Examples 1-4, further comprising an indicator. The indicator comprises a first state representing the locked configuration and a second state representing the unlocked configuration. The control circuit is configured to switch the indicator between the first state and the second state based on the distance.

Example 6—The robotic surgical system of Example 5, wherein the indicator is disposed on the end effector.

Example 7—The robotic surgical system of any one of Examples 1 or 3-6, wherein determining the distance between the end effector and the tissue comprises receiving an input signal indicative of the distance.

Example 8—The robotic surgical system of any one of Examples 1-7, wherein the locked configuration comprises an electronic lock.

Example 9—A robotic surgical system comprising an end effector movable relative to a tissue of a patient. The robotic surgical system further comprises a control circuit configured to determine a distance between the end effector and the tissue, determine that the end effector is in an unstressed position, and maintain the end effector in a locked configuration as long as the distance remains greater than or equal to a predetermined threshold.

Example 10—The robotic surgical system of Example 9, wherein determining the distance between the end effector and the tissue comprises transmitting an electromagnetic wave from the end effector to the tissue and calculating a time-of-flight of the electromagnetic wave reflected by the tissue.

Example 11—The robotic surgical system of Examples 9 or 10, wherein the control circuit is configured to cause the end effector to be in an unlocked configuration if the distance is less than the predetermined threshold.

Example 12—The robotic surgical system of any one of Examples 9-11, further comprising an indicator. The indicator comprises a first state representing the locked configuration and a second state representing an unlocked configuration. The control circuit is configured to switch the indicator between the first state and the second state based on the distance.

Example 13—The robotic surgical system of Example 12, wherein the indicator is disposed on the end effector.

Example 14—The robotic surgical system of any one of Examples 9 or 11-13, wherein determining the distance between the end effector and the tissue comprises receiving an input signal indicative of the distance.

Example 15—The robotic surgical system of any one of Examples 9-14, wherein the locked configuration comprises an electronic lock.

Example 16—A robotic surgical system comprising an end effector movable relative to a tissue of a patient. The robotic surgical system further comprises a control circuit configured to determine a distance between the end effector and the tissue, determine that the end effector is in a stressed position, cause the end effector to be transitioned from the stressed position to an unstressed position, cause the end effector to be in a locked configuration in the unstressed position, and maintain the end effector in the locked configuration as long as the distance remains greater than or equal to a predetermined threshold.

Example 17—The robotic surgical system of Example 16, wherein determining the distance between the end effector and the tissue comprises transmitting an electromagnetic wave from the end effector to the tissue and calculating a time-of-flight of the electromagnetic wave reflected by the tissue.

Example 18—The robotic surgical system of Examples 16 or 17, wherein the control circuit is configured to cause the end effector to be in an unlocked configuration if the distance is less than the predetermined threshold.

Example 19—The robotic surgical system of Example 16, further comprising an indicator. The indicator comprises a first state representing the locked configuration and a second state representing an unlocked configuration. The control circuit is configured to switch the indicator between the first state and the second state based on the distance.

Example 20—The robotic surgical system of any one of Examples 16, 18, or 19, wherein determining the distance between the end effector and the tissue comprises receiving an input signal indicative of the distance.

Another list of examples follow:

Example 1—A robotic surgical system for treating a patient, the robotic surgical system comprises a surgical tool movable relative to the patient and a user input device comprising a base and a controller movable relative to the base to effect a motion of the surgical tool in response to a user input force. The robotic surgical system further comprises a control circuit configured to receive a user selection signal indicative of a selection between a first motion scaling profile of the motion of the surgical tool and a second motion scaling profile of the motion of the surgical tool, receive a motion control signal from the user input device indicative of a user input force, and cause the surgical tool to be moved in response to the motion control signal in accordance with the first motion scaling profile or the second motion scaling profile based on the user selection signal. The first motion scaling profile is different than the second motion scaling profile.

Example 2—The robotic surgical system of Example 1, wherein the base is stationary.

Example 3—The robotic surgical system of Examples 1 or 2, wherein the selection is made using a dial.

Example 4—The robotic surgical system of Examples 1 or 2, wherein the selection is made using a pedal assembly.

Example 5—The robotic surgical system of Examples 1 or 2, wherein the selection is made using a touch screen.

Example 6—The robotic surgical system of any one of Examples 1-5, wherein the user input device comprises a force sensor for measuring the user input force.

Example 7—A robotic surgical system for treating a patient, the robotic surgical system comprising a surgical tool movable relative to the patient and a user input device comprising a base and a controller movable relative to the base to effect a motion of the surgical tool in response to a user input force. The robotic surgical system further comprises a control circuit configured to determine a distance between the surgical tool and the patient, receive a motion control signal from the user input device indicative of the user input force, and cause the surgical tool to be moved in response to the motion control signal in accordance with a first motion scaling profile of the motion of the surgical tool or a second motion scaling profile of the motion of the surgical tool based on the distance between the surgical tool and the patient. The first motion scaling profile is different than the second motion scaling profile.

Example 8—The robotic surgical system of Example 7, wherein determining the distance between the surgical tool and the patient comprises transmitting an electromagnetic wave from the surgical tool to the patient and calculating a time-of-flight of the electromagnetic wave reflected by the patient.

Example 9—The robotic surgical system of Example 7, wherein determining the distance between the surgical tool and the patient comprises receiving an input signal indicative of the distance.

Example 10—The robotic surgical system of any one of Examples 7-9, wherein the control circuit is configured to compare the distance to a threshold distance.

Example 11—The robotic surgical system of Example 10, wherein the control circuit is configured to select the first motion scaling profile if the distance is greater than or equal to the threshold distance.

Example 12—The robotic surgical system of Example 10, wherein the control circuit is configured to select the second motion scaling profile if the distance is less than or equal to the threshold distance.

Example 13—A robotic surgical system for treating a patient, the robotic surgical system comprising a surgical tool and a user input device configured to cause the surgical tool to move relative to the patient in response to user input forces. The robotic surgical system further comprise a control circuit configured to receive a first motion control signal from the user input device indicative of a first user input force, receive a second motion control signal from the user input device indicative of a second user input force different than the first user input force, cause the surgical tool to be moved at a predetermined rate of motion in response the first motion control signal, and cause the surgical tool to be moved at the predetermined rate of motion in response the second motion control signal.

Example 14—The robotic surgical system of Example 13, wherein the second user input force is greater than the first user input force.

Example 15—The robotic surgical system of Examples 13 or 14, wherein the control circuit is configured to cause the surgical tool to be moved at the predetermined rate of motion in response the first motion control signal in a gross motion mode of the user input device.

Example 16
The robotic surgical system of any one of Examples 13-15, wherein the control circuit is configured to cause the surgical tool to be moved at the predetermined rate of motion in response the second motion control signal in a fine motion mode of the user input device.

Example 17—The robotic surgical system of any one of Examples 13-16, wherein the user input device comprises a base and a controller movable relative to the base in response to the user input forces.

Example 18—The robotic surgical system of Example 17, wherein the base is stationary.

Example 19—The robotic surgical system of any one of Examples 13-18, wherein the user input device comprises a force sensor for measuring the user input forces.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system, comprising:
   a surgical tool comprising:
      an optical waveform emitter configured to emit an array of electromagnetic radiation; and
      a waveform sensor configured to detect an effect of emitted electromagnetic radiation and generate a signal associated with the effect;
   a motor operably coupled to the surgical tool; and
   a control circuit coupled to the surgical tool and the motor, wherein the control circuit is configured to:
      receive an instrument motion control signal indicative of a user input;
      cause the motor to move the surgical tool in response to the instrument motion control signal;
      determine a distance between the surgical tool and tissue by:
         causing the optical waveform emitter to emit electromagnetic radiation;
         receiving the signal from the waveform sensor;
         calculating a time-of-flight of the emitted electromagnetic radiation reflected by the tissue; and
         determining the distance between the surgical tool and the tissue based, at least in part, on the calculated time-of-flight; and
      scale a movement of the surgical tool to the user input based, at least in part, on the determined distance.

2. The surgical system of claim 1, wherein the control circuit is configured to scale the movement of the surgical tool to the user input while the distance is greater than or equal to a threshold.

3. The surgical system of claim 2, wherein the control circuit is configured to deactivate the scaling of the movement of the surgical tool to the user input when the distance is below the threshold.

4. The surgical system of claim 2, wherein the threshold is a first threshold, and wherein the control circuit is configured to adjust the scaling in accordance with the distance while the distance is between the first threshold and a second threshold.

5. The surgical system of claim 1, further comprising an input control device configured to transmit the instrument motion control signal to the control circuit.

6. The surgical system of claim 5, wherein the input control device comprises a sensor for measuring a parameter of the user input.

7. The surgical system of claim 6, wherein the sensor is a force sensor, and wherein the parameter is a force applied to the input control device.

8. The surgical system of claim 1, wherein scaling the movement of the surgical tool comprises adjusting a force required to move the surgical tool at a given speed.

9. The surgical system of claim 1, further comprising a display coupled to the control circuit, wherein the display is configured to receive a user selection and generate signals associated with user selection, and wherein the control circuit is further configured to:
  determine a motion scaling profile from a plurality of predetermined motion scaling profiles to display to a user of the surgical system based, at least in part, on the determined distance; and
  cause the display to present the determined motion scaling profile;
  receive a signal from the display associated with the user selection of the determined motion scaling profile; and
  scale the movement of the surgical tool to the user input based, at least in part, on the user selected motion scaling profile.

10. A surgical system, comprising:
  a surgical tool comprising:
    an optical waveform emitter configured to emit an array of electromagnetic radiation; and
    a waveform sensor configured to detect an effect of emitted electromagnetic radiation and generate a signal associated with the effect;
  a motor operably coupled to the surgical tool; and
  a control circuit coupled to the motor, wherein the control circuit is configured to:
    receive an instrument motion control signal indicative of a user input;
    cause the motor to move the surgical tool in response to the instrument motion control signal;
    determine a distance between the surgical tool and tissue by:
      causing the optical waveform emitter to emit electromagnetic radiation;
      receiving the signal from the waveform sensor;
      calculating a time-of-flight of the emitted electromagnetic radiation reflected by the tissue; and
      determining the distance between the surgical tool and the tissue based, at least in part, on the calculated time-of-flight; and
    scale a movement of the surgical tool to the user input based, at least in part, on the determined distance.

11. The surgical system of claim 10, wherein the control circuit is configured to scale the movement of the surgical tool to the user input while the distance is greater than or equal to a threshold.

12. The surgical system of claim 11, wherein the control circuit is configured to deactivate the scaling of the movement of the surgical tool to the user input when the distance is below the threshold.

13. The surgical system of claim 11, wherein the threshold is a first threshold, and wherein the control circuit is configured to adjust the scaling in accordance with the distance while the distance is between the first threshold and a second threshold.

14. The surgical system of claim 10, further comprising an input control device configured to transmit the instrument motion control signal to the control circuit.

15. The surgical system of claim 14, wherein the input control device comprises a sensor for measuring a parameter of the user input.

16. The surgical system of claim 15, wherein the sensor is a force sensor, and wherein the parameter is a force applied to the input control device.

17. A surgical system, comprising:
  a surgical tool comprising:
    an optical waveform emitter configured to emit an array of electromagnetic radiation; and
    a waveform sensor configured to detect an effect of emitted electromagnetic radiation and generate a signal associated with the effect;
  a motor operably coupled to the surgical tool; and
  a control circuit coupled to the motor, wherein the control circuit is configured to:
    receive an instrument motion control signal indicative of a user input;
    cause the motor to move the surgical tool in response to the instrument motion control signal;
    determine a distance between the surgical tool and tissue by:
      causing the optical waveform emitter to emit electromagnetic radiation;
      receiving the signal from the waveform sensor;
      calculating a time-of-flight of the emitted electromagnetic radiation reflected by the tissue; and
      determining the distance between the surgical tool and the tissue based, at least in part, on the calculated time-of-flight; and
    select between a gross motion mode and a fine motion mode of the surgical tool based, at least in part, on the determined distance between the surgical tool and the tissue.

18. The surgical system of claim 17, wherein the control circuit is configured to select the gross motion mode when the determined distance is indicative of a distance greater than or equal to a threshold.

19. The surgical system of claim 17, wherein the control circuit is configured to select the fine motion mode when the determined distance is indicative of a distance less than or equal to a threshold.

* * * * *